(12) United States Patent
Jahns et al.

(10) Patent No.: US 8,716,030 B2
(45) Date of Patent: May 6, 2014

(54) MEANS FOR THE INHIBITION OF ANTI-β1-ADRENERGIC RECEPTOR ANTIBODIES

(75) Inventors: Roland Jahns, Würzburg (DE); Valérie Jahns, Würzburg (DE); Martin J. Lohse, Würzburg (DE); Dieter Palm, Gerbrunn (DE)

(73) Assignee: Julius-Maximillians-Universitat Wurzburg, A Germany University, Wurzburg (DE)

( * ) Notice: Subject to any disclaimer, the term of this patent is extended or adjusted under 35 U.S.C. 154(b) by 0 days.

(21) Appl. No.: 13/449,966

(22) Filed: Apr. 18, 2012

(65) Prior Publication Data

US 2012/0288870 A1     Nov. 15, 2012

Related U.S. Application Data

(62) Division of application No. 11/910,258, filed as application No. PCT/EP2006/002977 on Mar. 31, 2006, now Pat. No. 8,187,605.

(30) Foreign Application Priority Data

Mar. 31, 2005   (EP) .................................... 05007056

(51) Int. Cl.
    *G01N 33/564*     (2006.01)
(52) U.S. Cl.
    USPC .......................................... 436/506; 436/811
(58) Field of Classification Search
    None
    See application file for complete search history.

(56) References Cited

U.S. PATENT DOCUMENTS

| 4,880,635 A | 11/1989 | Janoff et al. |
| 6,750,321 B1 | 6/2004 | Chen et al. |
| 7,309,488 B2 | 12/2007 | Ogino et al. |
| 8,187,605 B2 * | 5/2012 | Jahns et al. ................ 424/185.1 |

FOREIGN PATENT DOCUMENTS

| WO | WO0121660 A1 | 3/2001 |
| WO | WO2005052186 A1 | 6/2005 |

OTHER PUBLICATIONS

Freedman, Neil J., Lefkowitz, Robert J.; Anti-B1-Adrenergic Receptor Antibodies and Heart Failure: Causation, Not Just Correlation; The Journal of Clinical Investigation, vol. 113, No. 10 (May 2004), pp. 1379-1382.

Hempel, Chris M., Vincent, Pierre, Adams, Stephen R., Tsien, Roger Y., Selverston, Allen I., Spatio-Temporal Dynamics of Cyclic AMP Signals in an Intact Neural Circuit; Nature, vol. 384, (Nov. 14, 1996), pp. 166-169.

(Continued)

*Primary Examiner* — Jeffrey E Russel
(74) *Attorney, Agent, or Firm* — Faegre Baker Daniels LLP

(57) ABSTRACT

Embodiments of the present invention provide for novel peptides of use for detection and/or inhibition of anti-β1-adrenergic receptor antibodies. Certain embodiments concern uses of cyclic and/or linear peptides. In other embodiments, the present invention relates to novel peptides of use in diagnostic and/or pharmaceutical compositions. Some embodiments concern diagnosing and/or treating cardiac conditions. Cardiac conditions of the instant invention can concern infectious heart disease, non-infectious heart disease, ischemic heart disease, non-ischemic heart disease, inflammatory heart disease, myocarditis, cardiac dilatation, idiopathic cardiomyopathy, idiopathic dilated cardiomyopathy, immune-cardiomyopathy, heart failure, and any cardiac arrhythmia condition.

20 Claims, 30 Drawing Sheets

(56) References Cited

OTHER PUBLICATIONS

Figure 1:
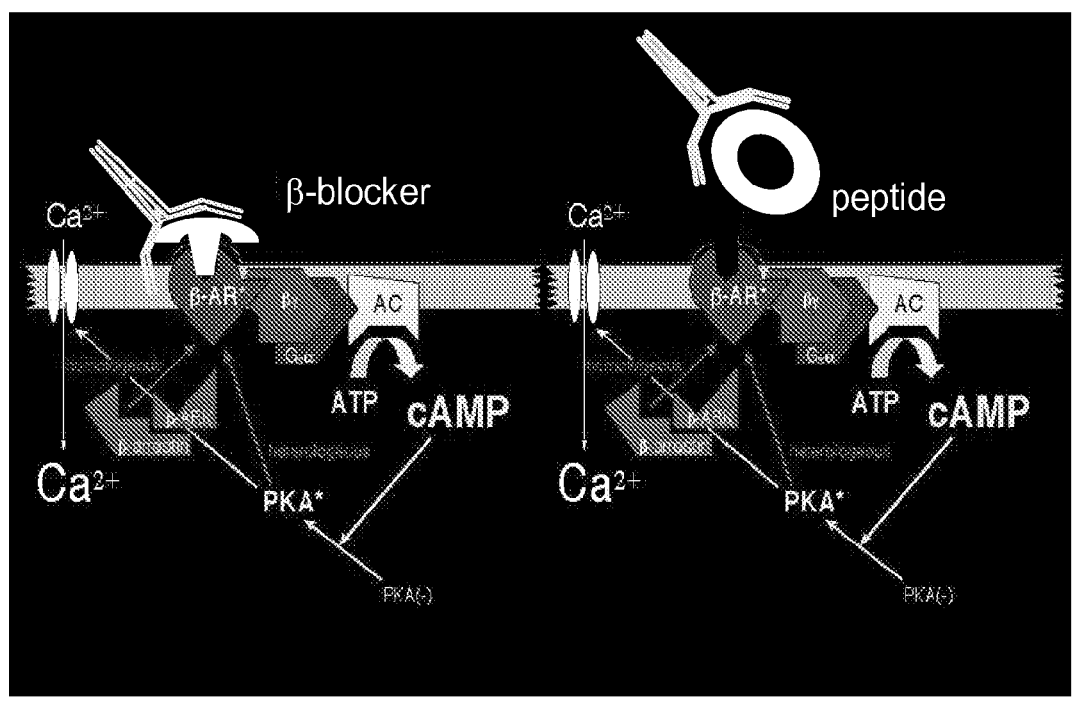

Hoebeke, Johan; Guillet, Jean-Gerard; Strosberg, A. Donny; Use of Receptors Expressed in *Escherichia coli* to Study Autoimmunity against G Protein-Coupled Membrane Proteins, Methods in Neurosciences, vol. 25, pp. 345-365, (1995).

International Preliminary Report on Patentability for International Patent Application No. PCT/EP2006/002977, Feb. 21, 2007.

International Search Report and Written Opinion for International Patential Application No. PCT/EP2006/002977, Oct. 17, 2006.

Ireland, David C.; Colgrave, Michelle L; Nguyencong, Philip; Daly, Norelle L.; Craik, David J.; Discovery and Characterization of a Linear Cyclotide from Viola odorata: Implications for the Processing of Circular Proteins; J. Mol. Biol. (2006), 357, pp. 1522-1535.

Jahns, Roland, "A New Cyclic Receptor-Peptide Prevents Development of Heart Dilatation and Failure Induced by Antibodies Activating Cardiac B1 Adrenergic Receptors," Advanced in Receptor-Based Therapeutics in the Heart and Kidney, Abstract from Scientific Sessions, No. 120, (Oct. 2005).

Jahns, Roland, MD, Boivin, Valerie, PhD, Krapf, Thorsten; Wallukat, Gerd MD, Boege, Fritz, MD; Lohse, Martin J., MD; Modulation of Beta1-Adrenoceptor Activity by Domain-Specific Antibodies and Heart Failure-Associated Autoantibodies, vol. 36, No. 4, (2000) pp. 1280-1287.

Jahns, Roland, MD; Boivin, Valerie, PhD; Siegmund, Christian; Inselman, Gerhard, MD; Lohse, Martin J.; Boege, Fritz, MD; Autoantibodies Activating Human B1-Adrenergic Receptors are Associated with Reduced Cardiac Function in Chronic Heart Failure, pp. 649-654. www.circulationaha.org, (1999).

Jahns, Roland, Siegmund, Christian, Jahns, Valerie, Reilander, Helmut, Maidhof, Muller-Esterl, Werner, Lohse, Martin J., Boege, Fritz; Probing Human B1-and B2-Adrenoceptors with Domain-Specific Fusion Protein Antibodies; European Journal of Pharmacology, 316 (1996) pp. 111-121.

Jahns, Roland; Boivin, Valerie; Hein, Lutz; Triebel, Sven; Angermann, Christiane E.; Ertl, Georg; Lohse, Martin J.; Direct Evidence for a B1-Adrenergic Receptor-Directred Autoimmune Attack as a Cause of Idiopathic Dilated Cardiomyopathy; The Journal of Clinical Investigation, vol. 113, No. 10, (May 2004) pp. 1419-1429.

Mobini, R.; Magnusson, Y.; Wallukat, G.; Viguier, M.; Hjalmarson, A.; Hoebeke, J.; Probing the Immunological Properties of the Extracellular Domains of the Human B1-Adrenceptor; Journal of Autoimmunity (1999), 13, pp. 179-186.

Nikolaev, Viacheslav O.; Bunemann, Lutz Hein; Hannawacker, Annette; Lohse, Martin J,; Novel Single Chain cAMP Sensors for Receptor-Induced Signal Propagation; The Journal of Biological Chemistry, vol. 279, No. 36, (Sep. 3, 2004) pp. 37215-37218.

Report of 1995 World Health Organization/International Society and Federation of Cardiology Task Force on the Definition and Classification of Cardiomyopathies; Circulation; (1996) pp. 841-842.

Schulze, Karsten, MD; Becker, Bernhard F., MD; Schauer, Rolf; Schultheiss, Heinz P.; Antibodies to ADP-ATP Carrier-an Autoantigen in Myocarditis and Dilated Cardiomyopathy-Impair Cardiac Function; Circulation, vol. 81, No. 3 (Mar. 1990), pp. 959-969.

Zaccolo, Manuela; Pozzan, Tullio; Discrete Microdomains with High Concentration of cAMP in Stimulated Rat Neonatal Cardiac Myocytes; Science, vol. 295, (Mar. 1, 2002), pp. 1711-1715.

Dorow, D.S. et al. "Two Large Immunogenic And Antigenic Myoglobin Peptides And The Effects Of Cyclisation," The Journal of Immunology, vol. 22, No. 11, pp. 1255-1264, 1985.

\* cited by examiner

```
                         SEQUENCE LISTING

<160> NUMBER OF SEQ ID NOS: 16

<210> SEQ ID NO 1
<211> LENGTH: 18
<212> TYPE: PRT
<213> ORGANISM: Artificial
<220> FEATURE:
<223> OTHER INFORMATION: Fragment of beta-1-ECII peptide

<400> SEQUENCE: 1

Ala Asp Glu Ala Arg Arg Cys Tyr Asn Asp Pro Lys Cys Cys Asp Phe
1               5                   10                  15

Val Gln

<210> SEQ ID NO 2
<211> LENGTH: 16
<212> TYPE: PRT
<213> ORGANISM: Artificial
<220> FEATURE:
<223> OTHER INFORMATION: Fragment of beta-1-ECII peptide

<400> SEQUENCE: 2

Ala Arg Arg Cys Tyr Asn Asp Pro Lys Cys Cys Asp Phe Val Tyr Gln
1               5                   10                  15

<210> SEQ ID NO 3
<211> LENGTH: 25
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (2)..(10)
<223> OTHER INFORMATION: Xaa is any amino acid
<220> FEATURE:
<221> NAME/KEY: MISC_FEATURE
<222> LOCATION: (12)..(14)
<223> OTHER INFORMATION: Xaa is any amino acid
<220> FEATURE:
<221> NAME/KEY: MISC_FEATURE
<222> LOCATION: (16)..(16)
<223> OTHER INFORMATION: Xaa is any amino acid
<220> FEATURE:
<221> NAME/KEY: MISC_FEATURE
<222> LOCATION: (19)..(24)
<223> OTHER INFORMATION: Xaa is either absent or present at positions 19
      to 24, and if present is any amino acid

<400> SEQUENCE: 3

Ala Xaa Xaa Xaa Xaa Xaa Xaa Xaa Xaa Xaa Cys Xaa Xaa Xaa Pro Xaa
1               5                   10                  15

Cys Cys Xaa Xaa Xaa Xaa Xaa Xaa Gln
                20                  25
```

```
<210> SEQ ID NO 4
<211> LENGTH: 14
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (2)..(3)
<223> OTHER INFORMATION: Xaa is any amino acid
<220> FEATURE:
<221> NAME/KEY: MISC_FEATURE
<222> LOCATION: (5)..(6)
<223> OTHER INFORMATION: Xaa is any amino acid
<220> FEATURE:
<221> NAME/KEY: MISC_FEATURE
<222> LOCATION: (8)..(8)
<223> OTHER INFORMATION: Xaa is any amino acid
<220> FEATURE:
<221> NAME/KEY: MISC_FEATURE
<222> LOCATION: (10)..(10)
<223> OTHER INFORMATION: Xaa is any amino acid
<220> FEATURE:
<221> NAME/KEY: MISC_FEATURE
<222> LOCATION: (12)..(13)
<223> OTHER INFORMATION: Xaa is either absent or present at positions 12
      to 13, and if present is any amino acid

<400> SEQUENCE: 4

Ala Xaa Xaa Trp Xaa Xaa Gly Xaa Phe Xaa Cys Xaa Xaa Gln
1               5                   10

<210> SEQ ID NO 5
<211> LENGTH: 30
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (2)..(10)
<223> OTHER INFORMATION: Xaa is any amino acid
<220> FEATURE:
<221> NAME/KEY: MISC_FEATURE
<222> LOCATION: (12)..(15)
<223> OTHER INFORMATION: Xaa is either absent or present at positions 12
      to 15, and if present is any amino acid
<220> FEATURE:
<221> NAME/KEY: MISC_FEATURE
<222> LOCATION: (17)..(19)
<223> OTHER INFORMATION: Xaa is any amino acid
<220> FEATURE:
<221> NAME/KEY: MISC_FEATURE
<222> LOCATION: (21)..(21)
<223> OTHER INFORMATION: Xaa is any amino acid
<220> FEATURE:
<221> NAME/KEY: MISC_FEATURE
<222> LOCATION: (24)..(29)
<223> OTHER INFORMATION: Xaa is either absent or present at positions 24
      to 29, and if present is any amino acid

<400> SEQUENCE: 5

Ala Xaa Xaa Xaa Xaa Xaa Xaa Xaa Xaa Xaa Cys Xaa Xaa Xaa Xaa Cys
1               5                   10                  15

Xaa Xaa Xaa Pro Xaa Cys Cys Xaa Xaa Xaa Xaa Xaa Xaa Gln
            20                  25                  30

<210> SEQ ID NO 6
<211> LENGTH: 30
<212> TYPE: PRT
<213> ORGANISM: Artificial
<220> FEATURE:
<223> OTHER INFORMATION: synthetic
```

```
<220> FEATURE:
<221> NAME/KEY: MISC_FEATURE
<222> LOCATION: (2)..(10)
<223> OTHER INFORMATION: Xaa is either absent or present at positions 2
      to 10, and if present is any amino acid
<220> FEATURE:
<221> NAME/KEY: MISC_FEATURE
<222> LOCATION: (12)..(15)
<223> OTHER INFORMATION: Xaa is any amino acid
<220> FEATURE:
<221> NAME/KEY: MISC_FEATURE
<222> LOCATION: (17)..(19)
<223> OTHER INFORMATION: Xaa is any amino acid
<220> FEATURE:
<221> NAME/KEY: MISC_FEATURE
<222> LOCATION: (21)..(21)
<223> OTHER INFORMATION: Xaa is any amino acid
<220> FEATURE:
<221> NAME/KEY: MISC_FEATURE
<222> LOCATION: (24)..(29)
<223> OTHER INFORMATION: Xaa is either absent or present at positions 24
      to 29, and if present is any amino acid

<400> SEQUENCE: 6

Ala Xaa Xaa Xaa Xaa Xaa Xaa Xaa Xaa Xaa Cys Xaa Xaa Xaa Xaa Cys
1               5                   10                  15

Xaa Xaa Xaa Pro Xaa Cys Cys Xaa Xaa Xaa Xaa Xaa Gln
            20                  25                  30

<210> SEQ ID NO 7
<211> LENGTH: 25
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (2)..(2)
<223> OTHER INFORMATION: Xaa is a basic amino acid
<220> FEATURE:
<221> NAME/KEY: MISC_FEATURE
<222> LOCATION: (3)..(3)
<223> OTHER INFORMATION: Xaa is any amino acid
<220> FEATURE:
<221> NAME/KEY: MISC_FEATURE
<222> LOCATION: (4)..(4)
<223> OTHER INFORMATION: Xaa is an acidic amino acid
<220> FEATURE:
<221> NAME/KEY: MISC_FEATURE
<222> LOCATION: (5)..(5)
<223> OTHER INFORMATION: Xaa is any amino acid
<220> FEATURE:
<221> NAME/KEY: MISC_FEATURE
<222> LOCATION: (6)..(7)
<223> OTHER INFORMATION: Xaa is an acidic amino acid
<220> FEATURE:
<221> NAME/KEY: MISC_FEATURE
<222> LOCATION: (8)..(8)
<223> OTHER INFORMATION: Xaa is any amino acid
<220> FEATURE:
<221> NAME/KEY: MISC_FEATURE
<222> LOCATION: (9)..(10)
<223> OTHER INFORMATION: Xaa is any basic amino acid
<220> FEATURE:
<221> NAME/KEY: MISC_FEATURE
<222> LOCATION: (12)..(13)
<223> OTHER INFORMATION: Xaa is any amino acid
<220> FEATURE:
<221> NAME/KEY: MISC_FEATURE
<222> LOCATION: (14)..(14)
<223> OTHER INFORMATION: Xaa is any acidic amino acid
<220> FEATURE:
<221> NAME/KEY: MISC_FEATURE
<222> LOCATION: (16)..(16)
<223> OTHER INFORMATION: Xaa is any amino acid
```

```
<220> FEATURE:
<221> NAME/KEY: MISC_FEATURE
<222> LOCATION: (19)..(24)
<223> OTHER INFORMATION: Xaa is either absent or present at positions 19
      to 24, and if present is any amino acid

<400> SEQUENCE: 7

Ala Xaa Xaa Xaa Xaa Xaa Xaa Xaa Xaa Xaa Cys Xaa Xaa Xaa Pro Xaa
1               5                   10                  15

Cys Cys Xaa Xaa Xaa Xaa Xaa Xaa Gln
            20                  25

<210> SEQ ID NO 8
<211> LENGTH: 25
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa is any amino acid selected from Ser, Thr,
      Ala and Gly
<220> FEATURE:
<221> NAME/KEY: MISC_FEATURE
<222> LOCATION: (2)..(2)
<223> OTHER INFORMATION: Xaa is any basic amino acid
<220> FEATURE:
<221> NAME/KEY: MISC_FEATURE
<222> LOCATION: (3)..(3)
<223> OTHER INFORMATION: Xaa is any amino acid selected from Ser, Thr,
      Ala and Gly
<220> FEATURE:
<221> NAME/KEY: MISC_FEATURE
<222> LOCATION: (4)..(4)
<223> OTHER INFORMATION: Xaa is any acidic amino acid
<220> FEATURE:
<221> NAME/KEY: MISC_FEATURE
<222> LOCATION: (5)..(5)
<223> OTHER INFORMATION: Xaa is any amino acid selected from Ser, Thr,
      Ala and Gly
<220> FEATURE:
<221> NAME/KEY: MISC_FEATURE
<222> LOCATION: (6)..(7)
<223> OTHER INFORMATION: Xaa is any acidic amino acid
<220> FEATURE:
<221> NAME/KEY: MISC_FEATURE
<222> LOCATION: (8)..(8)
<223> OTHER INFORMATION: Xaa is any amino acid selected from Ser, Thr,
      Ala and Gly
<220> FEATURE:
<221> NAME/KEY: MISC_FEATURE
<222> LOCATION: (9)..(10)
<223> OTHER INFORMATION: Xaa is any basic amino acid
<220> FEATURE:
<221> NAME/KEY: MISC_FEATURE
<222> LOCATION: (12)..(12)
<223> OTHER INFORMATION: Xaa is any amino acid selected from Leu, Ile,
      Val, Met, Trp, Tyr and Phe
<220> FEATURE:
<221> NAME/KEY: MISC_FEATURE
<222> LOCATION: (13)..(13)
<223> OTHER INFORMATION: Xaa is any amino acid selected from Gln and Asn
<220> FEATURE:
<221> NAME/KEY: MISC_FEATURE
<222> LOCATION: (14)..(14)
<223> OTHER INFORMATION: Xaa is any acidic amino acid
<220> FEATURE:
<221> NAME/KEY: MISC_FEATURE
<222> LOCATION: (16)..(16)
<223> OTHER INFORMATION: Xaa is any basic amino acid
<220> FEATURE:
<221> NAME/KEY: MISC_FEATURE
<222> LOCATION: (19)..(19)
<223> OTHER INFORMATION: Xaa is any acidic amino acid
```

-continued

```
<220> FEATURE:
<221> NAME/KEY: MISC_FEATURE
<222> LOCATION: (20)..(21)
<223> OTHER INFORMATION: Xaa is any amino acid selected from Leu, Ile,
      Val, Met, Trp, Tyr and Phe
<220> FEATURE:
<221> NAME/KEY: MISC_FEATURE
<222> LOCATION: (22)..(22)
<223> OTHER INFORMATION: Xaa is any amino acid selected from Ser, Thr,
      Ala and Gly
<220> FEATURE:
<221> NAME/KEY: MISC_FEATURE
<222> LOCATION: (23)..(23)
<223> OTHER INFORMATION: Xaa is any amino acid selected from Gln and Asn
<220> FEATURE:
<221> NAME/KEY: MISC_FEATURE
<222> LOCATION: (24)..(24)
<223> OTHER INFORMATION: Xaa is any basic amino acid
<220> FEATURE:
<221> NAME/KEY: MISC_FEATURE
<222> LOCATION: (25)..(25)
<223> OTHER INFORMATION: Xaa is any amino acid selected from Gln and Asn

<400> SEQUENCE: 8

Xaa Xaa Xaa Xaa Xaa Xaa Xaa Xaa Xaa Xaa Cys Xaa Xaa Xaa Pro Xaa
1               5                   10                  15

Cys Cys Xaa Xaa Xaa Xaa Xaa Xaa Xaa
            20                  25

<210> SEQ ID NO 9
<211> LENGTH: 25
<212> TYPE: PRT
<213> ORGANISM: Artificial
<220> FEATURE:
<223> OTHER INFORMATION: synthetic

<400> SEQUENCE: 9

Ala Arg Ala Glu Ser Asp Glu Ala Arg Arg Cys Tyr Asn Asp Pro Lys
1               5                   10                  15

Cys Cys Asp Phe Val Thr Asn Arg Gln
            20                  25

<210> SEQ ID NO 10
<211> LENGTH: 14
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (2)..(2)
<223> OTHER INFORMATION: Xaa is any amino acid selected from Ser, Thr,
      Ala and Gly
<220> FEATURE:
<221> NAME/KEY: MISC_FEATURE
<222> LOCATION: (3)..(3)
<223> OTHER INFORMATION: Xaa is any basic amino acid
<220> FEATURE:
<221> NAME/KEY: MISC_FEATURE
<222> LOCATION: (5)..(5)
<223> OTHER INFORMATION: Xaa is any acidic amino acid
<220> FEATURE:
<221> NAME/KEY: MISC_FEATURE
<222> LOCATION: (6)..(6)
<223> OTHER INFORMATION: Xaa is any amino acid selected from Leu, Ile,
      Val, Met, Trp, Tyr and Phe
<220> FEATURE:
<221> NAME/KEY: MISC_FEATURE
<222> LOCATION: (8)..(8)
<223> OTHER INFORMATION: Xaa is any amino acid selected from Ser, Thr,
      Ala and Gly
```

```
<220> FEATURE:
<221> NAME/KEY: MISC_FEATURE
<222> LOCATION: (10)..(10)
<223> OTHER INFORMATION: Xaa is any amino acid selected from Le -continued

```
<220> FEATURE:
<221> NAME/KEY: MISC_FEATURE
<222> LOCATION: (9)..(10)
<223> OTHER INFORMATION: Xaa is any amino acid selected from Leu, Ile,
      Val, Met, Trp, Tyr and Phe
<220> FEATURE:
<221> NAME/KEY: MISC_FEATURE
<222> LOCATION: (12)..(15)
<223> OTHER INFORMATION: Xaa is either absent or present at positions 12
      to 15, and if present is any amino acid
<220> FEATURE:
<221> NAME/KEY: MISC_FEATURE
<222> LOCATION: (17)..(19)
<223> OTHER INFORMATION: Xaa is any amino acid
<220> FEATURE:
<221> NAME/KEY: MISC_FEATURE
<222> LOCATION: (21)..(21)
<223> OTHER INFORMATION: Xaa is any amino acid
<220> FEATURE:
<221> NAME/KEY: MISC_FEATURE
<222> LOCATION: (24)..(29)
<223> OTHER INFORMATION: Xaa is either absent or present at positions 24
      to 29, and if present is any amino acids

<400> SEQUENCE: 13

Ala Xaa Xaa Xaa Xaa Xaa Xaa Xaa Xaa Xaa Cys Xaa Xaa Xaa Xaa Cys
1               5                   10                  15

Xaa Xaa Xaa Pro Xaa Cys Cys Xaa Xaa Xaa Xaa Xaa Xaa Gln
            20                  25                  30

<210> SEQ ID NO 14
<211> LENGTH: 30
<212> TYPE: PRT
<213> ORGANISM: Artificial
<220> FEATURE:
<223> OTHER INFORMATION: synthetic

<400> SEQUENCE: 14

Ala Gly Arg Trp Glu Tyr Gly Ser Phe Phe Cys Glu Ala Arg Arg Cys
1               5                   10                  15

Tyr Asn Asp Pro Lys Cys Cys Asp Phe Val Thr Asn Arg Gln
            20                  25                  30

<210> SEQ ID NO 15
<211> LENGTH: 30
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (2)..(2)
<223> OTHER INFORMATION: Xaa is any amino acid selected from Ser, Thr,
      Ala and Gly
<220> FEATURE:
<221> NAME/KEY: MISC_FEATURE
<222> LOCATION: (3)..(3)
<223> OTHER INFORMATION: Xaa is any basic amino acid
<220> FEATURE:
<221> NAME/KEY: MISC_FEATURE
<222> LOCATION: (4)..(4)
<223> OTHER INFORMATION: Xaa is any amino acid selected from Leu, Ile,
      Val, Met, Trp, Tyr and Phe
<220> FEATURE:
<221> NAME/KEY: MISC_FEATURE
<222> LOCATION: (5)..(5)
<223> OTHER INFORMATION: Xaa is any acidic amino acid
<220> FEATURE:
<221> NAME/KEY: MISC_FEATURE
<222> LOCATION: (6)..(7)
<223> OTHER INFORMATION: Xaa is any amino acid selected from Leu, Ile,
      Val, Met, Trp, Tyr and Phe
```

```
<220> FEATURE:
<221> NAME/KEY: MISC_FEATURE
<222> LOCATION: (8)..(8)
<223> OTHER INFORMATION: Xaa is any amino acid selected from Ser, Thr,
      Ala and Gly
<220> FEATURE:
<221> NAME/KEY: MISC_FEATURE
<222> LOCATION: (9)..(10)
<223> OTHER INFORMATION: Xaa is any amino acid selected from Leu, Ile,
      Val, Met, Trp, Tyr and Phe
<220> FEATURE:
<221> NAME/KEY: MISC_FEATURE
<222> LOCATION: (12)..(15)
<223> OTHER INFORMATION: Xaa is either absent or present at positions 12
      to 15, and if present is any amino acid
<220> FEATURE:
<221> NAME/KEY: MISC_FEATURE
<222> LOCATION: (17)..(19)
<223> OTHER INFORMATION: Xaa is any amino acid
<220> FEATURE:
<221> NAME/KEY: MISC_FEATURE
<222> LOCATION: (21)..(21)
<223> OTHER INFORMATION: Xaa is any amino acid
<220> FEATURE:
<221> NAME/KEY: MISC_FEATURE
<222> LOCATION: (24)..(29)
<223> OTHER INFORMATION: Xaa is either absent or present at positions 24
      to 29, and if present is any amino acid

<400> SEQUENCE: 15

Ala Xaa Xaa Xaa Xaa Xaa Xaa Xaa Xaa Cys Xaa Xaa Xaa Xaa Cys
1               5                   10                  15

Xaa Xaa Xaa Pro Xaa Cys Cys Xaa Xaa Xaa Xaa Xaa Xaa Gln
            20                  25                  30

<210> SEQ ID NO 16
<211> LENGTH: 30
<212> TYPE: PRT
<213> ORGANISM: Artificial
<220> FEATURE:
<223> OTHER INFORMATION: synthetic

<400> SEQUENCE: 16

Ala Gly Arg Trp Glu Tyr Gly Ser Phe Phe Cys Glu Ala Arg Cys
1               5                   10                  15

Tyr Asn Asp Pro Lys Cys Cys Asp Phe Val Thr Asn Arg Gln
            20                  25                  30
```

MEANS FOR THE INHIBITION OF ANTI-β1-ADRENERGIC RECEPTOR ANTIBODIES

CROSS REFERENCE TO RELATED APPLICATIONS

This application is a divisional of, and claims priority to U.S. Pat. No. 8,187,605 previously application Ser. No. 11/910,258, filed Oct. 1, 2008, which claims priority to PCT Application No. PCT/EP2006/002977, filed Mar. 31, 2006. Both applications are incorporated herein by reference in their entirety for all purposes.

The present invention is related to peptides, their use in the detection and inhibition of anti-β1-adrenergic receptor antibodies and diagnostic agents and pharmaceutical compositions containing the same.

Dilated cardiomyopathy (DCM) is a severe cardiac disease of young adults which will result in continuous decline of cardiac function if not treated. Said decline is based on a reduced cardiac function going along with dilatation of the heart muscle. In about 30% of the cases dilated cardiomyopathy is of genetic origin, about 10% of the cases are caused by toxic substances such as alcohol and chemotherapeutics and the remaining 60% of the cases are caused by acute or chronic infection of the heart muscle and concomitantly occurring immunological secondary reactions. Ultimately, heart transplantation is the means of choice for the treatment of dilated cardiomyopathy. Without treatment the patient is facing an untimely death (Richardson et al. (1996) Circulation, 93, 841-842).

In idiopathic dilated cardiomyopathy which is characterised by a loss of heart function without defined aetiology, a correlation of heart disease and autoimmune reactions against various myocardial antigens was found, such as autoantibodies against the heavy chain of myosin, laminin and the ADP/ATP transporter (Schulze et al. (1990) Circulation, 81, 859-869). However, there was no evidence that any of these antigens is relevant in terms of pathogenesis. In contrast thereto, functionally active antibodies against cardiac β1-receptors have been shown to play an important role in the pathogenesis of dilated cardiomyopathy. Immunological analysis have shown that the second out of a total of three extracellular domains of the β1-adrenergic receptor exhibits both a T-cell epitope and a B-cell epitope (Hoebecke et al. (1994), Methods Neuroscie. 25, 345-365) and meets thus the criteria for an auto-antigen in accordance with the first Witebsky's postulate.

In order to provide experimental evidence that this auto-antigen is relevant for the etiology of dilated cardiomyopathy, it was tried to induce immune cardiomyopathy in accordance with the second Witebsky's postulate. In a rat model experimental evidence was provided that stimulatory anti-β1-AR antibodies against the second extracellular domain of the β1-adrenergic receptor are involved in the etiology of dilated cardiomyopathy (β1-EC$_{II}$) (Jahns et al. (2004) J. Clin. Invest. 113, 1419-1429). The β1-EC$_{II}$/GST fusion protein used showed 100% homology between human and rat. Each of the animals immunized against β1-EC$_{II}$ developed stimulatory anti-β1-antibodies and severe progressive dilatation and pump function failure of the left ventricle corresponding to immune cardiomyopathy which could be detected by echocardiography and was confirmed by invasive measurements and histologic analysis of the animals. In order to simulate β1-autoantibodies the serum of β1-antibody positive animals was transferred intravenously to genetically identical rats every four weeks. Again, a slowly progressive dilated immune cardiomyopathy was observed nine months after serum transfer as evidenced by echocardiography and as also confirmed by invasive measurements and morphological and histological studies of the hearts of the transfer animals. Using this approach, for the very first time it was shown that β1-antibody-induced immune cardiomyopathy can be transferred and meets thus the classical third Witebsky's postulate for an autoimmune pathogenesis of dilated cardiomyopathy (Freedman & Lefkowitz (2004) J. Clin. Invest. 113, 1378-1382).

In addition to the animal studies blood samples from patients were analyzed for β1-receptor antibodies. Jahns et al. detected auto-antibodies against recombinant human β1-receptors in about 30% of all patients suffering from cardiac failure and idiopathic dilated cardiomyopathy. These patients exhibit a significantly decreased cardiac function compared to patients without such β1-receptor antibodies (Jahns et al. (1999), Circulation 99, 649-654). The stimulatory effect of the antibodies could be abolished by the cardioselective β1-receptor blocker bisoprolol. In view of this, Jahns et al. (Jahns et al. (1999), Circulation 99, 649-654; Jahns et al. (2000) JACC. 36, 1280-1287; Jahns et al. (2004) JCI. 113, 1419-1429) suggested to use β1-receptor antagonists such as bisoprolol as inhibitors of the interaction between anti-β1-adrenergic receptor antibodies and the native recombinant and non-recombinant β1-adrenergic receptors.

An alternative therapeutic approach for the treatment of dilated cardiomyopathy is the removal of the antibodies from the circulation of patients with functionally active and potentially harmful β1-receptor antibodies using immunoadsorption or immunoapharesis. In such a procedure, the blood of the patient is passed through columns removing the auto-antibody against β1-adrenergic receptors using a matrix coupled non-receptor homologous peptide or by inspecifically removing antibodies of the IgG subclass by binding the antibodies to protein A columns or to matrix coupled goat-anti-human IgG antibody. Such procedure, however, is both time and labour consuming. Additionally, due to the unspecific elimination of all immunoglobulins from the blood of the thus treated patients, numerous draw-backs arise such as an imbalanced immune system and immune response. Nevertheless it seems that antibody-positive DCM patients have at least a short term benefit from such treatment.

The problem underlying the present invention is thus to provide further means for the inhibition of anti-β1-adrenergic receptor antibodies. More particularly, the problem underlying the present invention is to provide means for the inhibition of anti-β1-adrenergic receptor antibodies.

The problem underlying the present invention is solved in a first aspect by a peptide selected from the group comprising
 a) a cyclic peptide of formula I:

(SEQ ID NO: 3)
cyclo(Ala-x-x-x-x-x-x-x-x-x-Cys-x-x-x-Pro-x-Cys-

Cys-x$_k$-Gln), (I)

whereby k is any integer from 0 to 6, preferably any integer from 1 to 6, more preferably k=6;
 b) a cyclic peptide of formula II:

(SEQ ID NO: 4)
Cyclo(Ala-x-x-Trp-x-x-Gly-x-Phe-x-Cys-x-x$_h$-Gln), (II)

whereby h is any integer from 0 to 2, preferably 1 or 2;

c) a cyclic peptide of formula III:

(SEQ ID NO: 5)
Cyclo(Ala-x-x-x-x-x-x-x-x-x-Cys-$x_j$-Cys-x-x-x-Pro-x-Cys-Cys-$x_i$-Gln), (III)

whereby j is any integer from 0 to 4, preferably j=4;
whereby i is any integer from 0 to 6, preferably any integer from 1 to 6, more preferably i=6; and
d) a peptide of formula IV:

(SEQ ID NO: 6)
Ala-$x_l$-Cys-$x_m$-Cys-x-x-x-Pro-x-Cys-Cys-$x_n$-Gln, (IV)

whereby l is any integer from 0 to 9, preferably any integer from 1 to 9, more preferably n=9;
whereby m is any integer from 0 to 4, preferably any integer from 1 to 4, more preferably m=4;
whereby n is any integer from 0 to 6, preferably any integer from 1 to 6, more preferably n=6;
whereby x is any amino acid, preferably any naturally occurring amino acid, more preferably any naturally occurring L-amino acid.

In an embodiment the peptide is a cyclic peptide of formula Ia:

(SEQ ID NO: 7)
cyclo(Ala-$x_2$-x-$x_1$-x-$x_1$-$x_1$-x-$x_2$-$x_2$-Cys-x-x-$x_1$-Pro-x-Cys-Cys-$x_k$-Gln), (Ia)

whereby k is any integer from 0 to 6, preferably any integer from 1 to 6, more preferably k=6;
whereby $x_1$ is individually and independently selected from the group comprising acidic amino acids; and
$x_2$ is individually and independently selected from the group comprising basic amino acids.

In an embodiment the peptide is a cyclic peptide of formula Ib:

(SEQ ID NO: 8)
Cyclo($x_4$-$x_2$-$x_4$-$x_1$-$x_4$-$x_1$-$x_1$-$x_4$-$x_2$-$x_2$-Cys-$x_3$-$x_5$-$x_1$-Pro-$x_2$-Cys-Cys-$x_1$-$x_3$-$x_3$-$x_4$-$x_5$-$x_2$-$x_5$), (Ib)

whereby $x_1$ is individually and independently selected from the group comprising acidic amino acids;
$x_2$ is individually and independently selected from the group comprising basic amino acids;
$x_3$ is individually and independently selected from the group comprising Leu, Ile, Val, Met, Trp, Tyr and Phe;
$x_4$ is individually and independently selected from the group comprising Ser, Thr, Ala and Gly; and
$x_5$ is individually and independently selected from the group comprising Gln, Asn In an embodiment the peptide is a peptide of formula Ic:

(SEQ ID NO: 9)
cyclo(Ala-Arg-Ala-Glu-Ser-Asp-Glu-Ala-Arg-Arg-Cys-Tyr-Asn-Asp-Pro-Lys-Cys-Cys-Asp-Phe-Val-Thr-Asn-Arg-Gln). (Ic)

In a preferred embodiment at least one of acidic amino acid residues is replaced by a different amino acid selected from the group comprising acidic amino acids.

In a preferred embodiment at least one of the basic amino acid residues is replaced by a different amino acid selected from the group comprising basic amino acids.

In a preferred embodiment at least one of the aliphatic amino acid residues is replaced by a different amino acid selected from the group comprising aliphatic amino acids.

In a more preferred embodiment at least one Ala amino acid residue is replaced by Glu.

In an embodiment the peptide is a cyclic peptide of formula IIa:

(SEQ ID NO: 10)
Cyclo(Ala-$x_4$-$x_2$-Trp-$x_1$-$x_3$-Gly-$x_4$-Phe-$x_3$-Cys-$x_n$-Gln), (IIa)

whereby n is any integer from 0 to 2, preferably 1 or 2;
whereby $x_1$ is individually and independently selected from the group comprising acidic amino acids;
$x_2$ is individually and independently selected from the group comprising basic amino acids;
$x_3$ is individually and independently selected from the group comprising Leu, Ile, Val, Met, Trp, Tyr and Phe; and
$x_4$ is individually and independently selected from the group comprising Ser, Thr, Ala and Gly.

In a preferred embodiment the peptide is a peptide of formula IIb:

(SEQ ID NO: 11)
cyclo(Ala-Gly-Arg-Trp-Glu-Tyr-Gly-Ser-Phe-Phe-Cys-Glu-Leu-Gln), (IIb)

or a peptide of formula IIc:

(SEQ ID NO: 12)
cyclo(Ala-Gly-Arg-Trp-Glu-Tyr-Gly-Ser-Phe-Phe-Cys-Gln). (IIc)

In a more preferred embodiment at least one of the acidic amino acid residues is replaced by a different amino acid selected from the group comprising acidic amino acids.

In another more preferred embodiment at least one of the basic amino acid residues is replaced by a different amino acid selected from the group comprising basic amino acids.

In another more preferred embodiment at least one of the aliphatic amino acid residues is replaced by a different amino acid selected from the group comprising aliphatic amino acids.

In another more preferred embodiment at least one Ala amino acid residue is replaced by Glu.

In preferred embodiment the peptide is a cyclic peptide of formula IIIa:

(SEQ ID NO: 13)
Cyclo(Ala-$x_4$-$x_2$-$x_3$-$x_1$-$x_3$-$x_4$-$x_4$-$x_3$-$x_3$-Cys-$x_j$-Cys-x-x-x-Pro-x-Cys-Cys-$x_i$-Gln), (IIIa)

whereby i is any integer from 0 to 6, preferably any integer from 1 to 6, more preferably i=6;
whereby j is any integer from 0 to 4, preferably any integer from 1 to 4, more preferably j=4;
whereby $x_1$ is individually and independently selected from the group comprising acidic amino acids;
$x_2$ is individually and independently selected from the group comprising basic amino acids;
$x_3$ is individually and independently selected from the group comprising Leu, Ile, Val, Met, Trp, Tyr and Phe; and $x_4$ is individually and independently selected from the group comprising Ser, Thr, Ala and Gly.

In a more preferred embodiment the peptide is a peptide of formula IIIb:

(SEQ ID NO: 14)
Cyclo(Ala-Gly-Arg-Trp-Glu-Tyr-Gly-Ser-Phe-Phe-Cys-

Glu-Ala-Arg-Arg-Cys-Tyr-Asn-Asp-Pro-Lys-Cys-Cys-

Asp-Phe-Val-Thr-Asn-Arg-Gln), (IIIb)

In another more preferred embodiment at least one of the acidic amino acid residues is replaced by a different amino acid selected from the group comprising acidic amino acids.

In another more preferred embodiment at least one of the basic amino acid residues is replaced by a different amino acid selected from the group comprising basic amino acids.

In another more preferred embodiment at least one of the aliphatic amino acid residues is replaced by a different amino acid selected from the group comprising aliphatic amino acids.

In another more preferred embodiment at least one Ala amino acid residue is replaced by Glu.

In a preferred embodiment the peptide is a linear peptide of formula IVa:

(SEQ ID NO: 15)
Ala-$x_4$-$x_2$-$x_3$-$x_1$-$x_3$-$x_4$-$x_4$-$x_3$-$x_3$-Cys-$x_m$-Cys-x-x-x-Pro-x-

Cys-Cys-$x_n$-Gln, (IVa)

whereby n is any integer from 0 to 6, preferably any integer from 1 to 6, more preferably n=6;
whereby m is any integer from 0 to 4, preferably any integer from 1 to 4, more preferably m=4;
whereby $x_1$ is selected from the group comprising acidic amino acids;
$x_2$ is selected from the group comprising basic amino acids;
$x_3$ is selected from the group comprising Leu, Ile, Val, Met, Trp, Tyr and Phe; and
$x_4$ is selected from the group comprising Ser, Thr, Ala and Gly.

In a more preferred embodiment the peptide is a peptide of formula IVb:

(SEQ ID NO: 16)
Ala-Gly-Arg-Trp-Glu-Tyr-Gly-Ser-Phe-Phe-Cys-Glu-

Ala-Arg-Arg-Cys-Tyr-Asn-Asp-Pro-Lys-Cys-Cys-Asp-

Phe-Val-Thr-Asn-Arg-Gln (IVb)

In a further aspect the present invention is related to cyclic peptides having any of the two following formulae, whereby it is to be acknowledged that both peptides are covered by formula IV but are additional cyclic peptides:

(SEQ ID NO: 1)
Cyclo(Ala-Asp-Glu-Ala-Arg-Arg-Cys-Tyr-Asn-Asp-Pro-

Lys-Cys-Cys-Asp-Phe-Val-Gln)

(SEQ ID NO: 2)
Cyclo(Ala-Arg-Arg-Cys-Tyr-Asn-Asp-Pro-Lys-Cys-Cys-

Asp-Phe-Val-Tyr-Gln)_.

In another more preferred embodiment at least one of the acidic amino acid residues is replaced by a different amino acid selected from the group comprising acidic amino acids.

In another more preferred embodiment at least one of the basic amino acid residues is replaced by a different amino acid selected from the group comprising basic amino acids.

In another more preferred embodiment at least one of the aliphatic amino acid residues is replaced by a different amino acid selected from the group comprising aliphatic amino acids.

In another more preferred embodiment at least one Ala amino acid residue is replaced by Glu.

In an embodiment, in case the peptide is a cyclic peptide, the cyclization occurs by a linkage which is a covalent binding selected from the group comprising S—S linkages, peptide bonds, carbon bonds such as C—C or C=C, ester bonds, ether bonds, azo bonds, C—S—C linkages, C—N—C linkages and C=N—C linkages.

In a preferred embodiment the S—S linkage is formed by two Cys residues of the peptide.

In an alternative preferred embodiment the peptide bond is formed by the $NH_2$ group of the N-terminal amino acid and the COOH group of the C-terminal amino acid.

In another alternative preferred embodiment additional bonds are formed by the side chain of $NH_2$ groups and COOH groups of the constituent amino acids.

The problem underlying the present invention is solved in a second aspect by a composition comprising at least one of the peptides according to the first aspect of the present invention and a carrier.

The problem underlying the present invention is solved in a third aspect by a diagnostic agent comprising at least one of the peptides according to the first aspect of the present invention.

In an embodiment the diagnostic agent is for the detection of anti-β-adrenergic receptor antibodies.

In a preferred embodiment the diagnostic agent comprises at least one further biologically active compound.

The problem underlying the present invention is solved in a fourth aspect by a diagnostic kit for the detection of anti-β1-adrenergic receptor antibodies comprising a peptide according to the first aspect of the present invention or a diagnostic agent according to the third aspect of the present invention.

The problem underlying the present invention is solved in a fifth aspect by a pharmaceutical composition comprising at least one of the peptides according to the first aspect of the present invention and a pharmaceutically acceptable carrier.

In an embodiment the pharmaceutical composition additionally comprises a further pharmaceutically active agent.

In a preferred embodiment the further pharmaceutically active agent is selected from the group comprising a beta receptor blocker, preferably selective β1-adrenergic receptor blockers.

In a more preferred embodiment the further pharmaceutically active agent is selected from the group of selective β1-adrenergic receptor blockers comprising atenolol, metoprolol, nebivolol, and bisoprolol or the non-selective beta blocker carvedilol.

The problem underlying the present invention is solved in a sixth aspect by the use of a peptide according to the first aspect of the present invention, for the manufacture of a medicament.

In an embodiment the medicament is for the treatment and/or prevention of a disease, whereby such disease is selected from the group of heart diseases, comprising infectious and non-infectious heart disease, ischemic and non-ischemic heart disease, inflammatory heart disease and myocarditis, cardiac dilatation, idiopathic cardiomyopathy, idiopathic dilated cardiomyopathy, immune-cardiomyopathy, heart failure, and any cardiac arrhythmia including ventricular and supraventricular premature capture beats.

In a preferred embodiment the disease is idiopathic dilated cardiomyopathy and preferably anti-β-AR antibody-induced dilated immune-cardiomyopathy.

In an embodiment the medicament comprises at least one further pharmaceutically active compound.

In an embodiment the medicament is for the treatment and/or prevention of patients having antibodies against β-adrenergic receptors, preferably β1-adrenergic receptors.

In an embodiment the medicament is for inducing immune tolerance.

The problem underlying the present invention is solved in a seventh aspect by the use of a peptide according to the first aspect of the present invention for the manufacture of a medicament, whereby the medicament is for inducing immune tolerance, preferably by suppression of the production of anti-β-adrenergic receptor antibodies and more preferably by suppression of the production of anti-β1-adrenergic receptor antibodies.

The problem underlying the present invention is solved in an eighth aspect by the use of a peptide according to the first aspect of the present invention for inducing immune tolerance by suppression of the production of anti-β1-adrenergic receptor antibodies through blockade of the antigen-recognition sites of the antibody-producing prae B-cells.

In a still further aspect the problem underlying the present invention is solved by the use of a peptide according to the present invention in a method of diagnosis.

In an embodiment the method is for the diagnosis of idiopathic dilated cardiomyopathy, preferably anti-β-AR antibody-induced dilated immune-cardiomyopathy.

In preferred embodiment the method is a FRET-based method.

Figure 2:
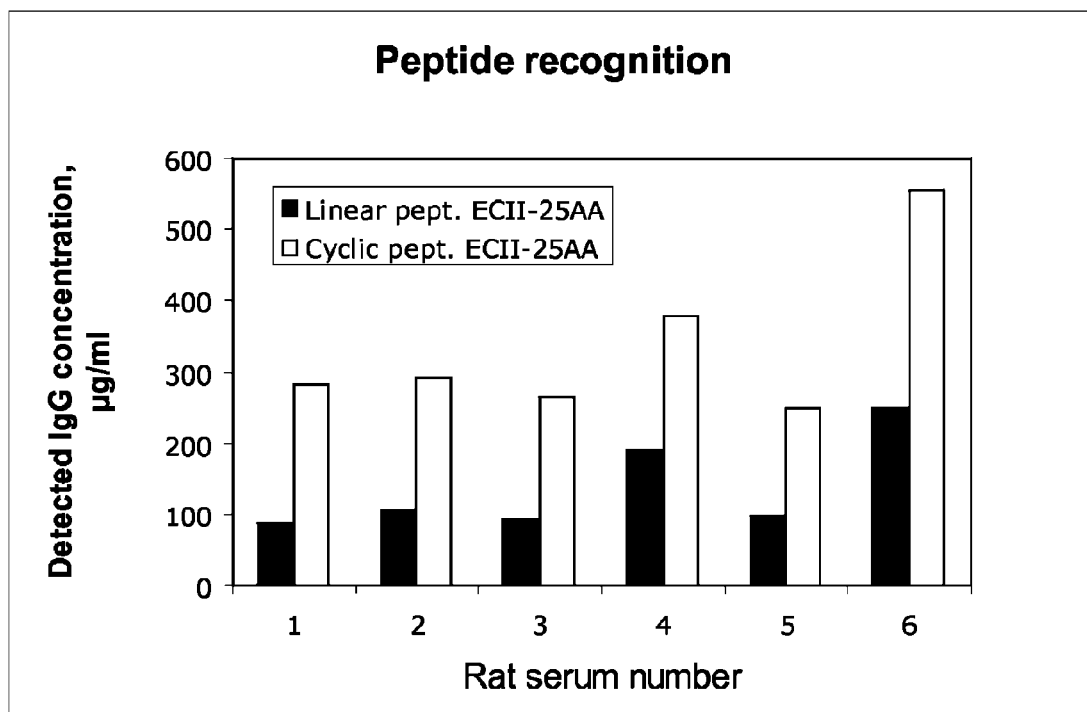

Without wishing to be bound by any theory in the following, the present inventors have surprisingly found that a number of both cyclic as well as linear peptides are, in principle, active as inhibitors of anti-β-adrenergic receptor antibodies, more particularly as inhibitors of anti-β1-adrenergic receptor antibodies. FIG. 2 demonstrates, however, that cyclic peptides are apparently two to three times better recognized (i.e. yield 2-3 times higher DO-values at a same antibody concentration) than linear peptides by anti-β-adrenergic receptor antibodies, more particularly by anti-β1-adrenergic receptor antibodies. In addition, the molecular architecture of a head-to-tail feature together with intramolecular cystein-bridges is thought to give the cyclic peptides hightened resitance to thermal, chemical, and enzymatic degradation in vivo (Ireland D. C. et al. (2006) J. Mol. Biol. 12, 1-14).

Figures 12A, 12B, 12C, 12D:
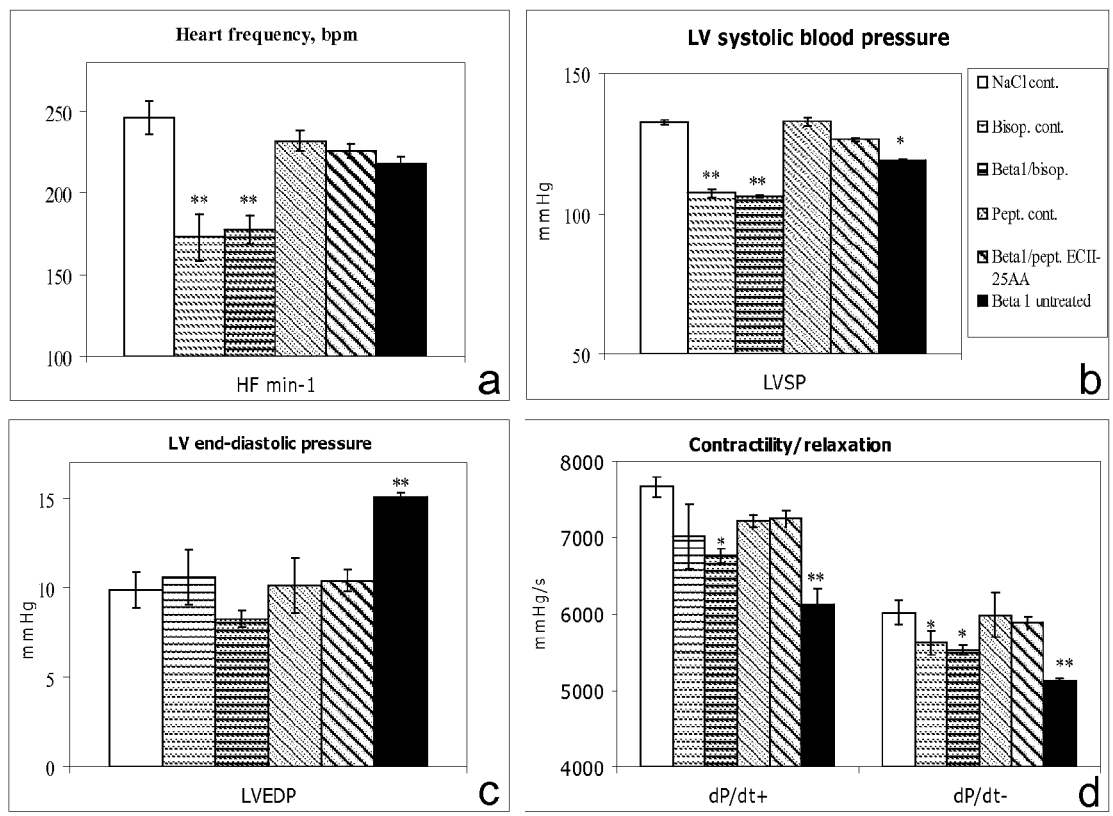
Figures 13A, 13B, 13C, 13D:
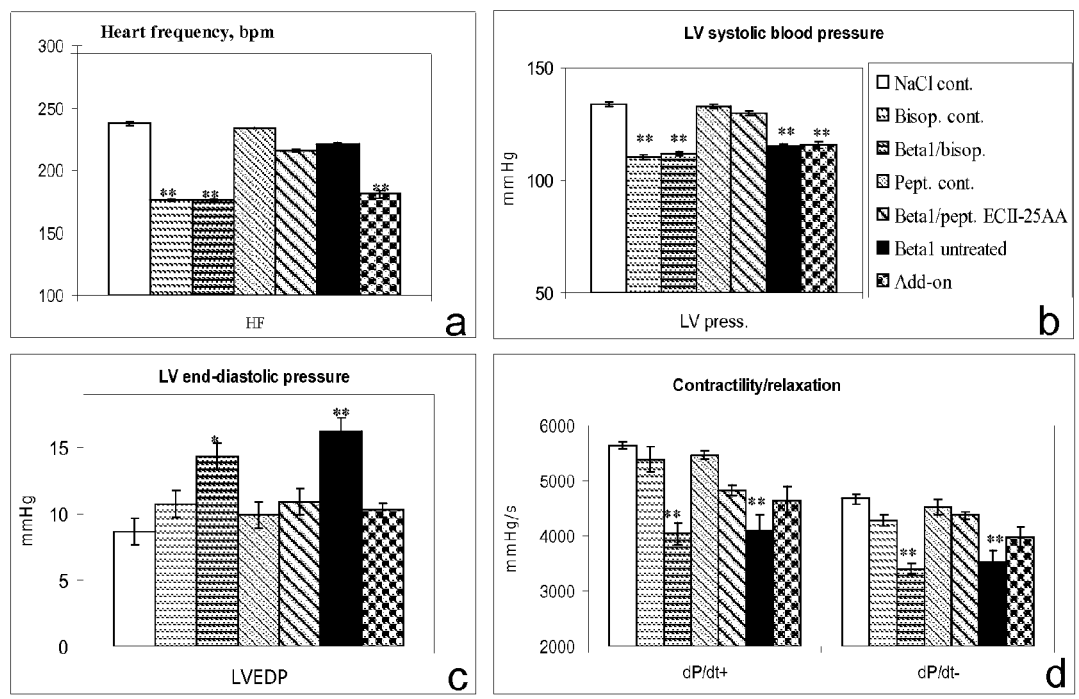

It has to be acknowledged that, as also shown in FIG. 12 and FIG. 13, and described in examples 3 and 4, agents of the prior art, i. e. beta blockers, which may be used for the treatment of dilated cardiomyopathy and other diseases which are caused by stimulatory anti-β1-adrenergic receptor antibodies, such as bisoprolol, significantly reduced both heart rate and blood pressure. In patients suffering from bronchial asthma which represents a contraindication for beta-blocking agents because of a possible induction of bronchospasm or in patients suffering already from a low heart rate and/or a low systemic blood pressure it is thus not possible to use bisoprolol and similarly acting compounds, because a further decrease in heart rate or blood pressure might have severe consequences, including death or the need for surgical procedures, i.e. the implantation of pace makers. In contrast thereto, the peptides of the present invention do not have a negative impact on lung function, heart rate or blood pressure and, therefore, are suitable for the treatment of distinct patient groups which otherwise could not be treated using a beta blocker, i.e. patients who already suffer from bradycardia for whom the use of beta blockers of the prior art such as bisoprolol, is not possible.

Figure 4:
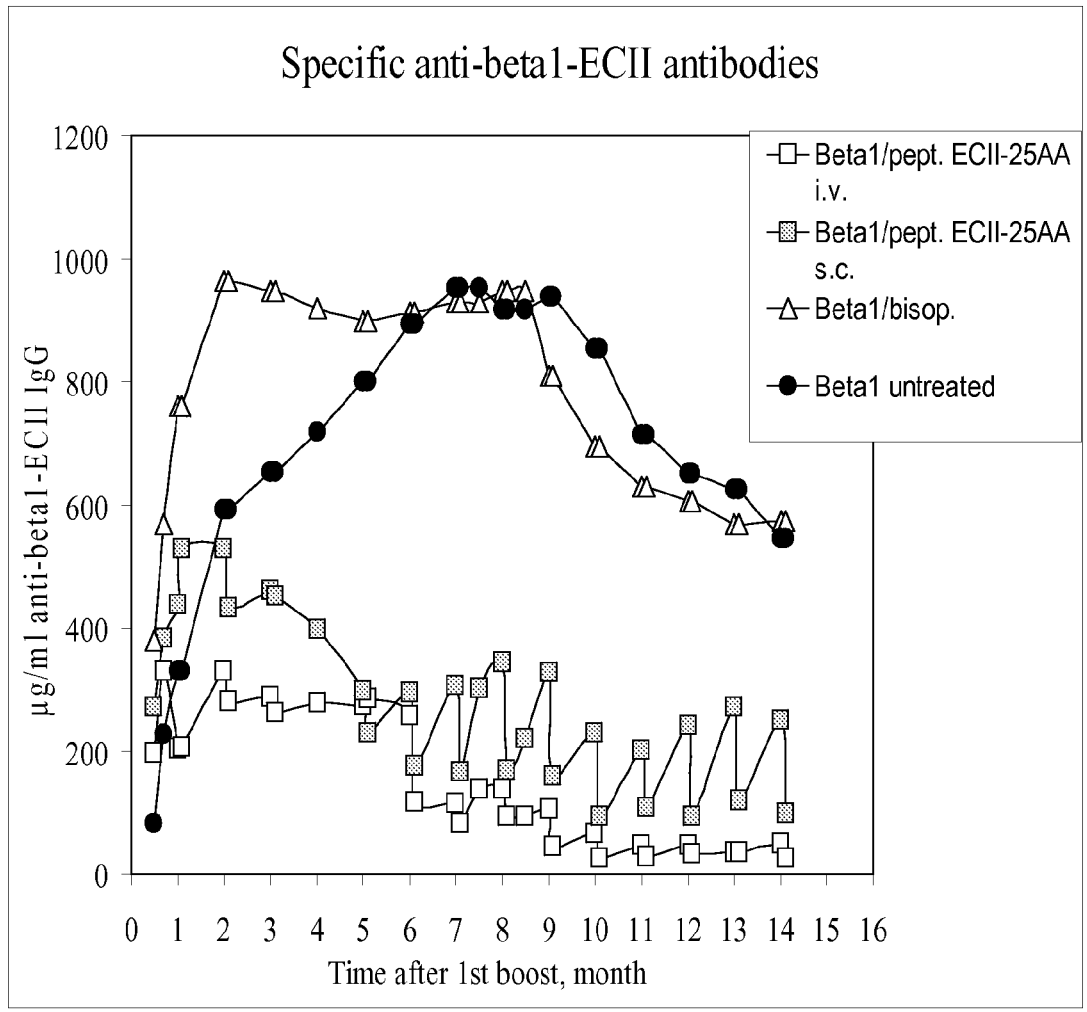
Figure 19:
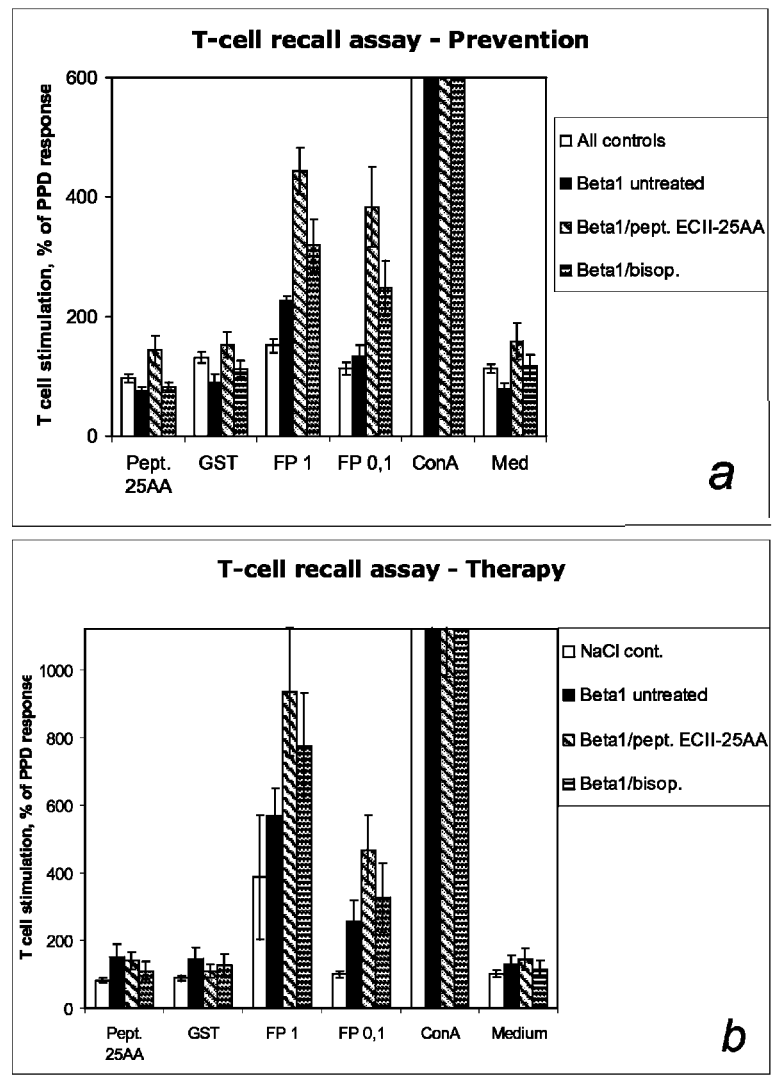
Figures 20A, 20B:
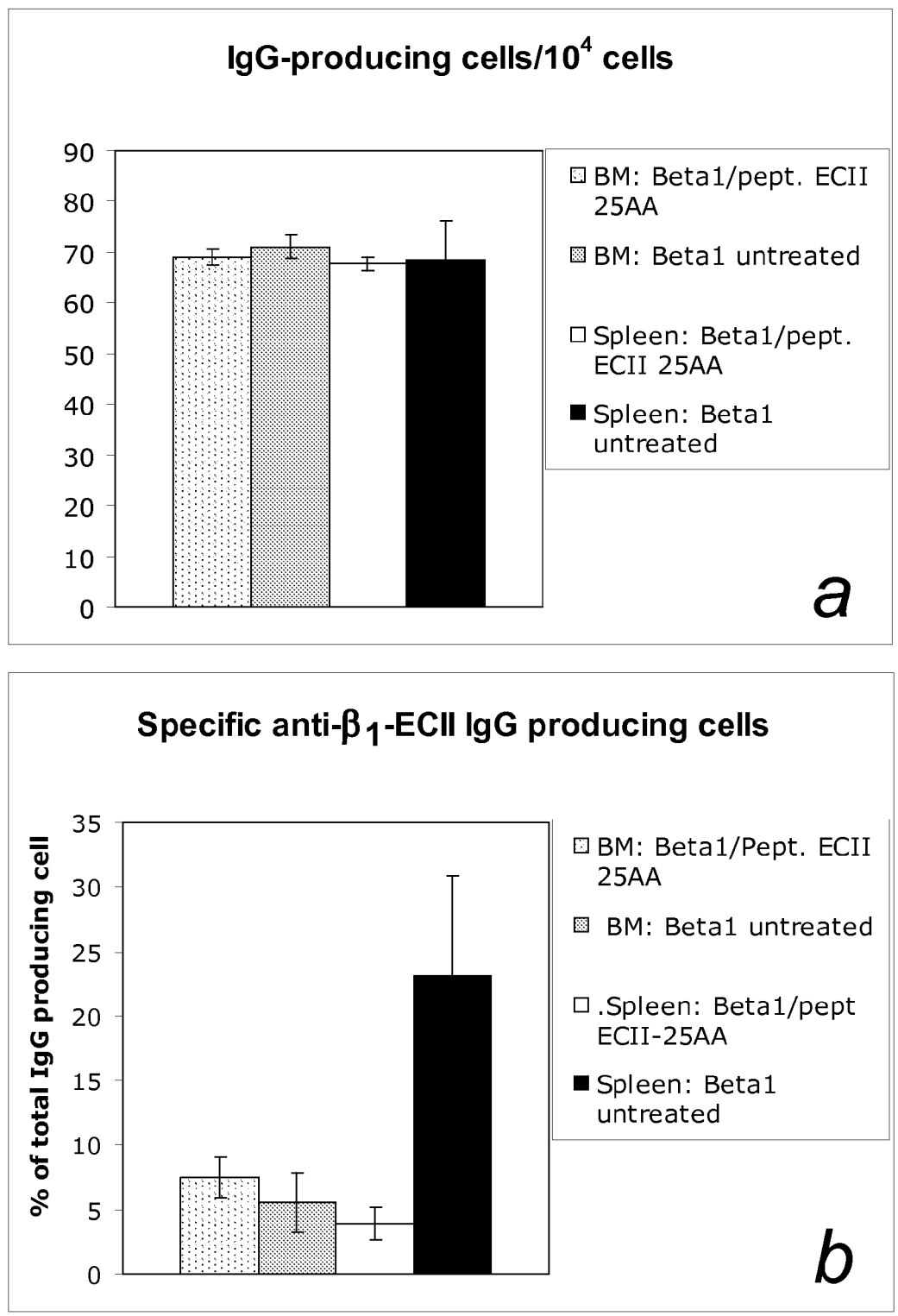

Also, the present inventors have surprisingly found that the peptides according to the present invention obviously act through an additional mechanism different from a capturing of the autoantibodies which activate the β1-adrenergic receptors resulting in, among others, dilated immune-cardiomyopathy and heart failure. Rather, the peptides according to the present invention seem to be suitable to induce immune tolerance since endogeneous production of anti-β1-adrenergic receptor antibodies rapidly decreased and finally stopped within 5-6 months in both prophylactically (FIG. 4) and therapeutically (FIG. 8) treated animals. To the big surprise of the present inventors, within only a few months, significant immune responses were no more observed upon antigen boosts (given every 4 weeks) as shown in FIG. 4 and FIG. 8. This means that some kind of immunological tolerance comparable to hyposensitization with consecutive anergy to the β1-receptor antigen occurred, an effect most likely due to a significant reduction and/or suppression, perhaps even apoptosis, of the anti-β1-EC$_{II}$ producing B-cells. In fact, further analysis of the nature of this immunological tolerance revealed a significant decrease in antigen-specific antibody-producing splenic B-cells in the presence of the cyclic peptide (FIG. 20), whereas regulatory CD4$^+$ T-cells and/or other mechanisms of T-cell induced tolerance do not obviously account for this unresponsive state. FIG. 19 shows representative T-cell recall-assays carried out with CD4$^+$ T-cells isolated from prophylactically (FIG. 19*a*) or therapeutically (FIG. 19*b*) treated anti-β1-EC$_{II}$ antibody-positive immunized animals. The assay was performed according to the publication of Schmidt, J. et al. J. of Neuroimmunology 140, 143-152 (2003). Incubation of isolated CD4$^+$ T-cells with the cyclic peptide, especially the beta 1-ECII 25AA (amino acid) peptide, named as the peptide of formula Ic, neither treatment group resulted in a significant stimulation and subsequently proliferation of the T-cells compared with the dose-dependent cell proliferation reaction seen upon incubation of the T-cells with the β1-ECII/GST fusion protein antigen (FP 1.0 μg/mL or 0.1 μg/mL), or the unspecific T-cell stimulator Concanavalin A (ConA, positive control). In contrast, FIG. 20 shows the results from ELISPOT-assays with splenic B-cells demonstrating that the specifically anti-β1-ECII IgG secreting B-cells were markedly affected and significantly reduced in the spleens of animals treated with 1 mg/kg of the cyclic ECII-25AA peptide of formula Ic, whereas the everlasting anti-β1-ECII specific memory B-cells in the bone marrow of treated animals were not affected by the cyclic peptide. The non-β1-ECII-specific, that is total IgG producing B-cells in the spleen or bone marrow necessary for any kind of humoral response against foreign (including microbial) antigens were not affected at all in animals treated with 1 mg/kg of the cyclic peptide of formula Ic, excluding a general immuno-supressant effect of the cyclic peptide.

It will be understood that for the various peptides of the present invention, a certain flexibility and variability in the primary sequence, i. e. the amino acid sequence is possible as long as the overall secondary and tertiary structure of the respective peptides which is defined by at least some fixed amino acid residues and by their spatial arrangement, is ensured. Moreover the number of amino acids and thus the length of the primary structure appear to be crucial for the biological effects of the various peptides of the present invention. A peptide length equal to or above 26 amino acids (primary structure) is thought to be capable of stimulating directly (that is, without the use of carrier proteins) immunocompetent T-cells and thus may provoke a paradoxal increase in anti-β1-receptor antibody production through T-cell mediated B-cell stimulation (data not shown). Therefore, in the subsequent therapy study using a limited number of supplementary pilot animals we tested shorter peptide variants of the 25 amino acid β1-ECII-peptide, i.e. cyclic peptide-variants comprising either 18 or 16 amino-acids (AA). The generated constructs were: ECII-18AA, cyclo(Ala-Asp-Glu-Ala-Arg-Arg-Cys-Tyr-Asn-Asp-Pro-Lys-Cys-Cys-Asp-Phe-Val-Gln) (SEQ ID NO:1); and ECII-16AA, cyclo(Ala-Arg-Arg-Cys-Tyr-Asn-Asp-Pro-Lys-Cys-Cys-Asp-Phe-Val-Tyr-Gln) (SEQ ID NO:2). Whereas the circulating anti-β1-EC$_{II}$ antibody titers were reduced by about a same extent with either the 25AA cyclic peptide Ic or the 18AA construct (see FIG. 8b)—both yielding also a similar biological efficiency (i.e. reversal of the cardiomyopathic phenotype; see FIG. 10d), the 16AA construct seems to be less effective with regard to both, the continuous reduction of circulating anti-β1-EC$_{II}$ antibody titers (see grey diamonds, FIG. 8b: upon peptide injection the antibody titers remain stable instead of decreasing) and biological efficiency (i.e. ambiguous results in 2 treated rats with one animal having complete reversal of the cardiomyopathic phenotype, the other animal progressive LV dilatation and dysfunction; see FIG. 10d) indicating that a certain length of the cyclic receptor-homologous peptides seems to be necessary to obtain the beneficial biological effects.

The specific peptides in terms of defined amino acid sequences are particularly preferred embodiments over the more general peptides, i.e. the peptides represented by the generic formulae herein.

In accordance therewith, the various generic formulae refer to a basic peptide structure as reflected by formulae I, II, III and IV, whereby more specific formulae and thus peptides being further defined in a less generic manner but still being covered by formulae I, II, III and IV being referred to herein as Ia, Ib, Ic, IIa, IIb, IIIa, IIIb, IVa and IVb, respectively. It will also be understood by the one skilled in the art that the individual amino acid may be replaced by another naturally occurring or synthetic amino acid, preferably if both amino acids belong to the same category of amino acids. In accordance therewith, for example, an acidic amino acid can be replaced by another acidic amino acid, a basic amino acid may be replaced by another basic amino acid and so on. It will also be acknowledged by the ones skilled in the art that one or several of the amino acids forming the peptide of the present invention may be modified. In accordance therewith any amino acid as used herein preferably also represents its modified form. For example, an alanine residue as used herein also comprises modified alanine. Such modifications may, among others, be a methylation or acylation or the like, whereby such modification or modified amino acid is preferably comprised by the present invention as long as the thus modified amino acid and more particularly the peptide containing said thus modified amino acid is still functionally active as defined herein, more particularly functionally active as an inhibitor of β1-adrenergic receptors and even more preferably active in inhibiting the interaction between β1-adrenergic receptors and antibodies, more preferably auto-antibodies directed against β1-adrenergic receptors. Respective assays for determining whether such a peptide, i. e. a peptide comprising one or several modified amino acids, fulfils this requirement, are known to the one skilled in the art and, among others, also described herein, particularly in the example part hereof.

The invention comprises also derivatives of the peptides such as salts with physiologic organic and anorganic acids like HCl, $H_2SO_4$, $H_3PO_4$, malic acid, fumaric acid, citronic acid, tatratic acid, and acetic acid.

As used herein, the sequences of the various peptides are indicated from the N-terminus to the C-terminus, whereby the N-terminus is at the left side and the C-terminus is at the right side of the respective depicted amino acid sequence.

Preferably an acidic amino acid is an amino acid selected from the group comprising Asp, Asn, Glu, and Gln; preferably a basic amino acid is an amino acid selected from the group comprising Arg and Lys; preferably a neutral amino acid is an amino acid selected from the group comprising Gly, Ala, Ser, Thr, Val, Leu, Ile; preferably an aliphatic amino acid is an amino acid which is selected from the group comprising Gly, Ala, Ser, Thr, Val, Leu, Ile, Asp, Asn, Glu, Gln, Arg, Lys, Cys and Met.

As used herein, the expression that one particular amino acid, such as, e. g., a basic amino acid, is replaced by a different amino acid which is selected from a respective particular group of amino acids, such as, e. g., the group comprising basic amino acids, preferably means that the particular amino acid is replaced by another, i. e. different amino acid under the proviso that such different amino acid is part of the respective particular group of amino acids. To the extent indicated herein, this is applicable to each of the particular amino acid and, in principle, each such replacement is independent of any other replacement optionally made in relation to other amino acids forming the respective peptide.

The peptides according to the present invention may be used as a diagnostic agent and for the manufacture of a medicament for the treatment of diseases or may be used in a composition, preferably a pharmaceutical composition, a diagnostic composition and a diagnostic kit, preferably for the detection of anti-β-adrenergic receptor antibodies, more preferably for the detection of anti-β1-adrenergic receptor antibodies. Such diseases are preferably those, where the β1-adrenergic receptor is activated in a non-physiological manner, more particularly is activated by antibodies, more preferably by auto-antibodies which are directed against the β1-adrenergic receptor. More specifically, such diseases comprise, however, are not limited thereto, the group of heart diseases, comprising infectious and non-infectious heart disease, ischemic and non-ischemic heart disease, inflammatory heart disease and myocarditis, cardiac dilatation, idiopathic cardiomyopathy, idiopathic dilated cardiomyopathy, immune-cardiomyopathy, heart failure, and any cardiac arrhythmia including ventricular and supraventricular premature capture. Such pharmaceutical composition may additionally or alternatively also be used for the treatment of patients having antibodies against β-adrenergic receptors, preferably β1-adrenergic receptors. A further subgroup of patients which may be treated by the pharmaceutical composition according to the present invention are those patients suffering from any of the diseases described herein, more particularly the group of heart diseases, comprising infectious and non-infectious heart disease, ischemic and non-ischemic heart disease, inflammatory heart disease and myocarditis, cardiac dilatation, idiopathic cardiomyopathy, idiopathic dilated cardiomyopathy, immune-cardiomyopathy, heart failure, and any cardiac arrhythmia including ventricular and supraventricular premature capture and having at the same time the antibodies directed against β-adrenergic receptors, more preferably antibodies against the β1-adrenergic receptor, whereby in a preferred embodiment the antibodies are auto-antibodies. What is said herein for the pharmaceutical composition applies also to the medicament for the manufacture of which the peptides of the present invention are used. As used herein, compounds and peptides are used in an interchangeable manner herein.

Apart from containing at least one peptide of the present invention, the composition may either comprise two or a plurality of cyclic peptides of the present invention and/or other β-receptor blockers, more particularly β1-adrenergic receptor blockers. Examples therefore are, among others, bisoprolol, metoprolol, atenolol, nebivolol, and carvedilol. This kind of combination provides for protection from antibody-induced selective β1-receptor-downregulation by the peptides (see FIGS. 17 and 18) going along with synergistic β1-receptor upregulation by beta-blockers like bisoprolol or metoprolol (see FIGS. 17 and 18) and ultimately results in a synergistic effect as seen in the animal model (see FIGS. 10, 11, and 13). In accordance therewith, reversal of the cardiomyopathic phenotype occurs only by cyclopeptide-monotherapy or by β-blocker/peptide combination-therapy, but not alone by betablocker monotherapy which has proven to be beneficial in human heart failure and dilated cardiomyopathy, reported in the CIBIS I, II and III studies and the MERIT-HF study.

The pharmaceutical composition typically comprises a carrier, more preferably a pharmaceutically acceptable carrier, excipient or diluent.

For s.c. or i.v. injection, compounds of the invention may be formulated in aqueous solution, preferably in physiologically compatible buffers such as Hank's solution, Ringer's solution, or physiologically saline buffer. For transmucosal and transpulmonal administration, penetrants appropriate to the barrier to be permeated are used in the formulation. Such penetrants are generally known in the art.

The use of pharmaceutical acceptable carriers to formulate the compounds according to the present invention into dosages or pharmaceutical compositions suitable for systemic, i.e. intravenous/intraarterial, or subcutaneous administration is within the scope of the present invention. With proper choice of carrier and suitable manufacturing practice, the compositions of the present invention, in particular those formulated as solutions, may be administered parenterally, such as by intravenous injection. The compounds can be readily formulated using pharmaceutically acceptable carriers well known in the art into dosages suitable for subcutaneous or oral administration. Such carriers enable the compounds according to the present invention to be formulated as tablets, pills, capsules, dragees, liquids, gels, syrups, slurries, suspensions and the like, for oral ingestion by a subject to be treated.

Compounds according to the present invention or medicaments comprising them, intended to be administered intracorporally/intracellularly may be administered using techniques well known to those of ordinary skill in the art. For example, such agents may be encapsulated into liposomes, then administered as described above. Liposomes are spherical lipid bilayers with aqueous interiors. All molecules present in an aqueous solution at the time of liposome formation are incorporated into the aqueous interior. The liposomal contents are both protected from the external microenvironment and, because liposomes fuse with cell membranes, are efficiently delivered near the cell surface. Delivery systems involving liposomes are disclosed in U.S. Pat. No. 4,880,635 to Janoff et al. The publications and patents provide useful descriptions of techniques for liposome drug delivery and are incorporated by reference herein in their entirety.

Pharmaceutical compositions comprising a compound according to the present invention for parenteral and/or subcutaneous administration include aqueous solutions of the active compound(s) in water-soluble form. Additionally, suspensions of the active compounds may be prepared as appropriate oily injection suspensions. Suitable lipophilic solvents or vehicles include fatty oils such as sesame oil or castor oil, or synthetic fatty acid esters, such as ethyl oleate or triglycerides, or liposomes. Aqueous injections suspensions may contain compounds which increase the viscosity of the suspension, such as sodium carboxymethyl cellulose, sorbitol, dextran, or the like. Optionally, the suspension may also contain suitable stabilizers or agents which increase the solubility of the compounds to allow for the preparation of highly concentrated solutions and to allow for a constantly slow release of the substance in the organism.

Pharmaceutical compositions comprising a compound according to the present invention for oral use can be obtained by combining the active compound(s) with solid excipient, optionally grinding the resulting mixture, and processing the mixture of granules, after adding suitable auxiliaries, if desired, to obtain tablets or dragee cores.

Suitable excipients are, in particular, fillers such as sugars, including lactose, sucrose, mannitol, sorbitol, and the like; cellulose preparations, such as, for example, maize starch wheat starch, rice starch, potato starch, gelatin, gum tragacanth, methyl cellulose, hydroxypropylmethyl cellulose, sodium carboxymethyl cellulose, polyvinylpyrrolidone (PVP) and the like, as well as mixtures of any two or more thereof. If desired, disintegrating agents may be added, such as cross-linked polyvinyl pyrrolidone, agar, alginic acid or a salt thereof such as sodium alginate, and the like.

Dragee cores as a pharmaceutical composition comprising a compound according to the present invention are provided with suitable coatings. For this purpose, concentrated sugar solutions may be used, which may optionally contain gum arabic, talc, polyvinyl pyrrolidone, carbopol gel, polyethylene glycol, titanium dioxide, lacquer solutions, suitable organic solvents or solvent mixtures, and the like. Preferably a gastric juice resitent coating such as derivatives of cellulose Aquateric®, HP50® or HP55®, polymer of methacrylic acid and methacrylic acid esters (Eutragid® L, Eutragid® S; retard forms Eutragid® RL and Eutragid® RS or derivatives of polyvinyl are used. Dyestuffs or pigments may be added to the tablets or dragee coatings for identification or to characterize different combinations of active compound doses.

Pharmaceutical preparations comprising a compound according to the present invention which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

The pharmaceutical composition may be present in the range of 10 μg/kg to 100 mg/kg depending on the application form, preferably s.c. or i.v. application every two or four weeks. In the rat 1 mg/kg s.c. or i.v. every other month were sufficient to obtain therapeutic levels of the compounds according to the present invention, with the respective dosage for human preferably being about 1-10 mg/kg i.v. or s.c.

It is within the present invention that the pharmaceutical composition is used for the treatment of any of the diseases and patient groups as defined above including the detection of anti-β-receptor antibodies in these patients by using the aforementioned compounds. Also, the peptides according to the present invention may be used for the preparation of a medicament for the treatment and/or prevention of any of the diseases and patient groups as defined above in connection with the pharmaceutical composition.

Finally, the present invention is related to a method for the treatment of patients suffering from or being at risk to develop a disease as disclosed herein, more particularly heart diseases, comprising infectious and non-infectious heart disease, ischemic and non-ischemic heart disease, inflammatory heart disease and myocarditis, cardiac dilatation, idiopathic cardiomyopathy, idiopathic dilated cardiomyopathy, immune-cardiomyopathy, heart failure, and any cardiac arrhythmia including ventricular and supraventricular premature capture beats, whereby the patient is in need of such treatment and whereby the method comprises administering to said patient a pharmaceutically effective amount of the peptide of the present invention, or the pharmaceutical composition or the medicament disclosed herein. Preferably, a therapeutically effective dose refers to that amount of the active ingredient that produces amelioration of symptoms or a prolongation of survival of a subject which can be determined by the one skilled in the art doing routine testing.

A "patient" for the purposes of the present invention, i.e. to whom a compound according to the present invention or a pharmaceutical composition according to the present invention is administered, includes both humans and other animals and organisms. Thus the compounds, pharmaceutical compositions and methods are applicable to or in connection with both human therapy and veterinary applications including diagnostic(s), diagnostic procedures and methods as well as staging procedures and methods. For example, the veterinary applications include, but are not limited to, canine, bovine, feline, porcine, caprine, equine, and ovine animals, as well as other domesticated animals including reptiles, such as iguanas, turtles and snakes, birds such as finches and members of the parrot family, lagomorphs such as rabbits, rodents such as rats, mice, guinea pigs and hamsters, amphibians, fish, and arthropods. Valuable non-domesticated animals, such as zoo animals, may also be treated. In the preferred embodiment the patient is a mammal, and in the most preferred embodiment the patient is human.

In a further aspect, the present invention is related to a method for diagnosing a patient which can be treated using the peptide, pharmaceutical composition and medicament according to the present invention. Preferably, such method comprises the steps as described in the example part hereof. In one aspect, the present invention is thus related to the use of peptides according to the present invention as a diagnostic or for the manufacture of a diagnostic test. The rationale behind this diagnostic use of the peptides according to the present invention is their interaction with the structures described above and in particular with the anti-β-adrenergic receptor antibodies.

So far, the definition of antibody-positivity depends on highly divergent screening methods such as, e.g., ELISA with receptor peptides, Western blotting of heart tissues, functional assays with neonatal rat cardiomyocytes, or detection by surface plasmon resonance. Until now, this issue has not been solved satisfactorily.

One approach for using the peptides according to the present invention as a diagnostic and in a diagnostic method, respectively, is a three-step screening procedure comprising performing an ELISA with the peptides according to the present invention as well as determining immunofluorescence and determining cAMP responses in cells expressing native human beta-AR. It is to be acknowledged that each and any of the aforementioned steps can as such be preformed for the detection of said antibodies using the peptides according to the present invention. A large number of heart failure patients may thus be screened for functionally active anti-beta1-Abs. In connection with such diagnostic method the definition of functionally active anti-beta1-Abs is preferably based on their effects on receptor-mediated signalling, that is, their effects on cellular cAMP levels and on the activity of the cAMP-dependent protein kinase (PKA). Cyclic AMP is an universal second messenger of many G protein-coupled receptors including the beta-adrenergic receptor family. It exerts its effects via PKA, cAMP-gated ion channels, phosphodiesterases, and exchange proteins directly activated by cAMP, known as Epac1 and 2. The prior art describes several fluorescence methods for measuring cAMP in intact cells which can all be used in connection with the diagnostic method of the present invention. Fluorescence resonance energy transfer (FRET) between green fluorescent protein (GFP) variants fused to the regulatory and catalytic subunits of PKA has been described to study the spatio-temporal dynamics of cAMP in neurons (Hempel C M, Vincent P, Adams S R, Tsien R Y, Selverston A I. Nature 1996, 384:113-114) or cardiac myocytes (Zaccolo M, Pozzan T., Science 2002, 295:1711-1715).

More recently, single chain fluorescence indicators have been described in the art which are characterized by having an enhanced cyan (CFP) or yellow fluorescent protein (YFP) directly fused to the cAMP-binding domain of Epac-proteins, which allowed to achieve a higher sensitivity and better temporal resolution of the cAMP measurements. Such system is, among others described in WO2005/052186 the disclosure of which is incorporated herein by reference in its entirety. Such system can be used in connection with any diagnostic procedure using the peptides according to the present invention. Also such system can be used for, however is not limited thereto, analyzing the prevalence of functionally active anti-beta1-Abs. Preferably such diagnostic method is applied to a cohort of previously antibody-typed DCM patients or any individual to be assessed insofar or any individual suspected of suffering from any of the diseases described herein or being at risk to suffer therefrom. In a further step of the diagnostic method and screening method, the ability of beta-blockers to inhibit anti-beta1-Ab-induced receptor activation can be assessed and determined, respectively.

The afore described assay which is a FRET-based method as described in WO 2005/052186 making use of the peptides according to the present invention is advantageous insofar as it is simpler, less time consuming, and at the same time discloses or identifies all DCM patients previously considered anti-beta1-ECII-positive. This embodiment of a FRET based method of diagnosing making use of one or several of the peptides according to the present invention is based on detecting antibody-induced increases in cAMP. This second messenger most likely accounts for the harmful effects provoked by activating anti-beta1-Abs. Therefore, it is advantageous that this method, which is preferably used as a diagnostic method, and which quantifies antibody-induced cAMP signals allows to differentiate between functional anti-beta1-Ab-classes. In fact, by applying this method a previously undetected patient population characterized by the presence of "low" activating autoantibodies presumably targeting a different receptor domain, has been identified. Additionally, this method suggests that these classes are preferably directed against different epitopes of the receptor. Taken together, screening by Epac-FRET appears to represent a very sensitive single step approach, allowing to detect different kinds of activating antibodies directed against the human beta1-AR. Therefore, the present invention is also related to the use of one or several of the peptides according to the present invention for use in an Epac-FRET assay. More preferably such Epac-FRET assay is used for diagnosis, even more preferably for the diagnosis of patients suffering from or suspected of suffering from any of the disease described herein.

A further finding underlying the present invention is that functional anti-beta 1-Abs were detected in almost two thirds of patients with DCM—about half of them "high" activator IgG, it means directed against beta 1-ECII, and about another half "low" activator IgG, it means directed against beta 1-ECI. Insofar, these patients define groups of patients which can be diagnosed and treated, respectively, with the peptides according to the present invention. Mortality curves for the two FRET-classified populations demonstrated that "low" activator IgG patients do not significantly differ in mortality from DCM patients without activating auto-antibodies, whereas "high" activator IgG patients have a significantly higher mortality. Thus, anti-beta 1-Abs directed against beta 1-ECII are clinically particularly relevant and are, therefore, a particularly preferred marker and target, respectively, in or subject to the diagnostic methods disclosed herein. The capability of the FRET-based approach which is a preferred method of diagnosis according to the present invention to differentiate between prognostically distinct anti-beta1-Abs in heart failure, preferably due to DCM, provides for the clinical relevance of this method.

In a still further aspect the present invention is related to a diagnostic agent. Such diagnostic agent consists of or comprises at least one peptide of the present invention. Preferably the diagnostic agent consists of a peptide of the present invention, whereby the peptide preferably comprises a label. Such label may be selected from the group comprising radioactive labels and fluorescent labels. Respective labels are known to the ones skilled in the art. Typically, the peptide is the part of the diagnostic agent conferring specific binding characteristics to the diagnostic agent, preferably binding to anti-$\beta$1-adrenergic receptor antibodies, whereas the label confers the signalling characteristics to the diagnostic agent.

The diagnostic agent may comprise, apart from the labelled or unlabelled peptide of the present invention, a further biologically active compound. Such further biologically active compound, in a preferred embodiment, is a means to confer signalling characteristics to the diagnostic agent, particularly in case the peptide of the present invention is unlabelled. For example, the further biologically active compound can be an antibody, preferably a monoclonal antibody, and more preferably a labelled antibody specifically binding to a peptide of the present invention or to a complex consisting of a peptide of the present invention and an anti-$\beta$-adrenergic receptor antibody, preferably an anti-$\beta$1-adrenergic receptor antibody.

The kit in accordance with the present invention comprises at least a feature which is selected from the group comprising a peptide of the present invention and a diagnostic agent according to the present invention. In an embodiment the kit further comprises an instruction leaflet, and/or a buffer for use in the application of the kit, and/or at least one reaction vessel for carrying out the detection reaction for which the kit is or is to be used. In a further embodiment, some or all of the reagents used in connection with the application of said kit are present as portions useful in carrying out the reaction(s) for which the kit is to be used.

In preferred embodiments, the following abbreviations shall have the following meanings: Ab or ab: antibody, Abs or abs: antibodies, AR: adrenergic receptor, EC extracellular and AA amino acid.

The present invention will now be further illustrated by the following figures and examples, from which further advantages, features and embodiments may be taken, whereby.

FIG. 1 shows different therapeutic approaches for the treatment of autoantibody-induced dilated immune-cardiomyopathy. The beta-adrenergic receptor-mediated signaling cascade (depicted are the beta-receptor (beta-AR), the G protein (subunits Gs-alpha and -beta, gamma, and the adenylatcyclase (AC)) and their blockade by a beta blocking agent (left panel) or a cyclic peptide (right panel) is demonstrated. One therapeutic mode of action of the peptide is illustrated, that is capturing of the antibodies against the beta1-adrenergic receptor by the cyclic peptide.

FIG. 2 demonstrates the difference in recognition of the linear versus the cyclic 25AA beta 1-ECII peptide, namely peptide Ic, by specific anti-beta1-ECII receptor-antibodies generated in CrlBR Lewis rats using beta1-ECII/GST as antigen. Columns represent the amount of specific anti-beta 1-ECII antibodies bound to either linear (black) or cyclic (white) beta 1-ECII-peptides. Representative results obtained from six different rats are shown.

Figure 3:
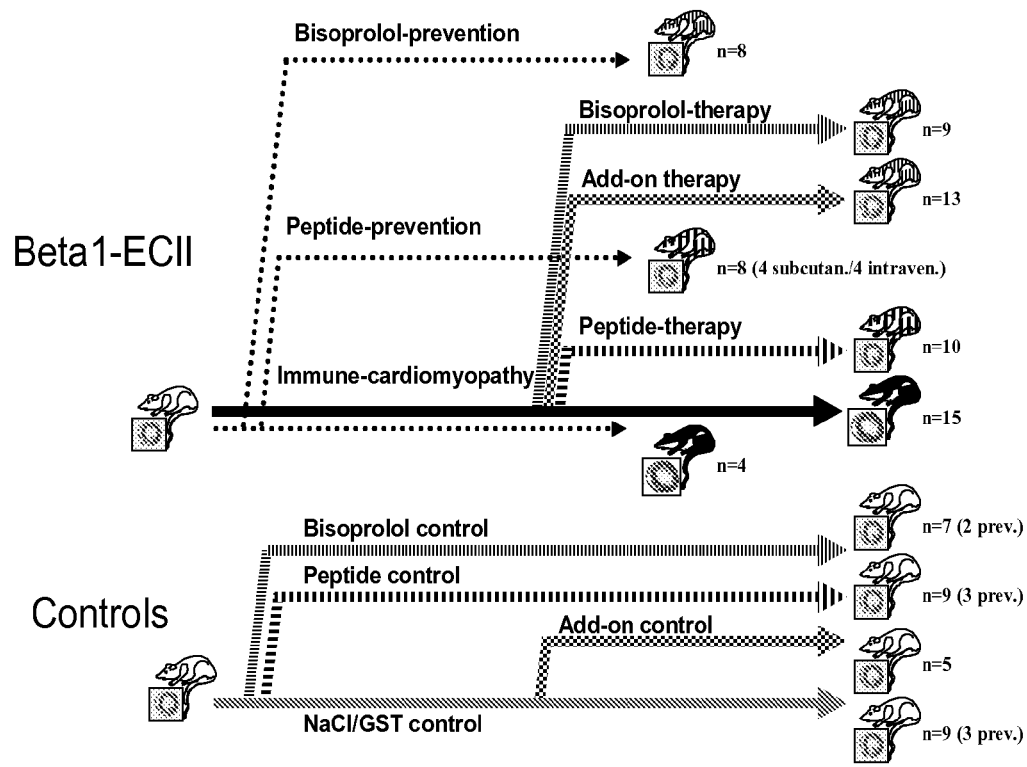

FIG. 3 is a schematic representation of the various experimental set ups for the prevention and/or therapy of immune cardiomyopathy, whereby "immune cardiomyopathy" means immunized non-treated animals (cardiomyopathic phenotype); "bisoprolol-prevention/-therapy" means immunized animals treated in a prophylactic or therapeutic manner using bisoprolol; and "peptide-prevention/-therapy" means immunized animals treated using a peptide according to the present invention; "add-on" therapy means parallel treatment of immunized animals with bisoprolol (15 mg/kg, administered orally) and the cyclic peptide Ic (1 mg/kg, intravenously). Lewis CrlBR rats were used as animals. The numbers of animals used in the various experimental branches are indicated and the end of each treatment arm; data shown in all following figures refer to these numbers; bisoprolol controls were treated with 15 mg/kg administered orally, peptide controls with 1 mg/kg i.v. or s.c. and NaCl/GST controls s.c.

FIG. 4 is a diagram indicating the titer course of specific anti-1-ECII antibodies in the prevention arm of the study, whereby "Beta1 untreated" means immunized animals being not treated, "Beta1/bisop." means immunized animals being prophylactically treated using bisoprolol in a dosage of 15 mg/kg, and "Beta1/pept. ECII-25AA i.v." and "Beta1/pept. ECII-25AA s.c." means immunized animals being prophylactically treated intravenously (i.v.) or subcutaneously (s.c.) using the peptide Ic in dosage of 1 mg/kg each.

Figure 5:
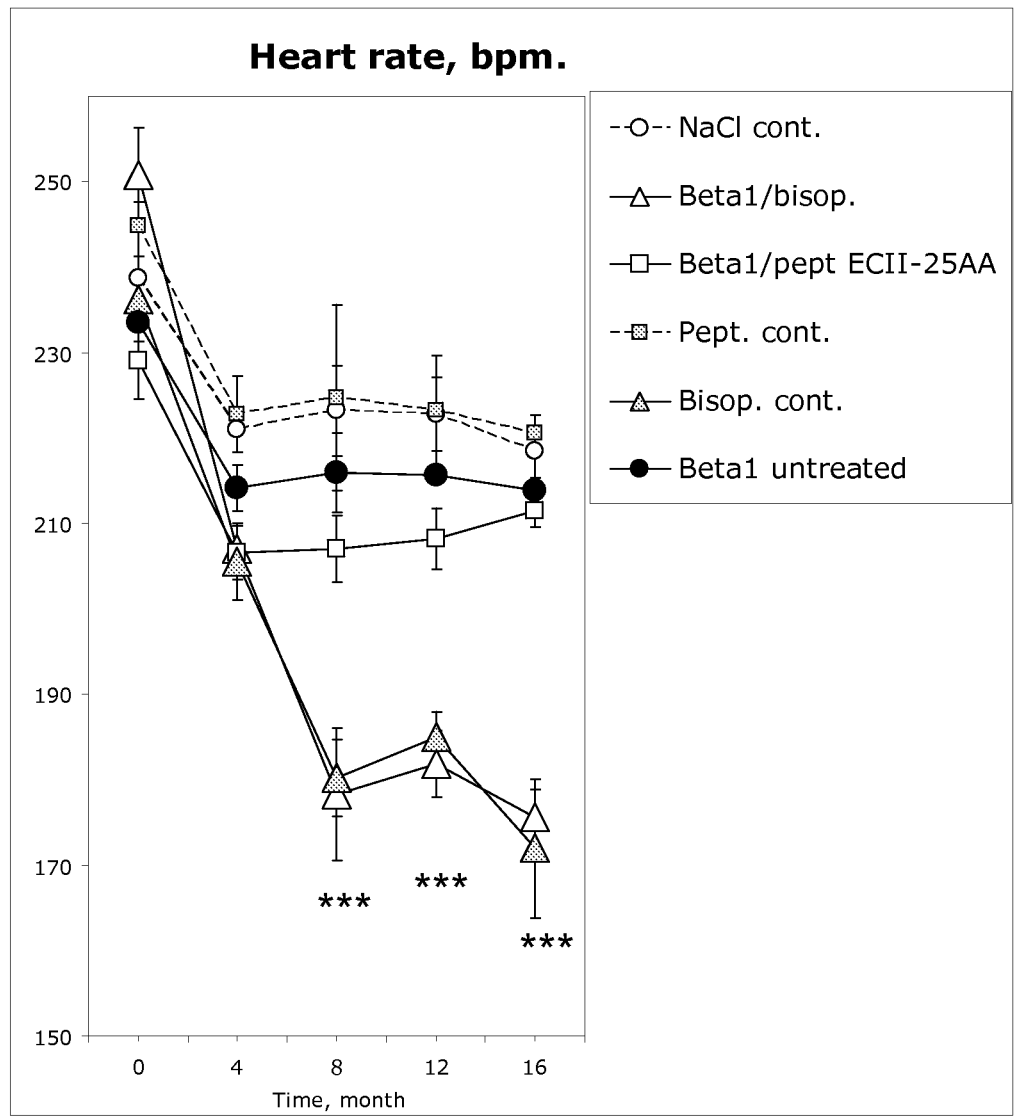

FIG. 5 is the time course of the heart rate of animals in the prevention arm of the study, whereby "Beta1 untreated" means immunized not treated animals, "Beta1/bisop." means immunized animals prophylactically treated with bisoprolol, the first 4 months 10 mg/kg then 15 mg/kg, "Beta1/pept ECII-25AA" means immunized animals prophylactically treated with the peptide Ic (1 mg/kg; n=4 subcutanously, n=4 intravenously); and "Cont." means corresponding control groups; "bpm" means beats per minute.

Figure 6:
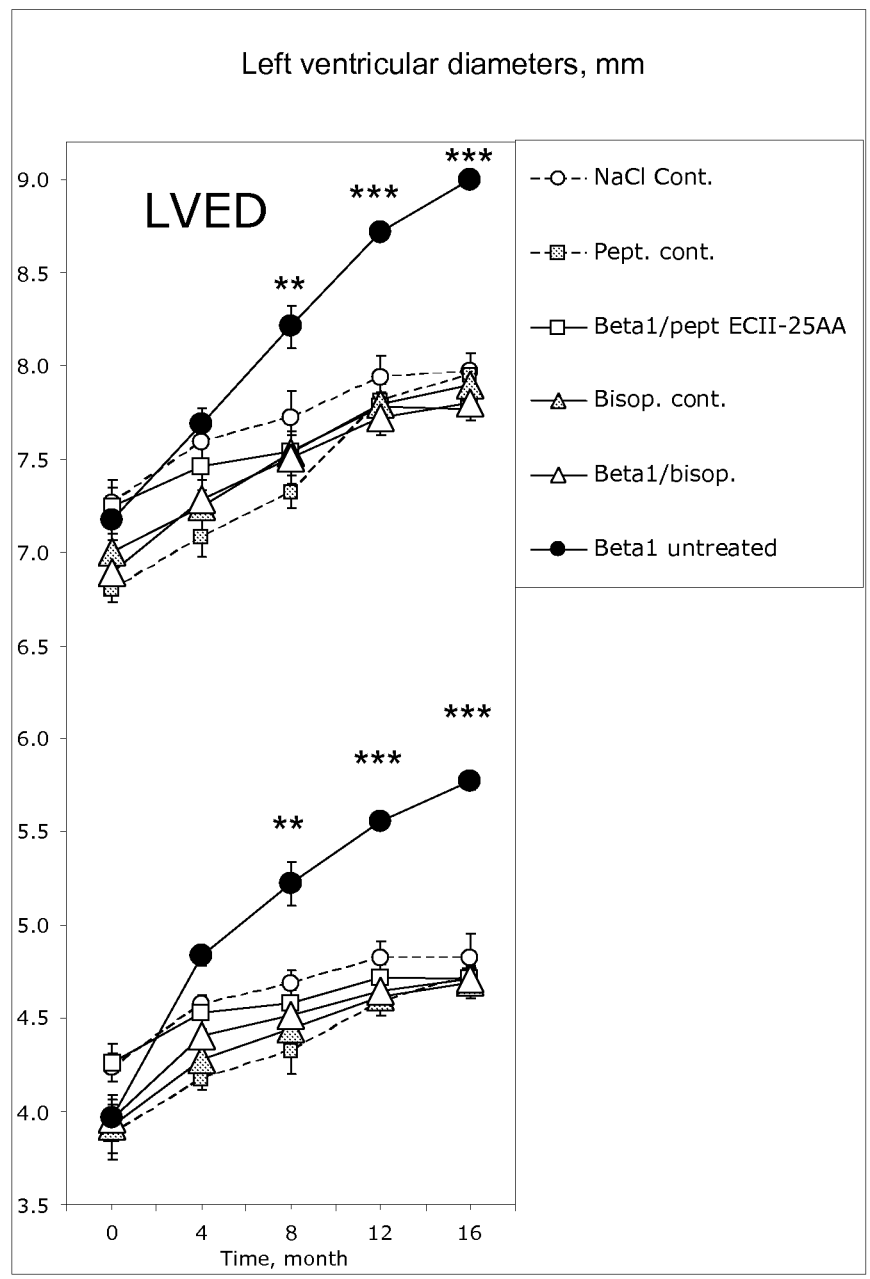

FIG. 6 is a diagram showing the internal end-systolic and end-diastolic left ventricular diameters as determined by echocardiography (echocardiographic system: Vivid Seven, GE Vingmed Ultrasound, Horten, Norway, equipped with a 10-12.5 MHz transducer), whereby "Beta1 untreated" means immunized not treated animals, "Beta1/bisop." means immunized animals prophylactically treated with bisoprolol, "Beta1/pept. ECII-25AA" means immunized animals prophylactically treated with the 25 AA peptide Ic; and "Cont." means corresponding control groups, whereby LVES/LVED is left ventricular end-systolic diameter/left ventricular end-diastolic diameter.

Figure 7:
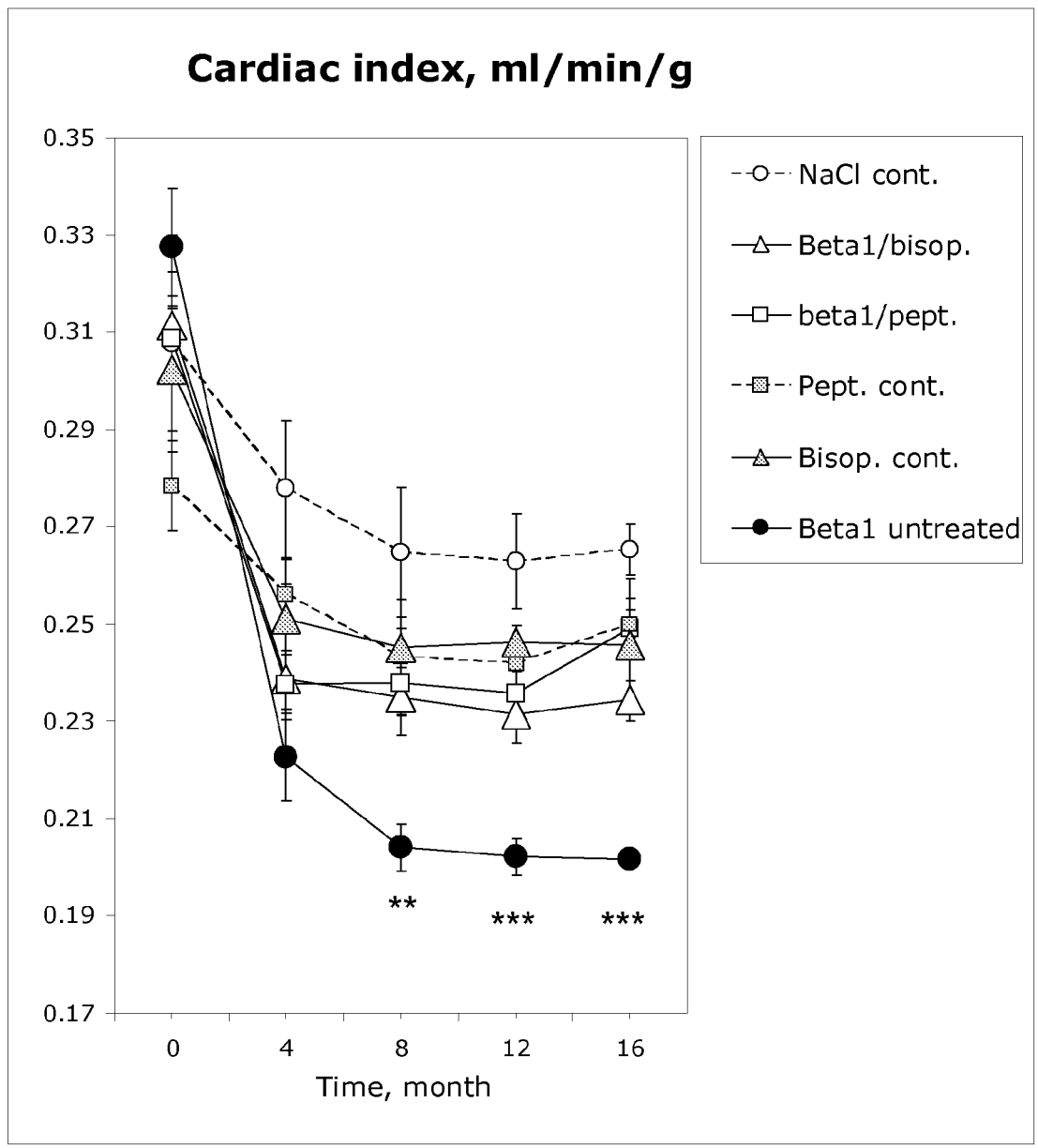

FIG. 7 is a diagram showing the "Cardiac index" in ml/min/g (body weight) as determined by echocardiography (echocardiographic system see above), whereby "Beta1 untreated" means immunized not treated animals, "Beta1/bisop." means immunized animals prophylactically treated with bisoprolol, "Beta1/pept." means immunized animals prophylactically treated with the beta 1-ECII 25AA peptide Ic; and "Cont." means corresponding control groups.

Figures 8A, 8B:
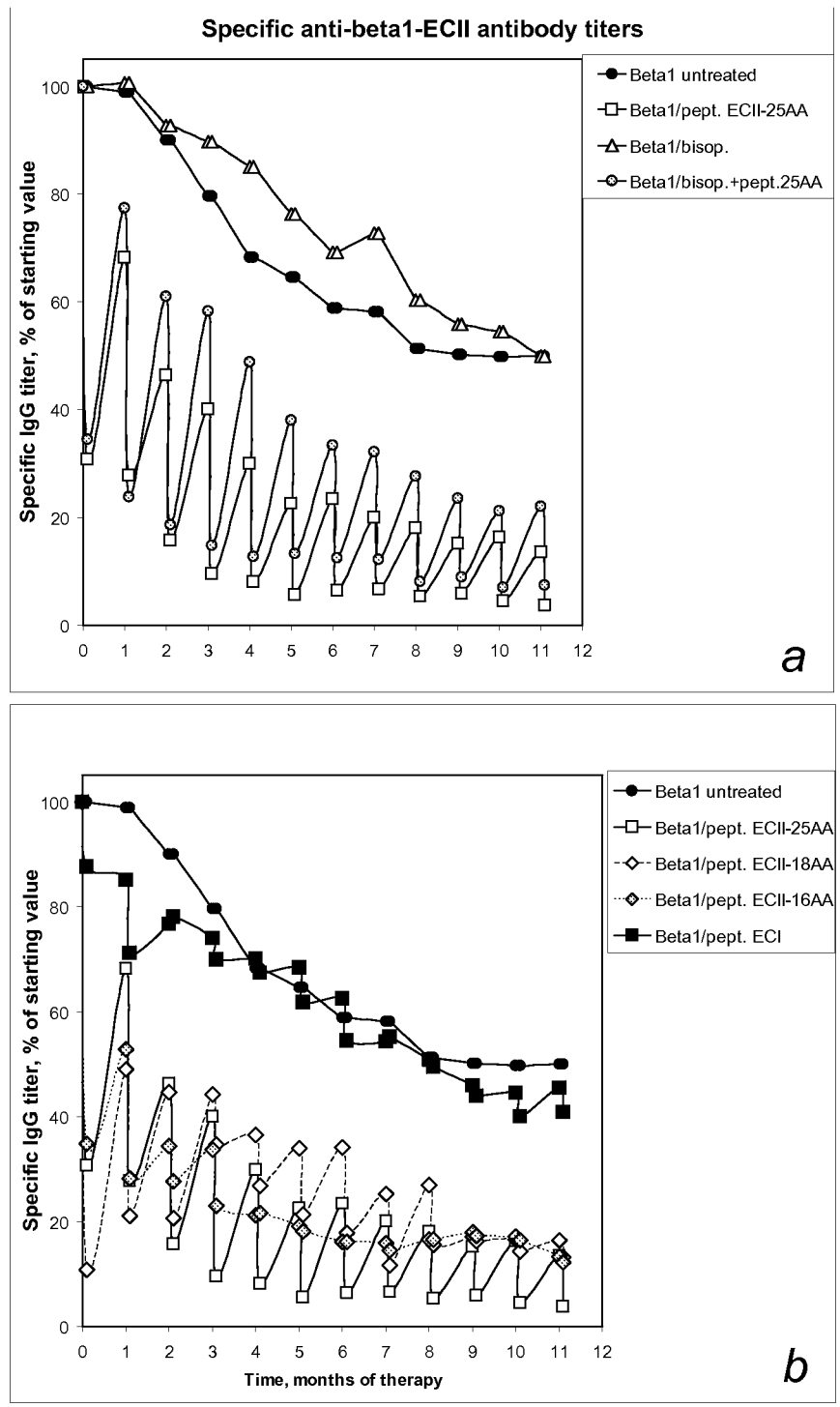

FIG. 8a is a diagram indicating the titer course of specific anti-ECII antibodies in the therapy arm of the study, given as % of the respective titers at the time point treatment was initiated ("starting value"), whereby "Beta1 untreated" means immunized anti-1-positive cardiomyopathic not treated animals, "Beta1/bisop." means immunized anti-1-positive cardiomyopathic animals treated with bisoprolol (15 mg/kg, orally), "Beta1/pept. ECII-25AA" means immunized anti-1-positive cardiomyopathic animals treated with the 25AA peptide Ic in a dosage of 1 mg/kg intravenously, and "Beta1/bisop.+pept.25AA" means treatment with a combination of bisoprolol and the 25AA peptide Ic. Therapy was started after 8 months of regular (1× monthly) immunization. Monthly immunization was continued under therapy.

FIG. 8b is a diagram comparing the titer course of specific anti-ECII antibodies dependent on the different peptide variants used in the therapy arm of the study, whereby 25AA means the cyclic peptide Ic, 18AA means the shorter 18 amino-acid variant, and 16AA the shorter 16 amino-acid variant of the peptide. "Beta1 untreated" means immunized anti-1-positive cardiomyopathic not treated animals, "Beta1/pept. ECI" means immunized anti-1-positive cardiomyopathic animals treated with a peptide corresponding to the first extracellular receptor loop (1 mg/kg, intravenously, negative control—supposed and shown to not affect the anti-ECII antibody-titers), "Beta1/pept. ECII-25AA, ECII-18AA, ECII-16AA" means immunized anti-1-positive cardiomyopathic animals treated with the 25AA-, 18AA-, or 16AA-peptide, respectively.

Figure 9:
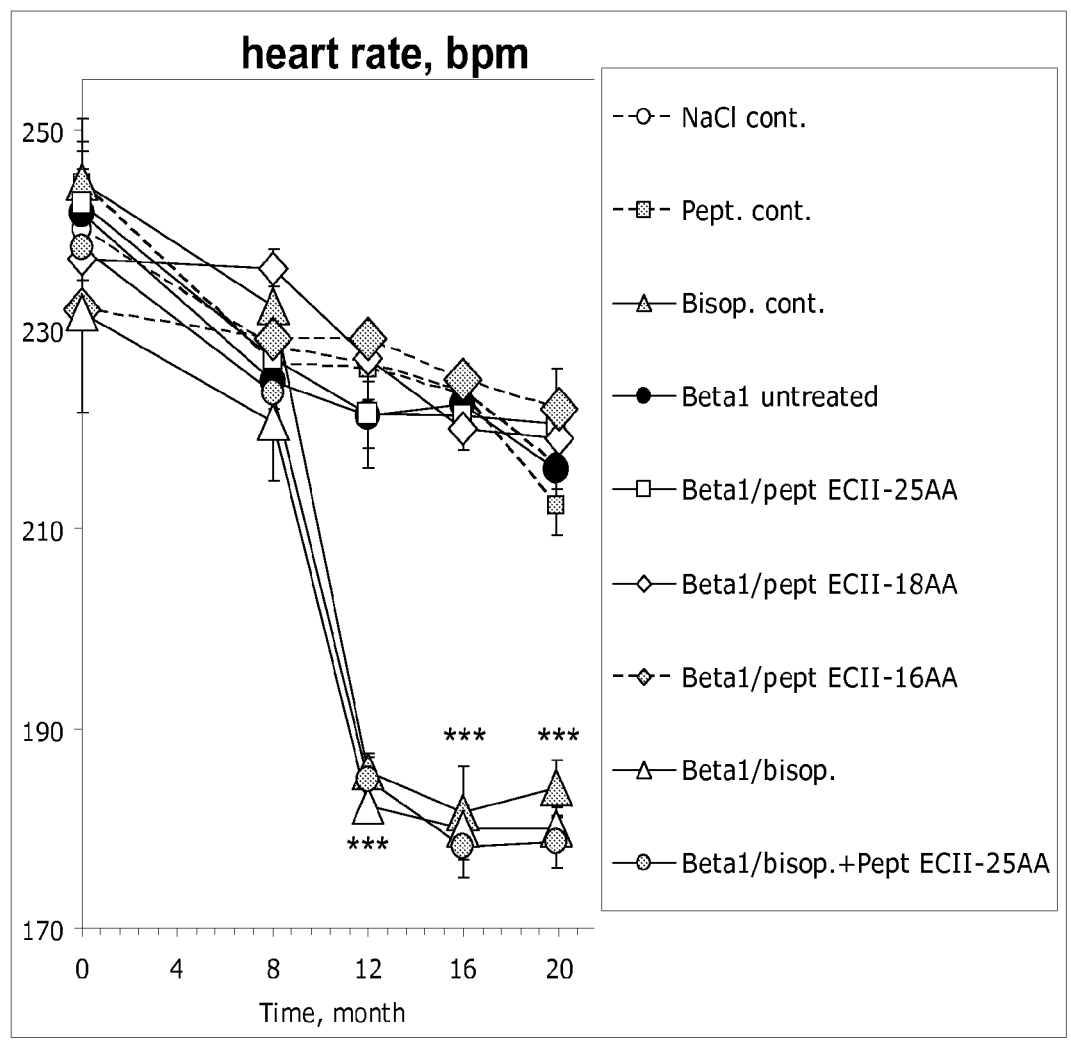

FIG. 9 is a diagram indicating the heart rate of the animals from the therapy study, whereby "Beta1 untreated" means immunized anti-1-positive cardiomyopathic not treated animals; "Beta1/bisop." means immunized anti-1-positive immunized cardiomyopathic animals treated with bisoprolol (15 mg/kg) after 8 months; "Beta1/pept ECII-25AA, -18AA, -16AA" means immunized anti-1-positive cardiomyopathic animals treated with 1 mg/kg of the 25AA-, 18AA-, or 16AA-peptide, respectively, after 8 months of immunization, and "Cont." means the respective control groups; "Beta1/bisop.+Pept ECII-25AA" means immunized anti-1-positive cardiomyopathic animals treated with a combination of bisoprolol and the beta 1-ECII 25AA peptide after 8 months.

FIG. 10 is partitioned in 4 diagrams, each showing the time course of internal end-systolic and end-diastolic left ventricular diameters as determined by echocardiography, whereby "Beta1 untreated" means immunized anti-1-positive cardiomyopathic not treated, and "Cont." not immunized control animals plotted together with (a) immunized anti-1-positive cardiomyopathic animals treated with 15 mg/kg bisoprolol ("Beta1/bisop."), not immunized control animals treated with bisoprolol ("Bisop. cont."), (b) immunized anti-1-positive cardiomyopathic animals treated with 25AA cyclic peptides, namely peptide Ic, (1 mg/kg, starting 8 months after immunization; "Beta1/pept ECII-25AA"), and not immunized control animals injected with the same peptide ("Pept. cont."), (c) immunized anti-1-positive cardiomyopathic animals treated with bisoprolol ("Beta1/bisop."), 25AA cyclic peptides ("Beta1/pept ECII-25AA"), or a combination of bisoprolol/cyclic peptide (Beta1/bisop.+Pept. ECII-25AA), and (d) immunized anti-1-positive cardiomyopathic animals treated with ECII-25AA/18AA/16AA peptides, or the ECI-peptide, namely petide IIb or IIc, respectively ("Beta1/pept ECII-25AA, ECII-18AA, ECII-16AA", or "Beta1/pept ECI"). LVES means left ventricular end-systolic diameter and LVED means left ventricular end-diastolic diameter.

FIG. 11 is partitioned in 4 diagrams depicting the time course of the "Cardiac index" in ml/min/g (body weight) as determined by echocardiography (echocardiographic system see above), whereby "Beta1 untreated" means immunized anti-1-positive cardiomyopathic not treated, and "Cont." not immunized control animals plotted together with (a) anti-1-positive immunized animals treated with 15 mg/kg bisoprolol ("Beta1/bisop."), not immunized control animals treated with bisoprolol ("Bisop. cont."), (b) immunized anti-1-positive cardiomyopathic animals treated with 25AA cyclic peptides, namely peptide Ic, (1 mg/kg, starting 8 months after immunization; "Beta1/pept ECII-25AA"), and not immunized control animals injected with 25AA cyclic peptides ("Pept. cont."), (c) immunized anti-1-positive cardiomyopathic animals treated with bisoprolol ("Beta1/bisop."), 25AA cyclic peptides ("Beta1/pept ECII-25AA"), or a combination of bisoprolol/cyclic peptide (Beta1/bisop.+Pep. ECII-25AA) after 8 months, and (d) immunized anti-1-positive cardiomyopathic animals treated with ECII-25AA/18AA/16AA peptides, or the beta 1-ECI-peptide preferably peptide IIb and IIc, respectively ("Beta1/pept ECII-25AA, ECII-18AA, ECII-16AA", or "Beta1/pept ECI" (negative control)).

FIG. 12 shows hemodynamic parameters obtained in the prevention study, in detail the heart frequency (a), the LV systolic blood pressure (b), the LV end-diastolic pressure (c) and contractility/relaxation (d), whereby "Beta1 untreated" means immunized not treated animals, "Beta1/bisop." means immunized animals prophylactically treated with bisoprolol, "Beta1/pept ECII-25AA" means immunized animals prophylactically treated with the cyclic beta 1-ECII 25AA peptide Ic and "Cont." means respective control groups.

FIG. 13 shows hemodynamic parameters obtained in the therapy study, in detail the heart frequency (a), the LV systolic blood pressure (b), the LV end-diastolic pressure (c) and contractility/relaxation (d), whereby "Beta1 untreated" means immunized anti-beta1-positive cardiomyopathic not treated animals, "Beta1/bisop." means immunized anti-1-positive cardiomyopathic animals therapeutically treated with bisoprolol, "Beta1/pept ECII-25AA" means immunized anti-1-positive cardiomyopathic animals therapeutically treated with the cyclic beta1-ECII 25AA peptide Ic, or with a combination of bisoprolol/cyclic peptide ("Add-on") after 8 months of immunization, and "Cont." means the respective control groups.

Figure 14:
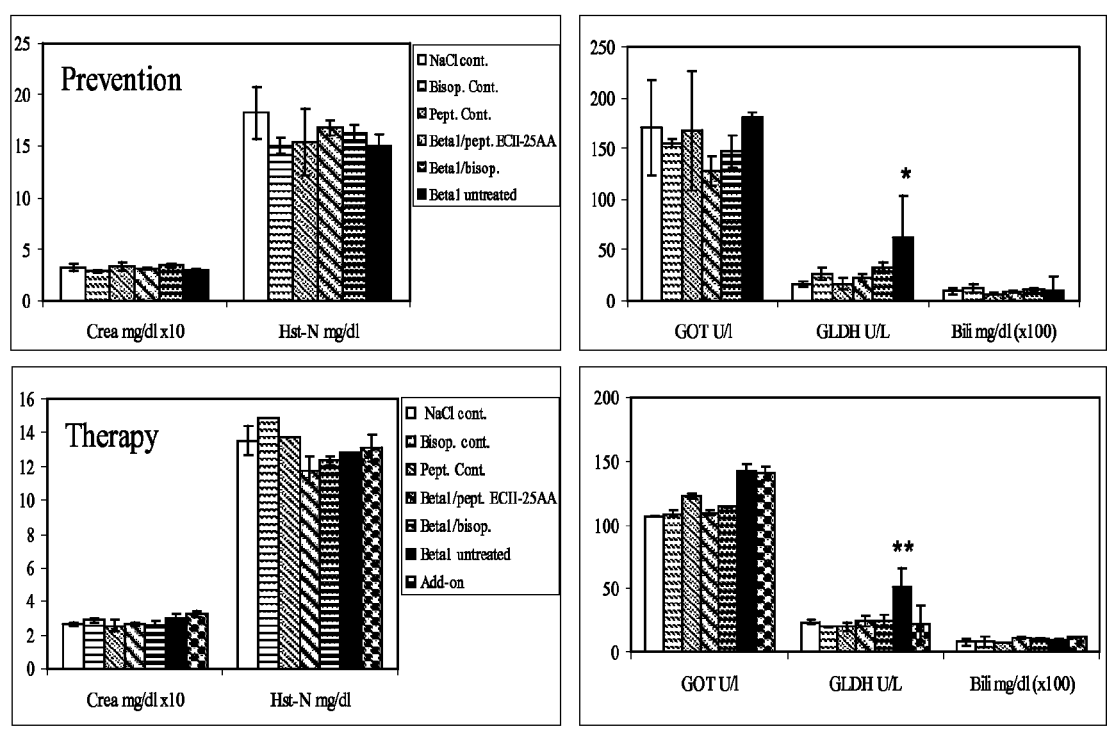

FIG. 14 shows different laboratory parameters determined in the serum of animals at the end the prevention (upper panels) and the therapy study (lower panels), respectively, whereby "Beta1 untreated" means immunized anti-1-positive not treated animals, "Beta1/bisop." means immunized animals prophylactically (upper panels) or therapeutically (lower panels) treated with bisoprolol, "Beta1/pept." means immunized animals prophylactically (upper panels) or therapeutically (lower panels) treated with the 25AA-peptide Ic, "Add-on" means immunized anti-1-positive animals therapeutically treated with a combination of bisoprolol and the cyclic 25AA-peptide Ic after 8 months of immunization, and "Cont." means the respective control groups in both the prevention and the therapy study. Crea means creatinine, Hst-N means urea, GOT means glutamic oxaloacetic transaminase, Bili means bilirubin, GLDH means glutamate lactate dehydrogenase.

Figure 15:
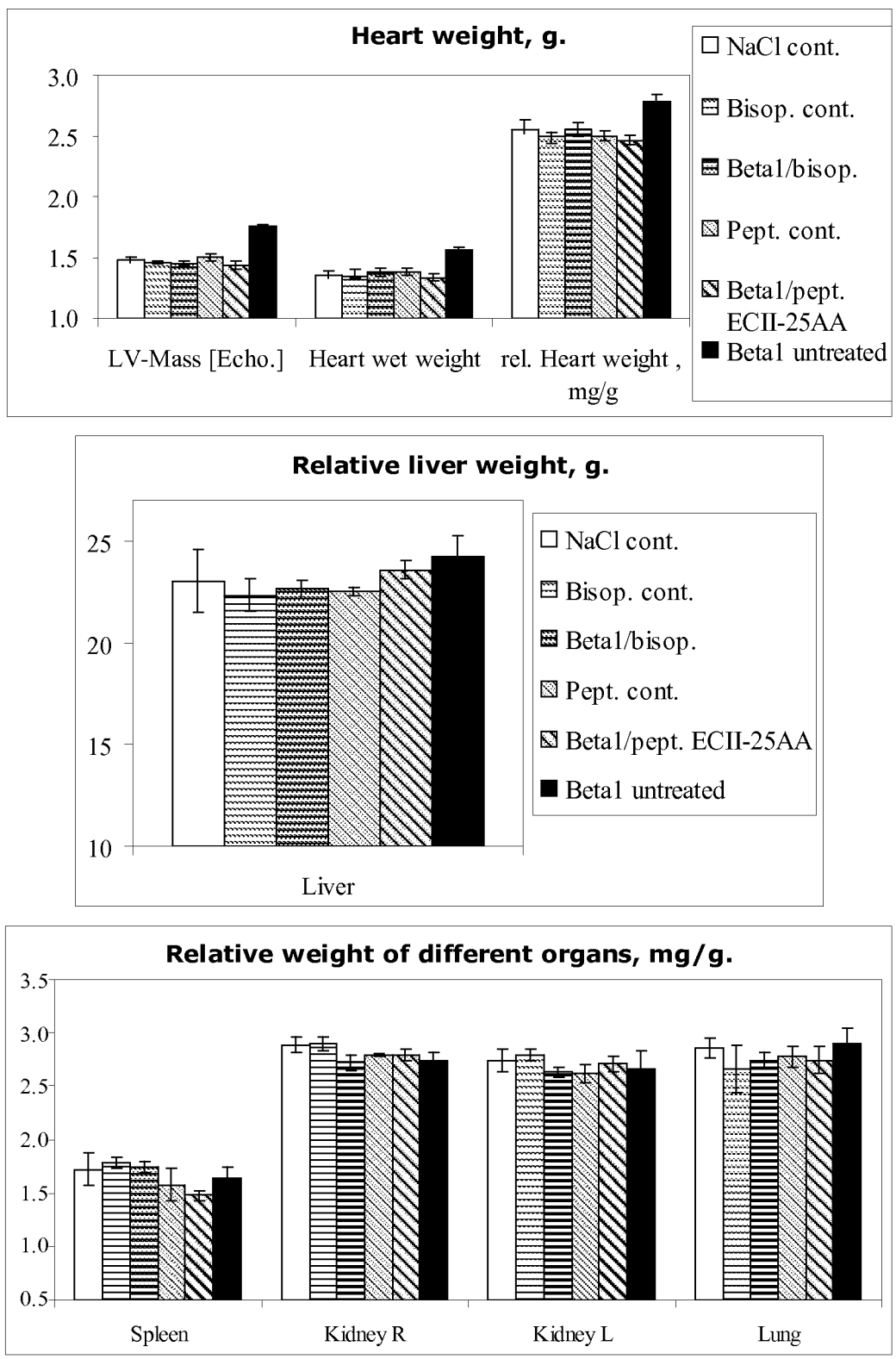

FIG. 15 shows macro anatomic parameters of the animals from the prevention study as columns. The relative weights of different organs were determined in g, whereby "Beta 1 untreated" means immunized animals being not treated, "Beta1/bisop." means immunized animals prophylactically treated with bisoprolol in a dosage of 15 mg/kg and "Beta1/pept. ECII-25AA" means immunized animals prophylactically treated using the 25AA-ECII peptide Ic in dosage of 1 mg/kg each; "Cont." means the respective control groups; Kidney R means right and Kidney L means left.

Figure 16:
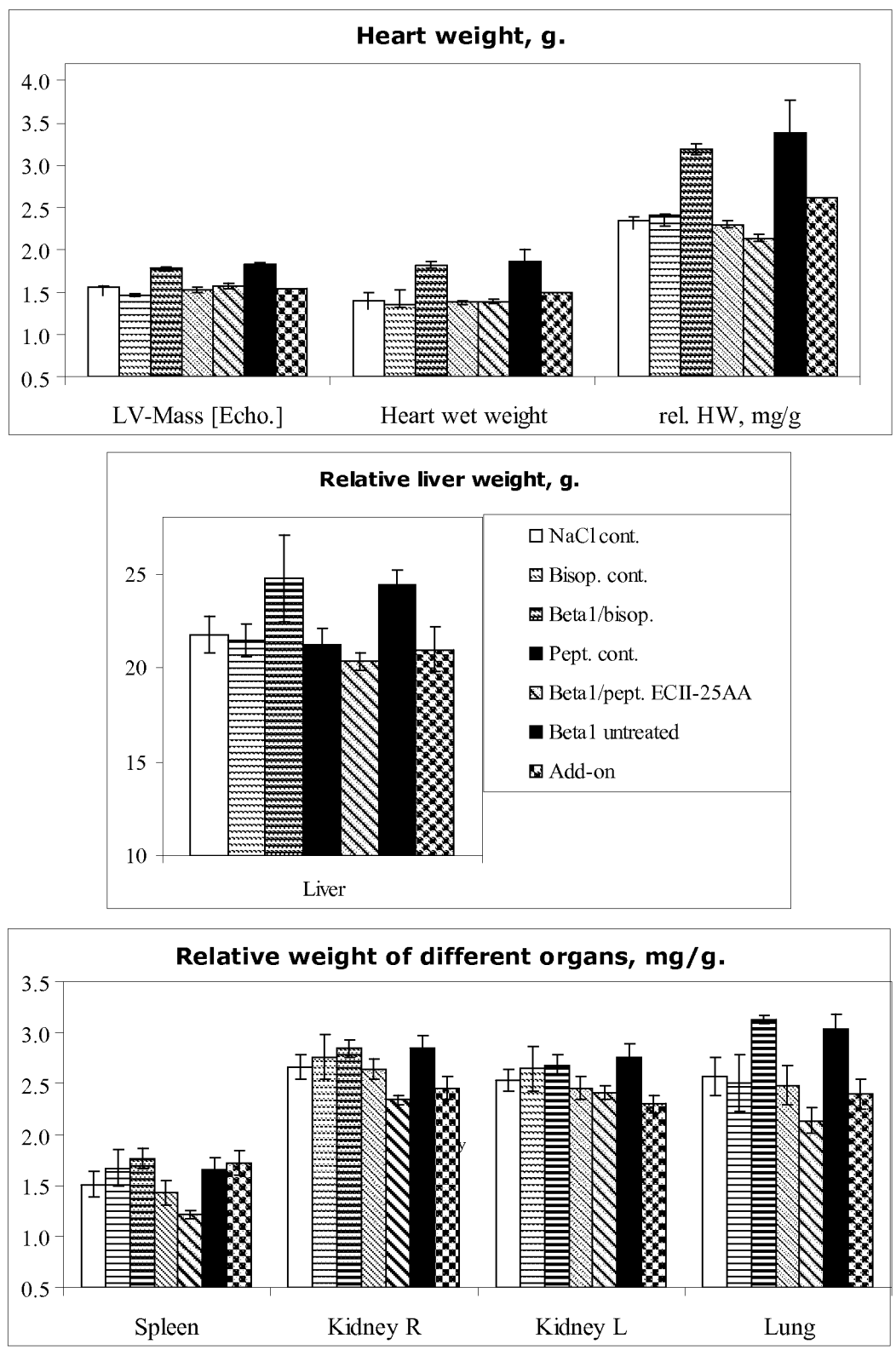

FIG. 16 shows macro anatomic parameters of the animals from the therapy study as columns. The relative weights of different organs were determined in g, whereby "Beta1 untreated" means immunized anti-1-positive cardiomyopathic animals being not treated, "Beta1/bisop." means immunized anti-1-positive cardiomyopathic animals therapeutically treated with bisoprolol in a dosage of 15 mg/kg, "Beta1/pept. ECII-25AA" means immunized anti-1-positive cardiomyopathic animals therapeutically treated with the 25AA-ECII peptide Ic in dosage of 1 mg/kg each, "Add-on" means therapeutic treatment of immunized anti-1-positive cardiomyopathic animals with a combination of bisoprolol/cyclic peptide after 8 months of immunization, and "Cont." means the respective control groups. Kidney R means right and Kidney L means left.

Figure 17:
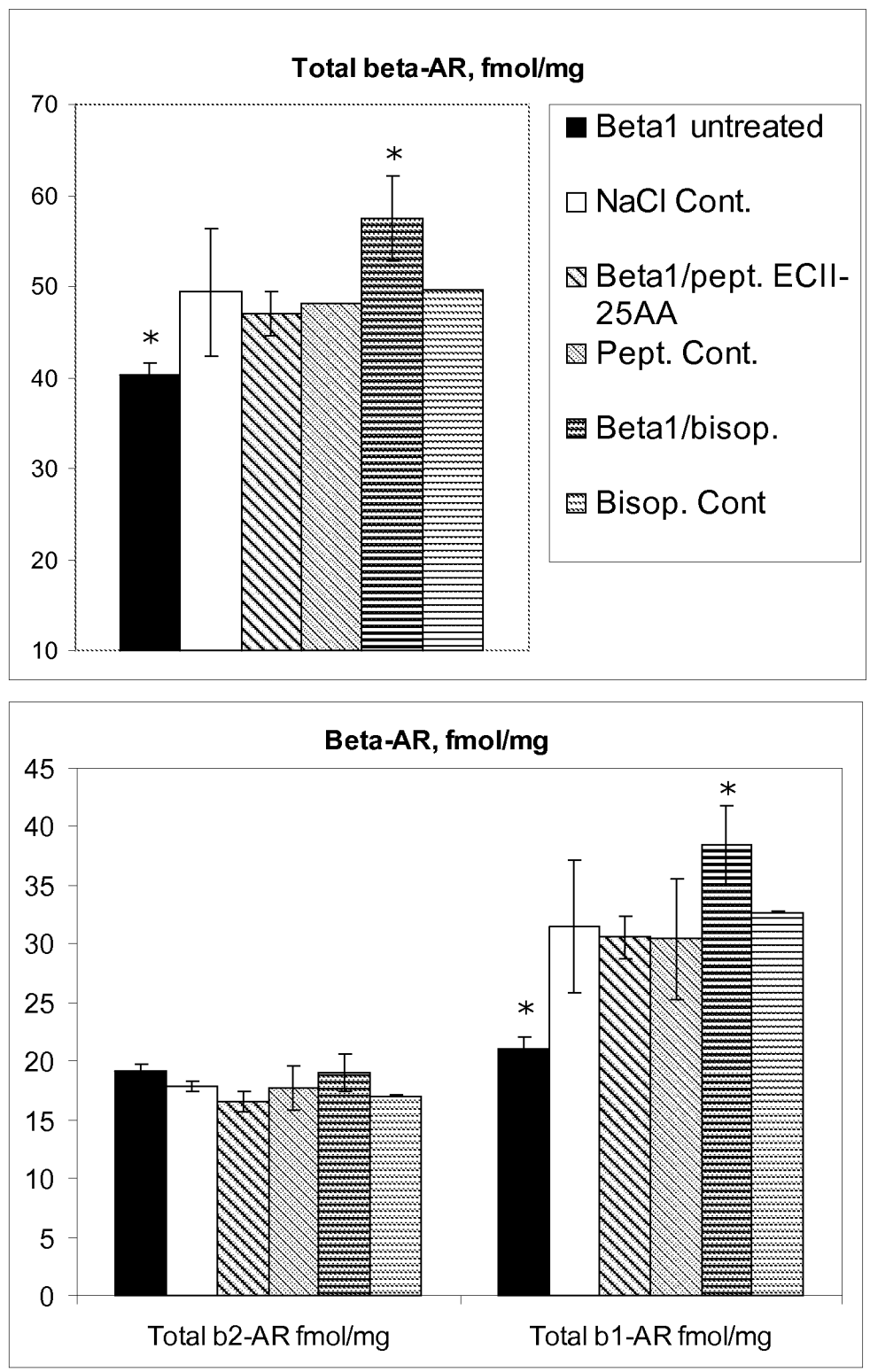

FIG. 17 shows densities of cardiac beta-adrenergic receptors in the heart of the animals from the prevention study as columns. The upper panel shows the total amount of cardiac membrane beta-AR, given in femtomol per milligram (fmol/mg) membrane protein. The lower panel shows the amount of the beta2-AR (left) and beta1-AR subtypes (right), respectively. "Beta1 untreated" means immunized anti-1-positive animals being not treated, "Beta1/bisop." means immunized anti-1-positive animals prophylactically treated with bisoprolol in a dosage of 15 mg/kg and "Beta1/pept. ECII-25AA" means immunized anti-1-positive animals prophylactically treated using the 25AA-ECII peptide Ic in dosage of 1 mg/kg each, "Cont." means the respective control groups.

Figure 18:
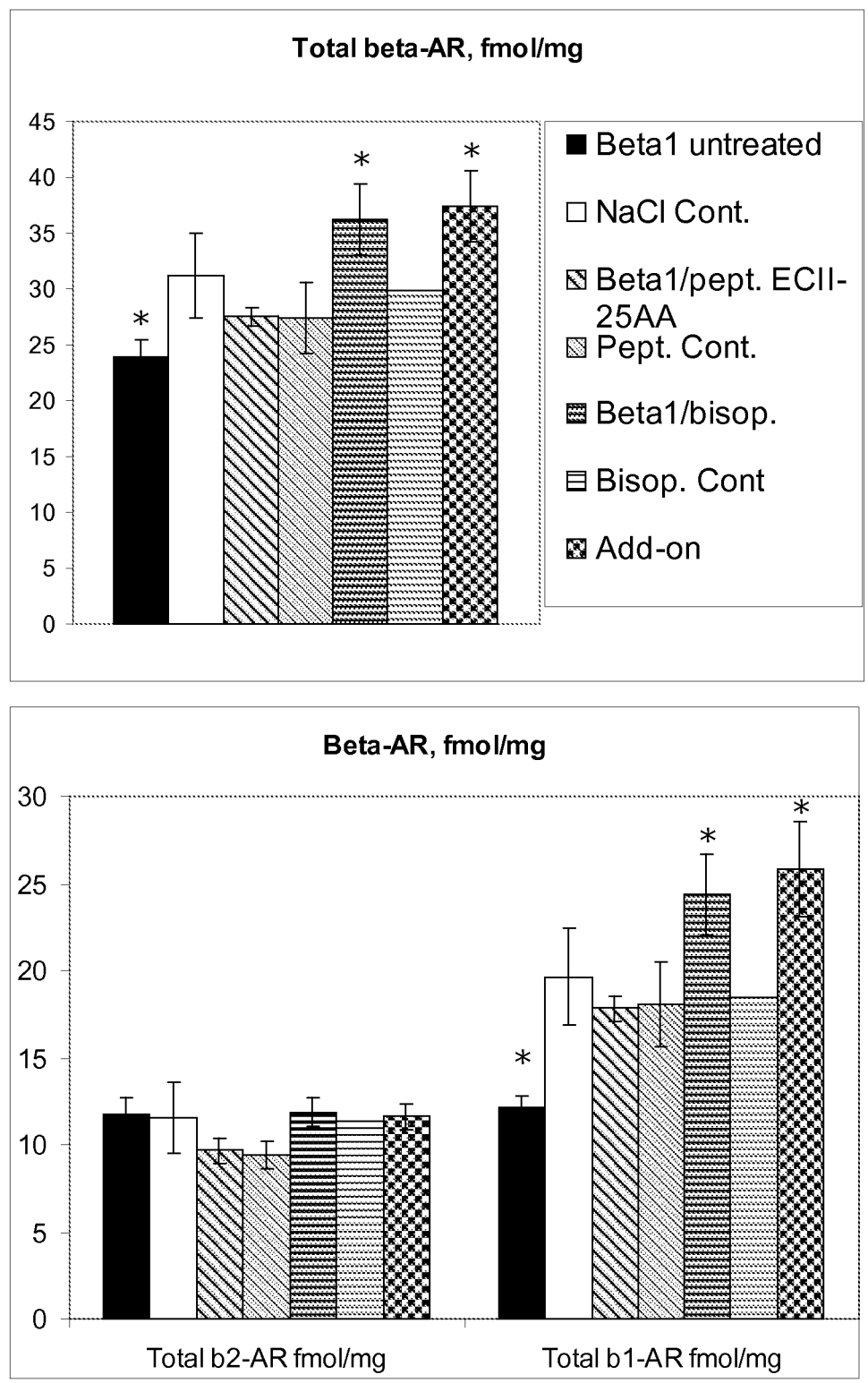

FIG. 18 shows densities of cardiac beta-adrenergic receptors in the heart of the animals from the therapy study as columns. The upper panel shows the total amount of cardiac membrane beta-AR, given in femtomol per milligram (fmol/mg) membrane protein. The lower panel shows the amount of the beta2-AR (left) and beta1-AR subtypes (right), respectively. "Beta1 untreated" means immunized anti-1-positive cardiomyopathic animals being not treated, "Beta1/bisop." means immunized anti-1-positive cardiomyopathic animals therapeutically treated with bisoprolol in a dosage of 15 mg/kg and "Beta1/pept. ECII-25AA" means immunized anti-1-positive cardiomyopathic animals therapeutically treated using the 25AA-ECII peptide Ic in dosage of 1 mg/kg each; "Add-on" means therapeutic treatment of immunized anti-1-positive cardiomyopathic animals with a combination of bisoprolol/cyclic peptide after 8 months of immunization, and "Cont." means the respective control groups.

FIG. 19 shows the results of T-cell recall-assays carried out with T-cells prepared from the spleen of immunized anti-1-positive cardiomyopathic not treated animals ("Beta1 untreated") compared with those from immunized anti-1-positive cardiomyopathic animals (a) prophylactically or (b) therapeutically treated with bisoprolol (Beta1/bisop.) or the cyclic 25AA-ECII cyclopeptide Ic ("Beta1/pept. ECII-25AA"). "Cont." means the respective not immunized control animals. The assays were carried out according to Schmidt J. et al. (2003) *J Neuroimmunol.* 140, 143-152. In brief, to purify CD4+ T-cells from the splenic cell preparations, B-cells and CD8+ T-cells were depleted by commercially available magnetic beads (MACS®), yielding a purity of CD4+ cells >85%. $1\times10^5$ CD4+ of the purified T-cells were then co-incubated in 96-well plates with $1\times106$ irradiated thymic antigen presenting cells (prepared from a younger rat). Reagents added in the different assays (conditions) were: 10 μg/ml glutathion-S-transferase (GST), 2 μg/ml Concanavalin A (ConA, positive control), 10 μg/ml 25AA-ECII peptide (Pept.25AA), and GST/beta1-ECII fusion protein (FP) at a concentration of 1.0 and 0.1 μg/ml, respectively. The measured T-cell reactivities were normalized to the respective T-cell reactivities obtained with 10 μg/ml purified protein derivative (PPD) carried out in parallel under each condition. After 48 hours of incubation, 50% of the supernatants were removed and replaced by fresh medium. The cells were then pulsed with 1.25 μCi/well [$^3$H]-thymidine and further incubated for 16 hours before the cells were harvested, and the DNA-incorporated radioactivity was measured using a beta-plate.

FIG. 20 shows the results of ELISPOT-assays carried out with B-cells prepared from either the spleen or the bone marrow of immunized anti-1-positive cardiomyopathic not treated animals ("Beta1 untreated") compared with those isolated from immunized anti-1-positive cardiomyopathic animals therapeutically treated with the 25AA-ECII peptide Ic ("Beta1/pept. ECII-25AA"). For the assays, ELIspot plates were coated overnight with either 1.8 μg/ml anti-rat IgG (H+L) or the specific antigen (GST/beta1-ECII-FP) in 0.05 mol/l Tris buffer, pH 9.4. Then the plates were washed 3 times and blocked with BSA for 3 hours at 37° C. Subsequently, the plates were incubated overnight at 37° C. with B-cells from either spleen or bone marrow (cultured in RPMI 1640/X-VIVO-15 medium supplemented with 10% fetal calf serum (FCS)) with $1\times106$ to $1\times103$ cells per well. After 12 hours the B-cells were discarded and the plates with the B-cell secreted IgG bound were washed several times (PBS/0.5% Tween) before the addition of alkaline phosphatase conjugated secondary anti-rat IgG (0.3 μg/ml) to detect bound rat IgG. Then the plates were incubated for another 3 hours at 37° C., washed several times with PBS/0.5% Tween, and developed using LMP/BICP 5:1 (1 ml per well; "LMP" means low melting agarose, and "BICP" means 5-bromo-4-chloro-3-indolyl phosphate p-toluidine salt, a blue-colored dye) allowing for a quantification of the blue spots obtained, with each spot representing either (a) an IgG or (b) an antigen-specific IgG secreting spleen or bone-marrow cell, respectively. Panel a depicts the total amount of IgG secreting cells per 104 coated cells, panel b depicts the fraction of specifically anti-beta1-ECII IgG secreting cells; "BM" means bone marrow.

Figure 21:
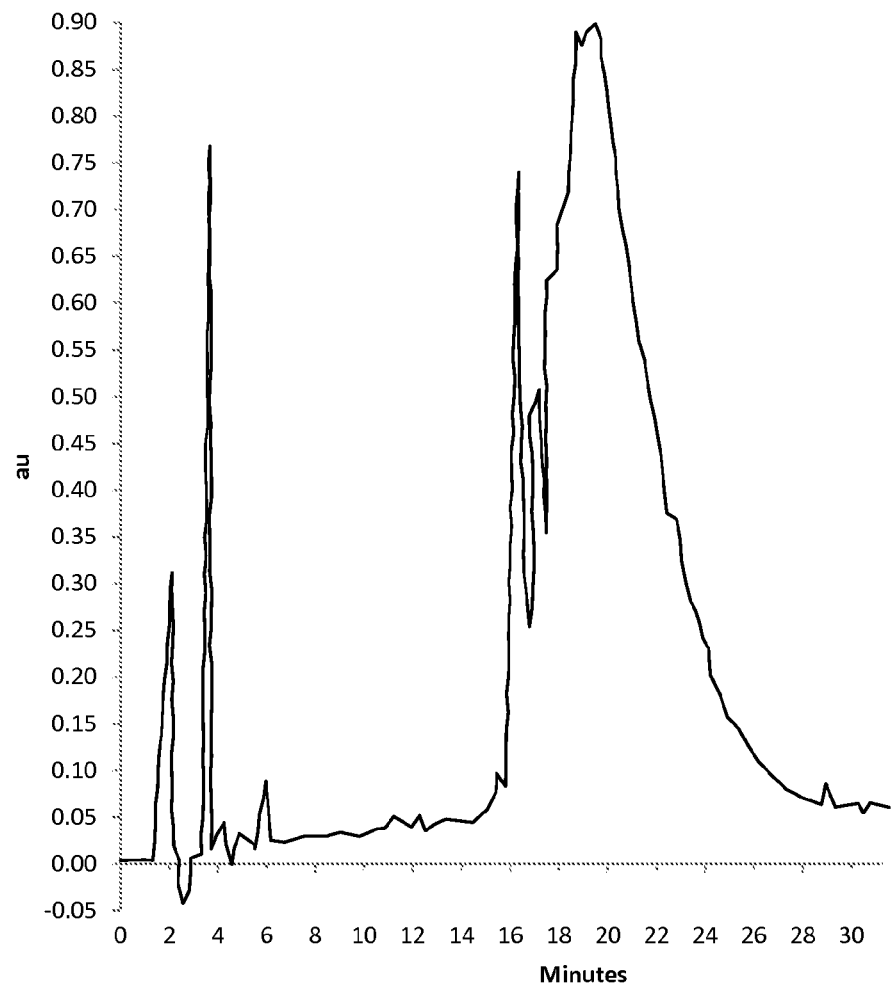

FIG. 21 represents an example of the spectroscopic characterization of the 25AA-ECII, namley the cyclic peptide Ic by high pressure liquid chromatography (HPLC, FIG. 21), and mass spectroscopy method (MALDI-TOF, data not shown). HPLC was carried out in a Waters Separation Modul 2690 together with a Waters Dual Lambda UV detector, wave length set at 220 nm. After peptide-synthesis and cyclization, the samples were dissolved in H2O/5% acetonitril (ACN) and loaded on a reversed phase column (Nuclosil 100-5/C18, Macherey-Nagel Inc., Germany; column length 250 mm, diameter 4 mm) with a flow of 1 ml/min. For separation a gradient 5% to 60% ACN with 0.2% TFA was used. A very small peak of linear 1-ECII-25AA peptide was seen, typically between 14 and 16 min, whereas the fractions containing the cyclic beta1-ECII-25AA peptide appeared in a range from 18 to 22 min. Aliquots of these fractions containing 20-80 μg/ml of the cyclic peptide were further analyzed by mass spectroscopy. The expected molecular masses of the linear versus cyclic beta1-ECII-25AA are 2948-2949 versus 2929-2930, respectively. The example demonstrates a representative mass spectrum of a cyclic beta1-ECII 25AA peptide. The ordinate demonstrates signal intensities ("a.u." means arbitrary units), the abscissa, and the molecular mass (m/z) (data not shown).

Figure 22:
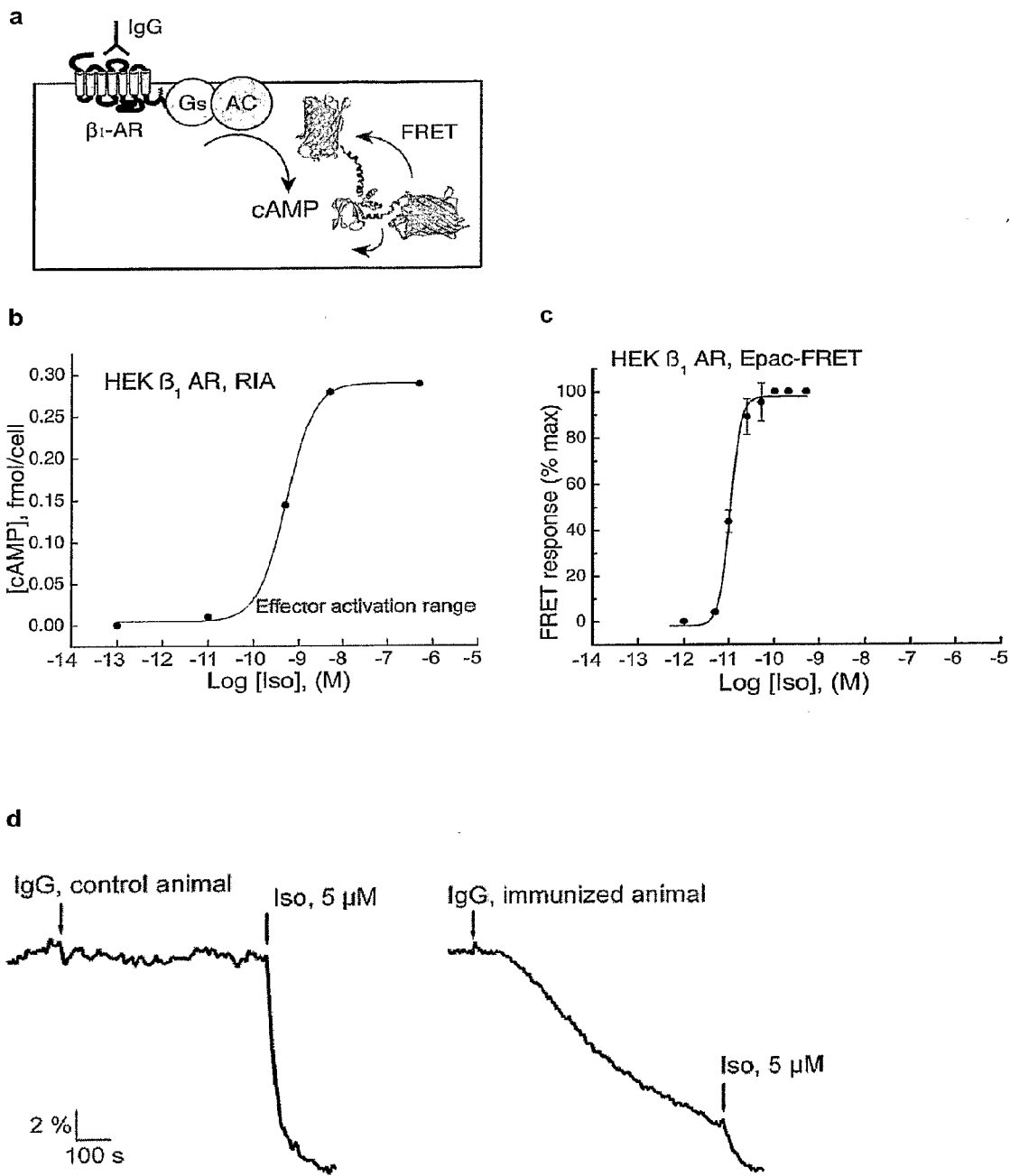

FIG. 22 shows a cell-based approach for the detection of functional anti-beta1-Abs. a, Receptor activation induced by binding of antibodies to its accessible extracellular loops leads to an increase in cAMP through sequential activation of Gs-proteins and adenylyl cyclase (AC) which is detected by FRET as a conformational change in the cAMP-binding domain of Epac1 fused between CFP (cyan) and YFP (yellow) proteins (Epac1-camps). b, Measuring cAMP levels (fmol/cell) in isoproterenol-stimulated HEKβ1AR cells by conventional radio-immunoassay (Amersham) or c, Epac-FRET. One of 3 independent experiments (EC50=0.53±0.19 nM) is shown. The cAMP-range that can be monitored by Epac-FRET is presented by the horizontal grey bar in FIG. 22b. At 0.1 nM isoproterenol Epac1-camps gets saturated indicating an intracellular cAMP concentration at ~20 µM. This extremely sensitive sensor is characterized by a high dynamic range at physiologically relevant cAMP concentrations 0.1-20 µM (which are covered by only 10% of the maximal cAMP-RIA signal), making minor, in conventional assays not-significant cAMP changes well detectable by Epac-FRET. d, IgG prepared from rats immunized with the second extracellular loop of the human beta1-AR (beta1-ECII) were tested for activity using HEKβ1AR cells transfected with Epac1-camps, and compared with non-immunized animals to assess the reliability of the method. FRET ratio traces are presented (% corresponds to the relative change in YFP/CFP intensity ratio; Iso, (−)Isoproterenol). The decrease in FRET reflects a rise in intracellular cAMP (representative experiments, n=6).

Figure 23:
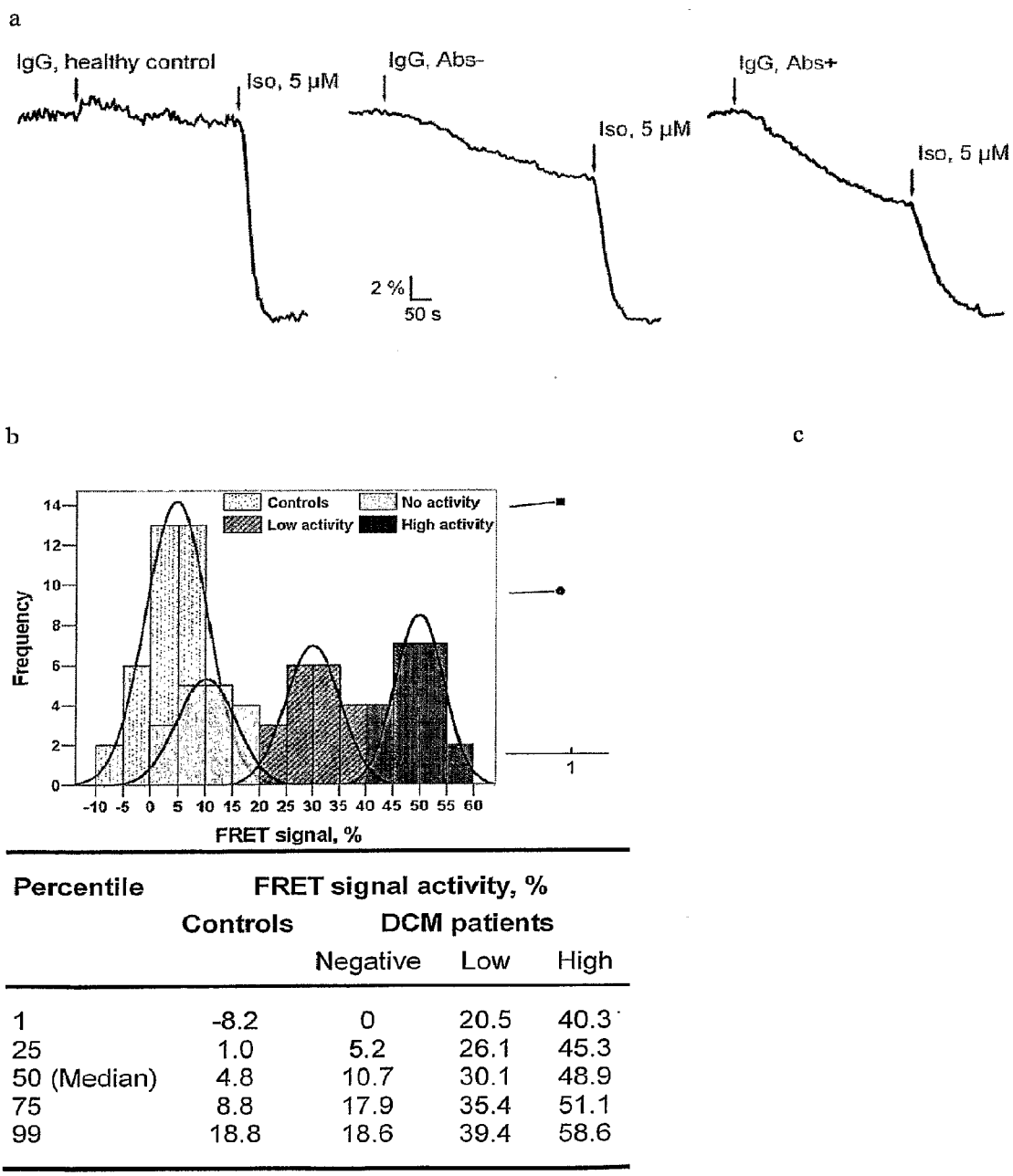

FIG. 23 shows the measurement of cAMP by Epac-FRET detects anti-beta 1-Abs in DCM patients. a, None of the IgG prepared from healthy controls (n=40) induced a significant cAMP-response in living cells (left). IgG from DCM patients previously judged anti-beta1-Ab-positive 5 (Abs+) elicited marked cAMP responses (49.5±3.8% of maximal Iso-signal, middle). IgG from 33.9% of previously anti-beta 1-Ab-negative judged patients (Abs-) demonstrated a robust but significantly smaller increase in cAMP (30.7±5.6%, P<0.01). Representative experiments of at least 3 cells for each serum. b, Histogram with normality curves of the strength of the FRET signal in healthy controls and DCM patients. The antibody-induced FRET responses allow to differentiate between controls and three groups of activity: no activity (n=17), low activity (n=19), high activity (n=20); P<0.01 for the difference between "high" and "low"-activators). c, Concentration-response relation between "high" and "low" activator IgG demonstrating different activatory capacities in a wide range of antibody concentrations. The %±SEM of maximal Iso-induced cAMP response (normalized to maximal changes in FRET produced by a "high" activator) is presented (representative experiments, n=4).

Figure 24:
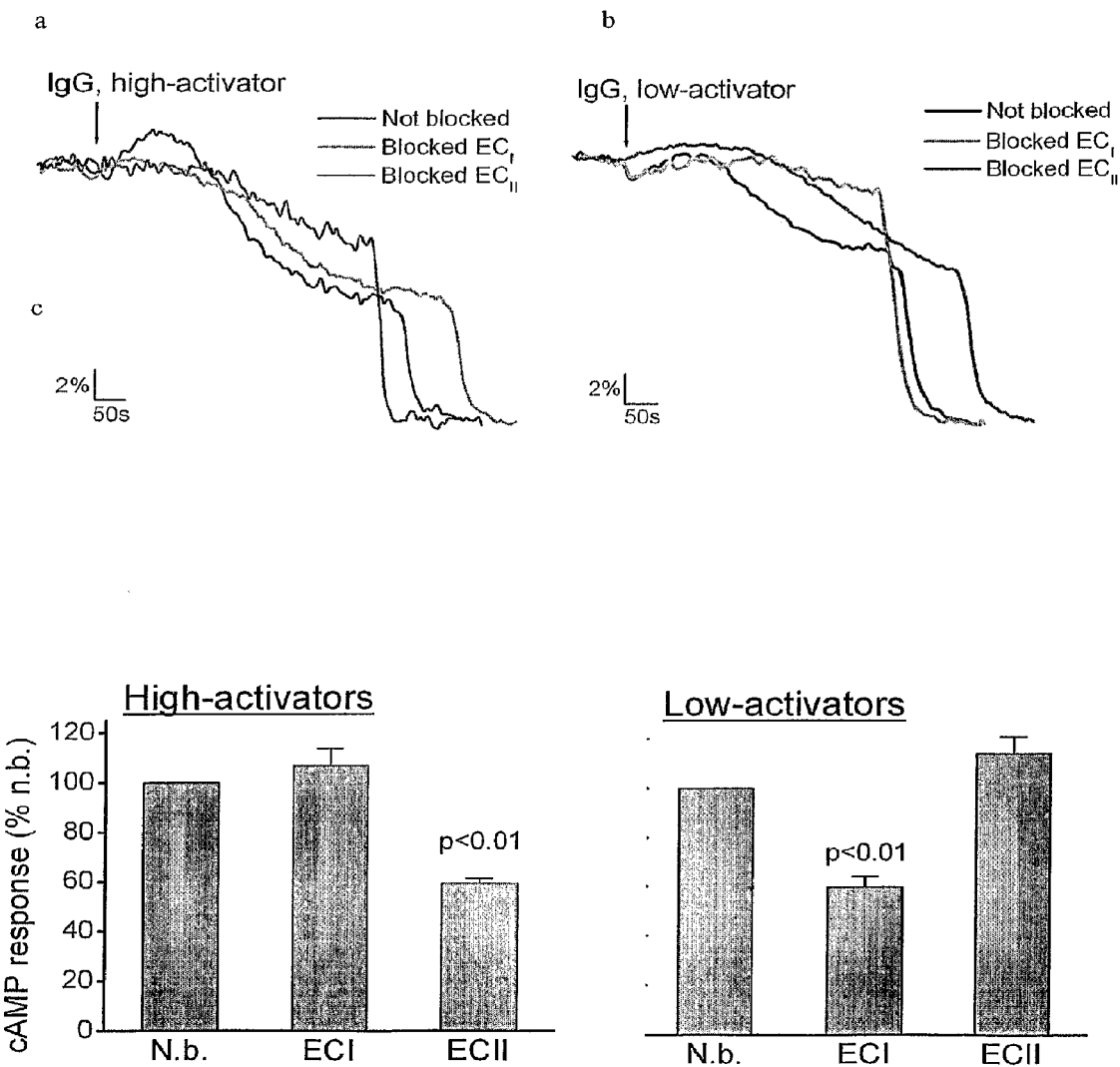

FIG. 24 shows blocking experiments for different classes of anti-beta1-Abs. a, cAMP production induced by a "high" activator is attenuated only by a specific peptide derived form the second extracellular beta1-AR loop (beta 1-ECII). b, "Low" activator signals could be blocked in all instances by a peptide corresponding to the first extracellular loop (beta1-ECI) but not by beta1-ECII-peptides (representative experiments from at least 3 cells per condition). c, Results of the cross-blocking experiments with IgG obtained from n=7 representative "high", and n=8 representative "low" activator DCM patients.

EXAMPLE 1

Peptide Synthesis

Linear peptides are synthesised using the solid phase Fmoc protocol on a Multiple Peptide Synthesizer (SYROII, Multi-SynTech GmbH, Witten). The synthesis was performed using side chain protected Fmoc amino acid derivatives on Rink Amide or Rink Amide MBHA resins (Novabiochem-Merk Biosciences GmbH, Bad Soden). The Fmoc amino acids are activated through diisopropylcarbodiimide/N-hydroxybenzotriazole or benzotriazole-1-yl-oxy-tris-pyrrolidino-phosphonium hexafluorophosphate.

For the synthesis of cyclic peptides on the solid phase Fmoc-Glu-ODmab or another Fmoc amino acid having a side chain protecting group which can be selectively cleaved off in an orthogonal manner, is incorporated at the C-terminal end of the linear peptide. After selective removal of the Dmab side chain using 2% hydrazine monohydrate in N,N'-dimethylformamide the resin-bound linear peptide is treated in the presence of diisopropylcarbodiimide and N-hydroxy-9-azabenzotriazole in N,N'-dimethylformamide for several hours. The cyclisation was monitored by taking samples and performing the Kaiser-Test and, if necessary, repeated. The cleaving off of the cyclic peptide from the synthesis resin generates a peptide amide and the removal of the protective groups of the side chain is done by treating the resin with trifluoro acetic acid/triisopropylsilane/ethandithiole/water for 2 hours.

EXAMPLE 2

Animal Model

The animal model used in this example and any other example described herein if not indicated to the contrary, is the human analogue rat model. Prior to evaluating and testing, respectively, this human analogue rat model using bisoprolol and the various compounds of the present invention, more particularly compounds of formula Ic, the animals were treated as follows.

In order to generate anti-β1-receptor antibodies the animals were immunized against the second β1-receptor loop. In animals neither receiving bisoprolol nor any peptide according to the present invention, progressive dilated immune cardiomyopathy was observed after 8 months of immunization (FIG. 6). In both the prevention and the therapy study all of the immunized animals developed high titers of stimulatory anti-β1-EC$_{II}$ antibodies. The specific anti-β1-EC$_{II}$ titer reached a maximum between 6 and 9 months of continuously boosting the animals every 4 weeks (FIGS. 4 and 8).

EXAMPLE 3

Prevention of Immune-cardiomyopathy in the Human Analogue Rat Model Using Either Bisoprolol or a Peptide According to the Present Invention Prophylactic treatment of the animals by administering 1 mg/kg of the cyclic peptide of formula Ic either subcutaneously (n=4) or intravenously (n=4) every 4 weeks prevented a further increase of the specific anti-β1-EC$_{II}$ antibody-titer with the titer even continuously declining in the further course of the study (FIG. 4).

To the big surprise of the present inventors, from the fifth month on no more immune response was observed upon antigen boost every 4 weeks as shown in FIG. 4. This means that some sort of immunological tolerance in the sense of a hyposensitization with consecutive anergy, i. e. suppression or reduced activation of the anti-β1-$EC_{II}$ producing B cells occurred. Further analysis of the nature of this "immunological anergy" revealed an important decrease in antigen-specific antibody-producing splenic B-cells in the presence of the cyclic peptide (FIG. 20), whereas regulatory $CD4^+$ T-cells and/or other mechanisms of T-cell induced tolerance do not obviously account for this unresponsive state (FIG. 19a). FIG. 20 shows that the specifically anti-β1-$EC_{II}$ antibody producing B-cells were significantly reduced in the spleen of animals treated with 1 mg/kg of the cyclic peptide of formula Ic.

As shown in FIGS. 5 and 12, the cyclic peptide did neither decrease heart rate nor blood pressure. In contrast thereto, prophylactic administration of bisoprolol, as also shown in FIGS. 5 and 12, resulted in a significant reduction in heart rate with the significance level being $p<0.01$. As may be taken from FIG. 6, there is a significant difference in the echocardiographic phenotype between the anti-β1-$EC_{II}$-antibody positive animals which have undergone prophylaxis and those which had no treatment.

EXAMPLE 4

Treatment of Immune-cardiomyopathy in the Human Analogue Rat Model Using Bisoprolol and a Peptide According to the Present Invention Upon administration of the peptide of the present invention peptide Ic every 4 weeks, a surprisingly rapid decrease in the specific anti-beta 1-$EC_{II}$ antibody titer was observed as shown in FIGS. 8a and b. Compared with peptide-treated animals, the groups receiving bisoprolol had even higher beta1-antibody titers. As shown in FIGS. 10 and 11, with both the administration of bisoprolol as well as of the peptide of the present invention (after immunization and generation of significant LV dilatation) there was no progression as monitored by echocardiography within the 12 months during which the animals underwent this kind of treatment, compared with untreated anti-beta-1-ECII-antibody positive animals. Even more surprisingly, there was even a significant regression of LV dilatation in all peptide-treated animals with β1-ECII-16AA obviously being less effective than β1-ECII-25AA or β1-ECII-18AA (FIG. 11), whereas LV-dilatation could not be reversed completely when using bisoprolol as the sole therapeutic agent.

These results indicate that with bisoprolol alone the disease may be stabilized, or, by using the present invention peptide, even a regression of the cardiomyopathic phenotype may be achieved.

EXAMPLE 5

Administration of a Combination Consisting of a Cyclic Peptide of the Present Invention and Bisoprolol Both in the rat model as well as in DCM patients the stimulatory, i. e. allosteric effects of β1-$EC_{II}$-antibodies can be abolished with a cardioselective beta blocker (used in accordance with standard medication). From this it is concluded that β1-(auto)antibody positive patients will profit more than β1-(auto)antibody negative patients from the present invention. This suggests an even higher efficiency of a combination therapy consisting of bisoprolol and a peptide of the present invention for anti-beta-1-$EC_{II}$-antibody positive patients. Supposed additive mechanisms could be, within others, protection from antibody-induced receptor-downregulation by the peptide together with a synergistic β1-receptor upregulation by the beta-blockers (like bisoprolol or metoprolol, see FIG. 18). For synergistic effects in the animal model (see FIGS. 10c, 11c, and 13).

EXAMPLE 6

Administration of Shorter Variants of the Cyclic Peptide of the Present Invention (i.e. 16 Amino-acid vs. 18 Amino-acid vs. 25 Amino-acid Cyclic Peptides)

Figure 10A:
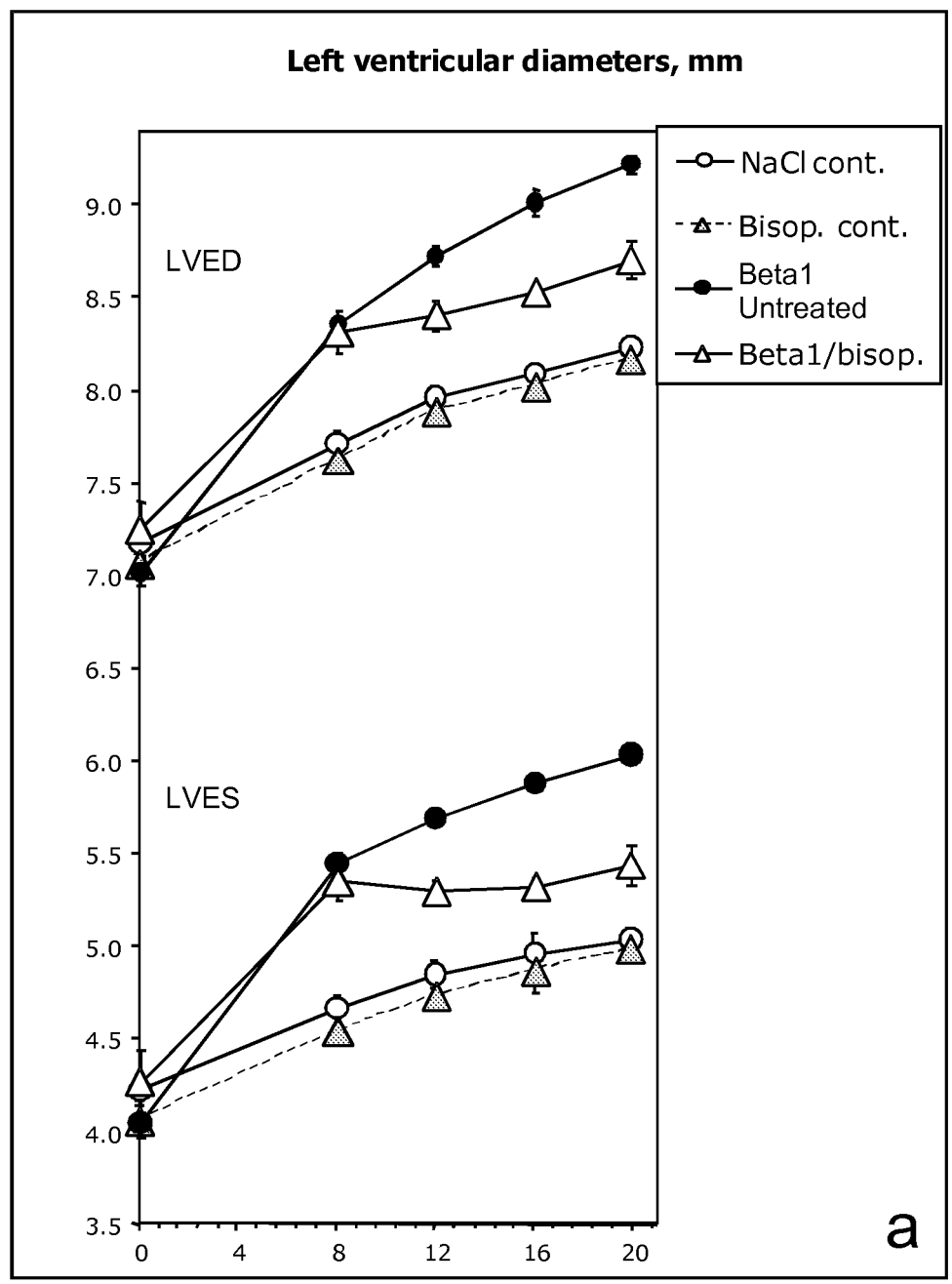
Figure 10B:
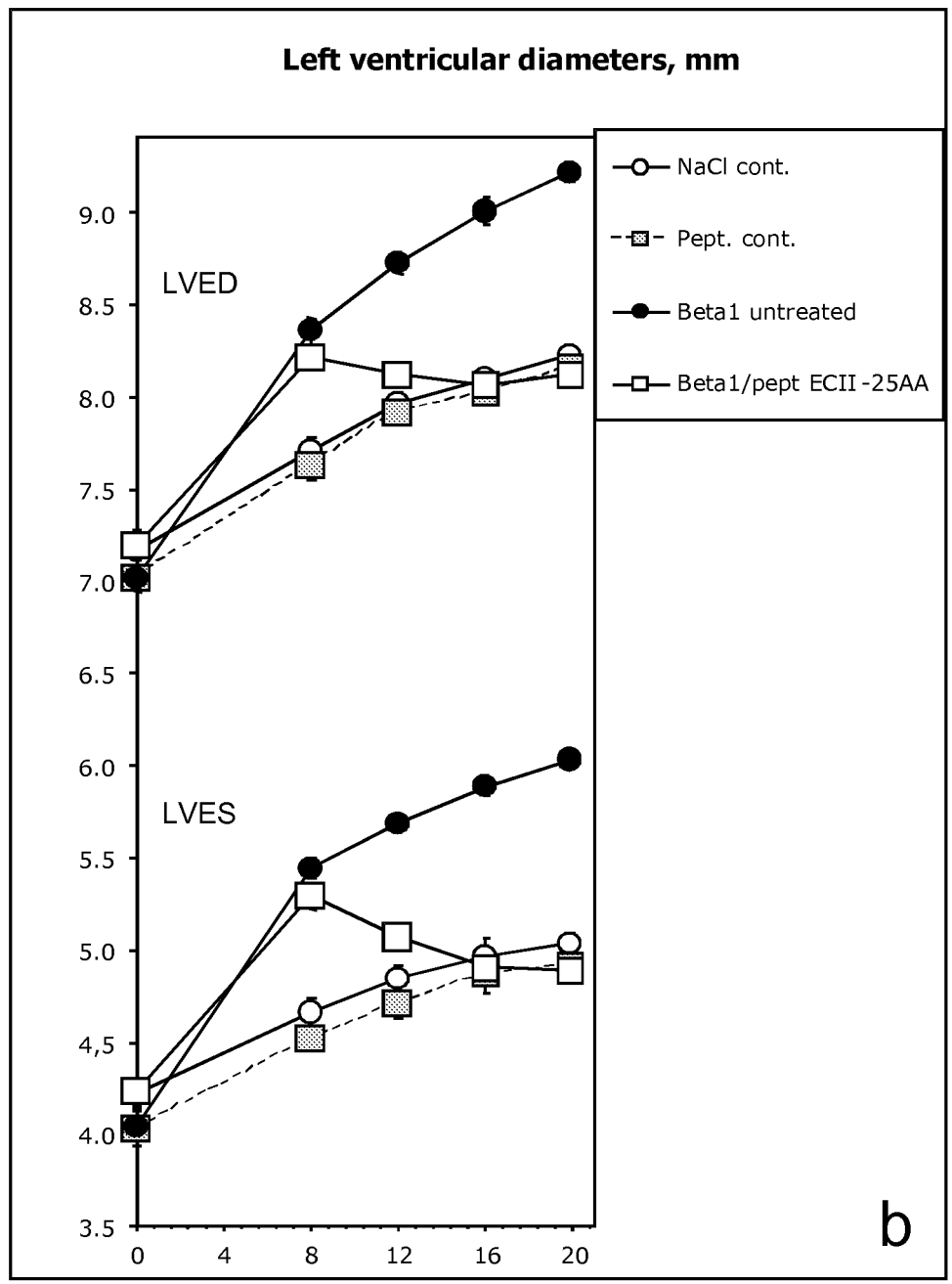
Figure 10C:
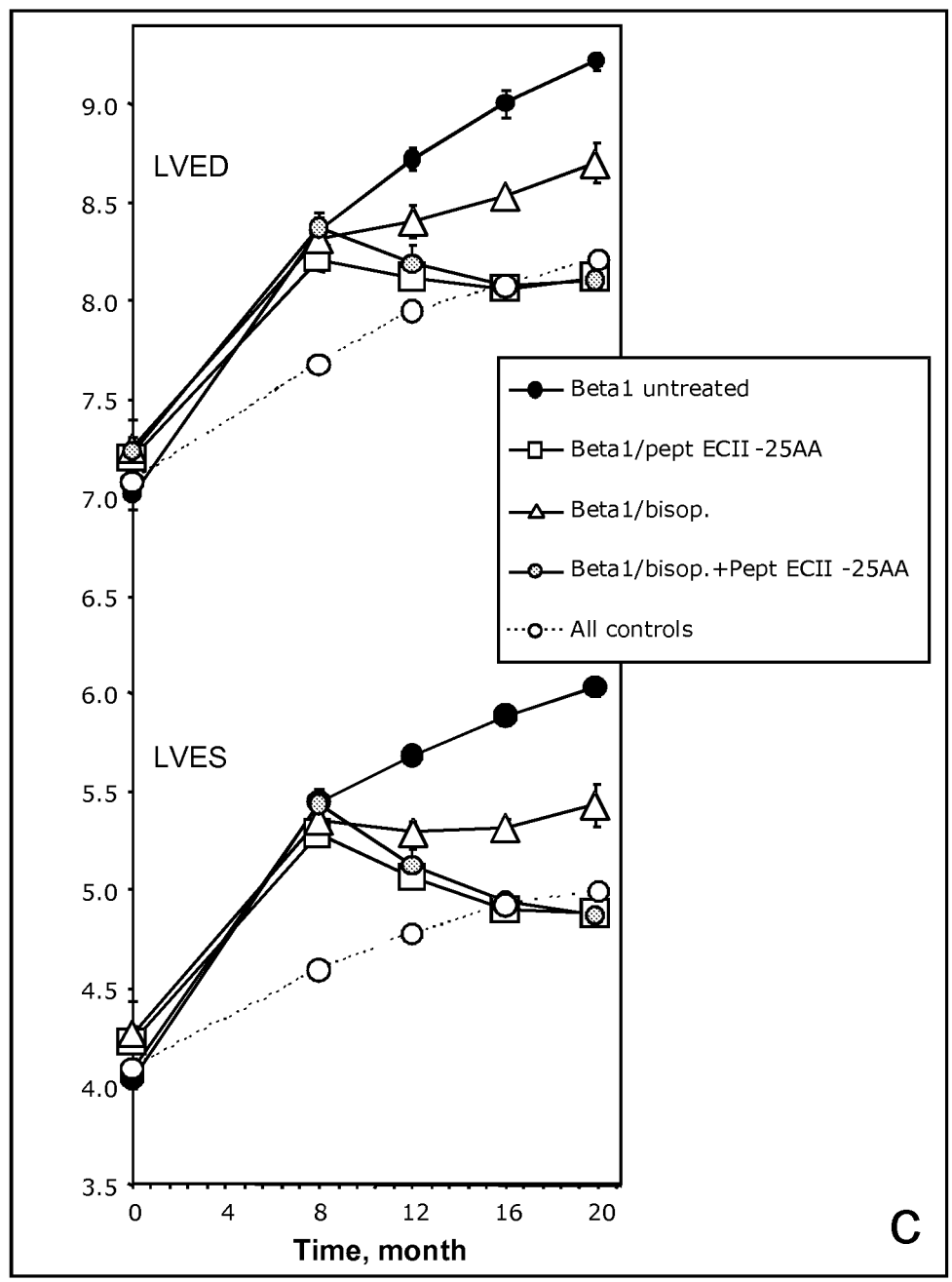
Figure 10D:
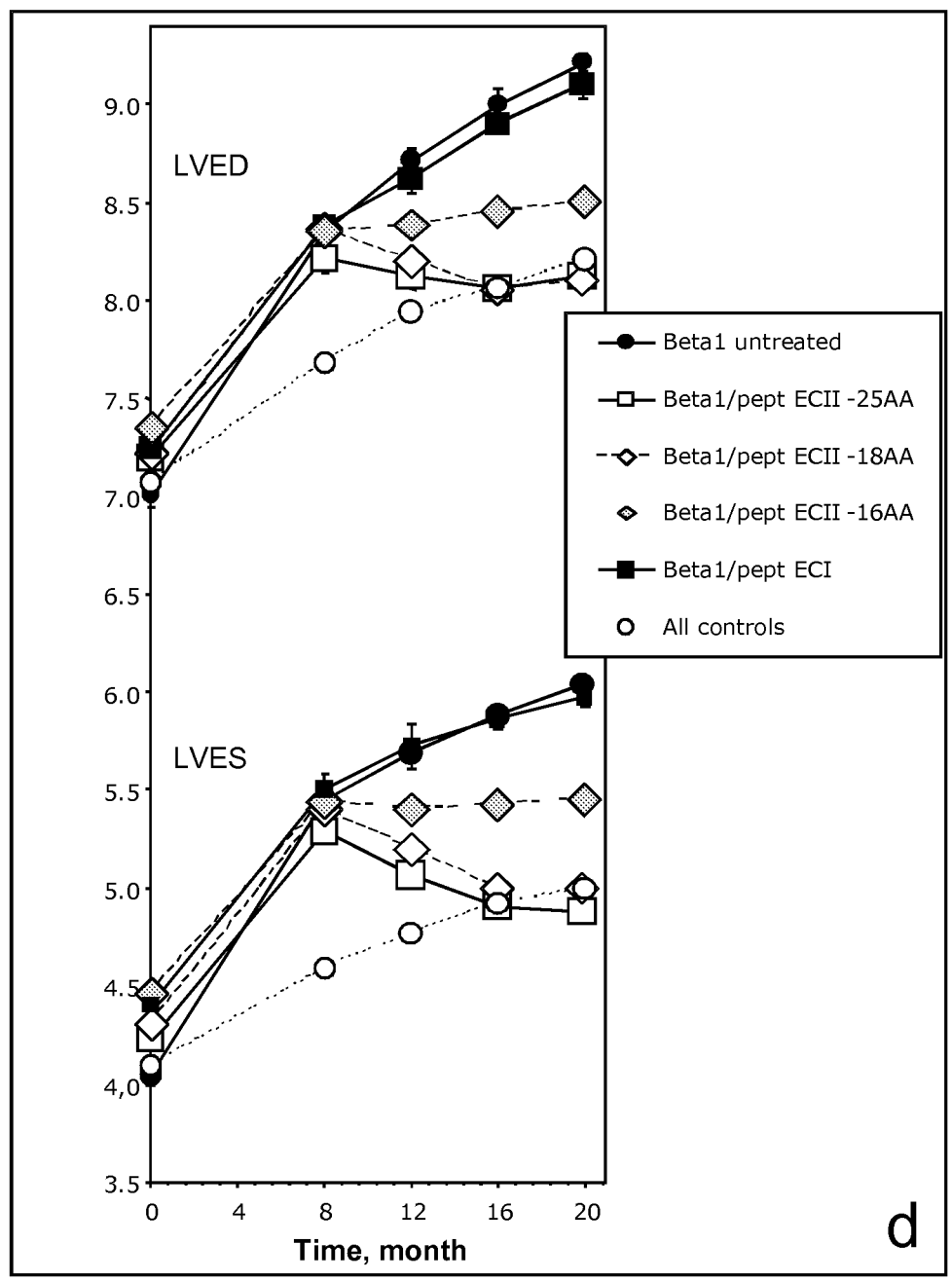
Figure 11A:
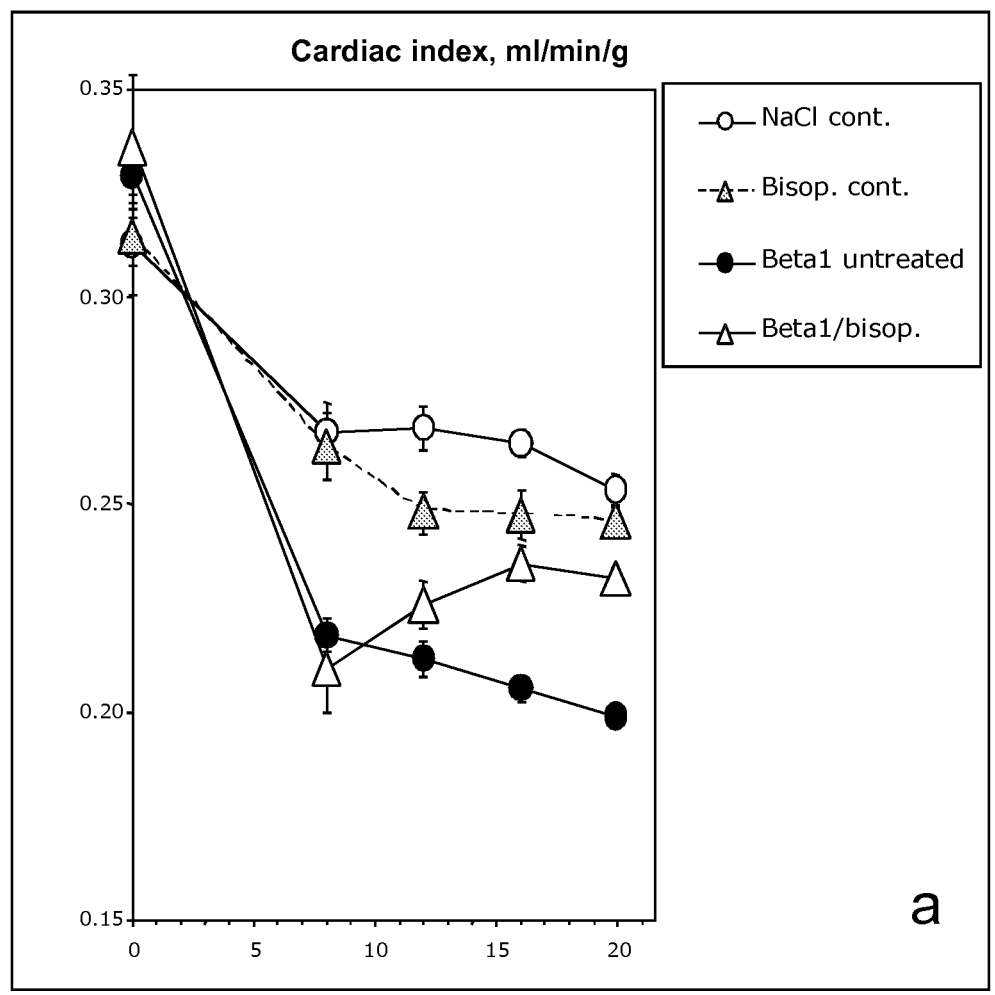
Figure 11B:
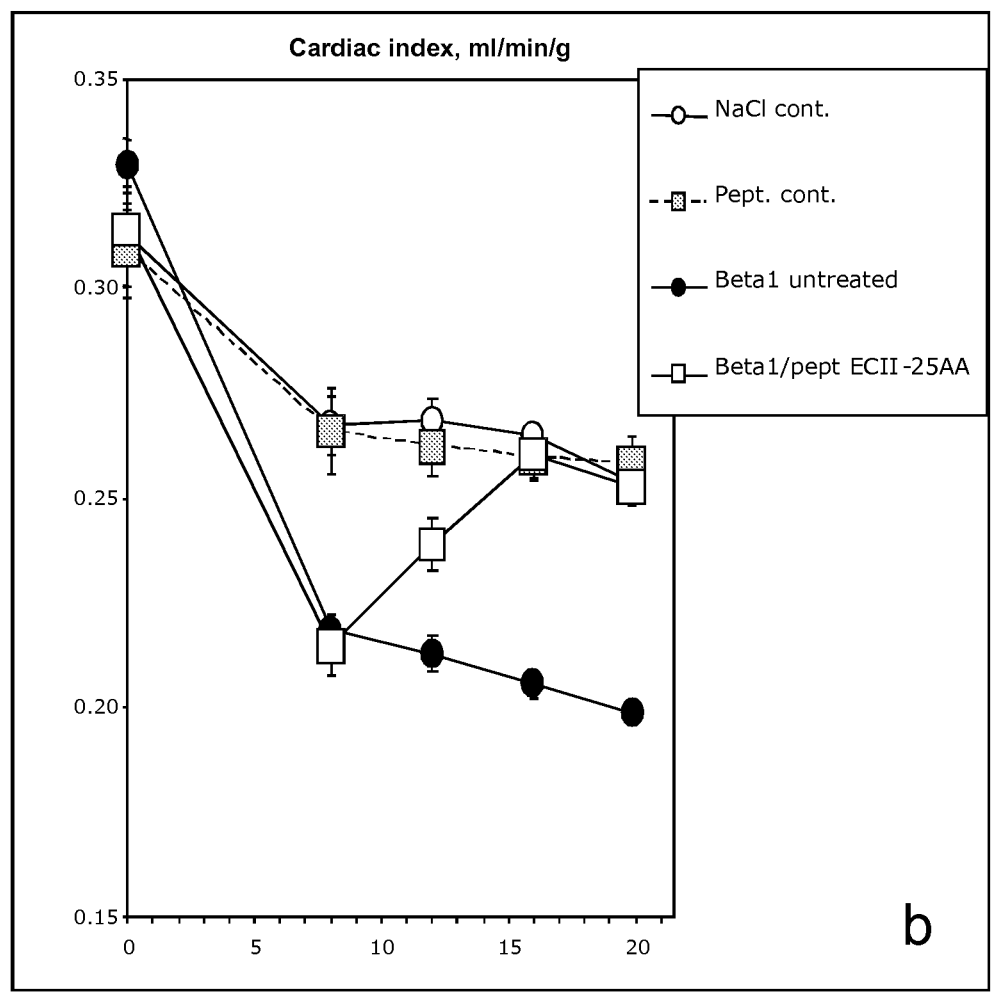
Figure 11C:
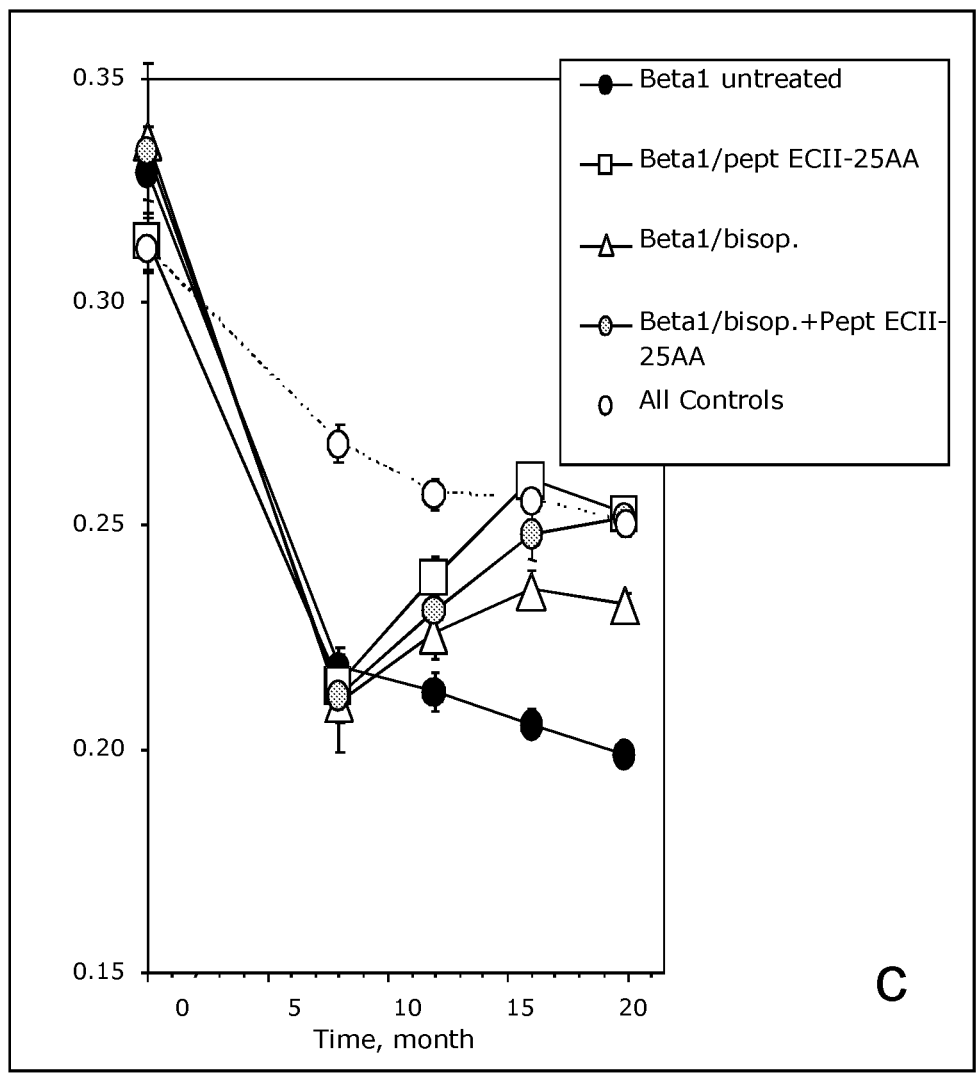
Figure 11D:
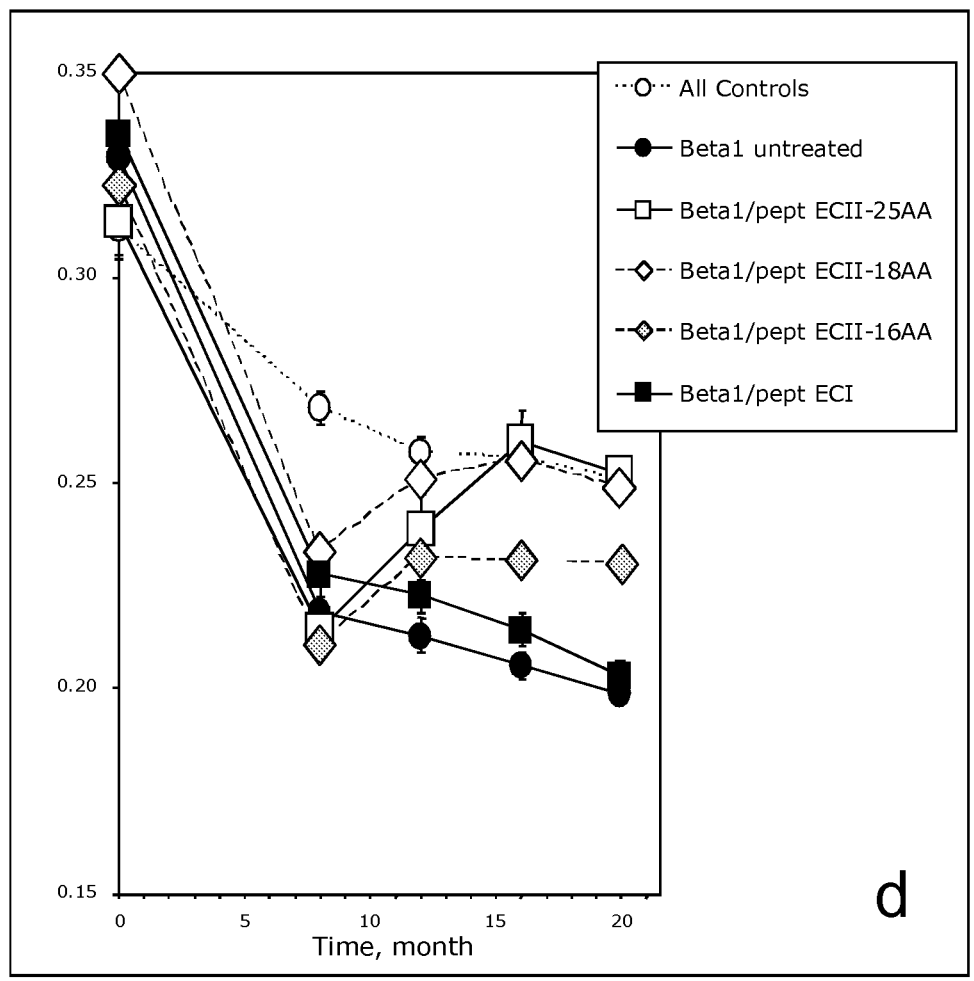

In general, the number of amino acids and thus the length of the primary structure appears to be crucial for the biological effects of the peptides of the present invention. A peptide-length equal to or above 26 amino acids (primary structure) is thought to be capable of stimulating directly (that is, without the use of carrier proteins) immunocompetent T-cells and thus provoke a paradoxal increase in anti-β1-receptor antibody production through T-cell mediated B-cell stimulation. Therefore, in the frame of the therapy study a limited number of pilot animals was treated with shorter peptide-variants of the 25 amino-acid peptide Ic, i.e. variants comprising either 18 or 16 amino-acids of the cyclic peptide. The used constructs were: ECII-18AA, cyclo(Ala-Asp-Glu-Ala-Arg-Arg-Cys-Tyr-Asn-Asp-Pro-Lys-Cys-Cys-Asp-Phe-Val-Gln) (SEQ ID NO:1); and ECII-16AA, cyclo(Ala-Arg-Arg-Cys-Tyr-Asn-Asp-Pro-Lys-Cys-Cys-Asp-Phe-Val-Tyr-Gln) (SEQ ID NO.2). Upon administration of shorter peptide-variants of the present invention peptide every 4 weeks, a rapid decrease in the specific anti-beta 1-$EC_{II}$ antibody titer was equally observed within the first 6 months of therapy. Whereas in the following months the circulating anti-β1-$EC_{II}$ antibody titers were reduced by about a same extent with either the 25 AA cylic peptide Ic or the 18 AA construct (see FIG. 8b), both yielding also a similar biological efficiency (i.e. reversal of the cardiomyopathic phenotype; see FIG. 10d), the 16 AA construct tended to be less effective with regard to both, the continuous reduction of circulating anti-β1-$EC_{II}$ antibody titers (see grey diamonds, FIG. 8b: upon peptide injection the antibody-titers remain stable instead of decreasing) and biological efficiency (i.e. ambiguous results in 2 treated rats with one animal having complete reversal of the cardiomyopathic phenotype, the other animal progressive LV dilatation and dysfunction; see FIGS. 10d and 11d). These preliminary results indicate that a certain length of the cyclic receptor-homologous peptides seems to be necessary to obtain the beneficial biological effects. However, it should be noted that with the 16 AA at least the progression of the disease was stopped or stabilized (comparable with the effects of a monotherapy with beta-blocking agents), as monitored by echocardiography within the 12 months during which the animals underwent this kind of treatment, compared with untreated anti-beta-1-$EC_{II}$-antibody positive animals (FIG. 10d).

EXAMPLE 7

Diagnostic Assay for β-Receptor Antibodies Using cAMP System

This detection of β-receptor antibodies (anti-$β_1$-Abs) in body fluids is based on the measurement of the impact of antibodies on the β receptor mediated signal transduction by optical detection of changes in the concentration of the intracellular messenger cyclic adenosine monophosphate (cAMP). Such a cAMP test system is, in principle, described in PCT-application WO 2005/052186.

To detect anti-$\beta_1$-Abs by their ability to induce $\beta_1$-receptor-mediated increases in cAMP, a new highly sensitive cAMP sensor (Epac1-camps) using fluorescence resonance energy transfer is employed. With this technology, a total of 56 patient sera and 40 control sera of a collective were analyzed using this method, whereby the patient collective is the same as already published by Jahns et al. in 1999 and assayed using peptide immuno assay (ELISA) and $^{125}$iodine labelled cAMP assays for $\beta$-receptor antibodies (Jahns et al., *Circulation* 1999, supra). All those patients which had been $\beta$-receptor antibody-positive (n=17) in this earlier study, also showed a significant Epac-1 signal (49±4%). IgG from controls and from about half (17/39) of DCM patients previously judged anti-$\beta_1$-EC$_{II}$-negative did not significantly affect cellular cAMP.

Surprisingly, the new technology detected anti-$\beta_1$-Abs in more than half (22/39) of DCM patients formerly judged antibody-negative, but the cAMP signals induced by these antibodies were generally lower (31±5%) than in the previous group.

Betablockers failed to fully prevent the antibody-induced $\beta_1$-receptor activation, with carvedilol being more effective than other $\beta$-blockers. Blocking experiments demonstrated that "high" or "low" activator IgG were blocked better by peptides corresponding to the second or first extracellular $\beta_1$-receptor-loop, respectively.

Taken together, the analysis of Epac-FRET signals from all 56 patients revealed an anti-beta 1-Ab prevalence of almost 70% (n=39/56) in DCM, which is much higher than detected by ELISA, immunofluorescence, and cAMP-RIA which proves the suitability of the peptides according to the present invention for the diagnosis of DCM. The Abs+ group can be separated into two subgroups on the basis of the FRET-data, which were classified as "low" (FRET amplitude 20-40% of isomax) and "high" activators (FRET amplitude ≥40% of isomax).

The two newly identified FRET-positive populations were studied in more detail. Analyzing the concentration-response relation we found that "low" activator IgG, even at higher concentrations, did not achieve cAMP levels of a similar order of magnitude as induced by "high" activator IgG (FIG. 23). This finding makes lower titers of anti-beta1-Abs in sera of "low" activators as a possible explanation for the "lower" cAMP response rather unlikely, and suggests a differential mechanism of action of this type of anti-beta1-Abs at the receptor level.

One reason for qualitative differences between antibodies in terms of FRET activity might be differences in the receptor-epitopes targeted by different anti-$\beta_1$-Abs. Previously functional anti-$\beta_1$-Abs against the $\beta_1$-EC$_{II}$ and $\beta_1$-EC$_I$ epitopes have also been generated successfully in animals by immunization, suggesting a certain antigenicity of these two epitopes (Mobini R, et al., *J. Autoimmun.* 1999, 13:179-186). To analyze whether different targeted epitopes might account for "high" or "low" FRET-activating capacities of anti-$\beta_1$-Abs, we incubated them with synthetic peptides corresponding to $\beta_1$-EC$_{II}$ or to $\beta_1$-EC$_I$, and analyzed the blocking effect of each of these peptides. These blocking experiments revealed that FRET-signals of "high" activator IgG could be attenuated by peptides corresponding to $\beta_1$-EC$_{II}$, but not by $\beta_1$-EC$_I$-peptides (7 patients tested; FIG. 24). In contrast, "low" activator IgG were only inhibited by peptides corresponding to $\beta_1$-EC$_I$ (8 patients tested; FIG. 24). All sera from DCM patients with anti-$\beta_1$-Abs yielding cAMP signals near the cut-off value between "high" and "low" activators were studied in such blocking experiments to ascertain the accuracy of our classification. The three previously Abs-judged patients exhibiting strong Epac-FRET signals (FRET response between 40-60%) were confirmed as "high" activator anti-$\beta_1$-EC$_{II}$ Abs, whereas all "low" activator IgG tested (yielding Epac-FRET responses between 20-40%) were inhibited by the $\beta_1$-EC$_I$ peptide. These data are consistent with the hypothesis that the differences in cAMP production of "high" and "low" activators most likely rely on the different epitopes targeted, and thus on different active receptor conformations induced. To address the question whether the differences in type and activating capacity of anti-$\beta_1$-Abs might be relevant for the clinical course of heart failure due to DCM we employed multivariable Cox regression in a retrospective analysis on all-cause mortality in the 56 DCM patients analyzed here over a follow-up period of 10 years. FIG. 4 depicts the survival curves grouped according to "no", "low", and "high" activators, adjusted for age, sex, New York Heart Association functional class, hemodynamic status, and medication. The mortality risk in the group of "low" activators was not significantly different from patients negative for activating anti-$\beta_1$-Abs. In contrast, "high" activators had a significantly higher mortality than "low" activators, suggesting that anti-$\beta_1$-EC$_{II}$ Abs are associated with a worse prognosis in DCM. This corroborates the potential pathophysiological and clinical relevance of activating anti-beta 1-Abs in heart failure.

In this assay for antibodies directed against $\beta$-adrenergic receptors the antibody induced cAMP production is measured in single cells such as, for example, HEK 293 cells or CHW cells which express the $\beta$-adrenergic receptor preferably in a concentration of 0.15 b is 0.3 pmol/mg membrane protein and are transiently transfected with an Epac-1 sensor.

The Epac-1 sensor as used is a fusion protein of Epac (exchange protein-1 directly activated by cAMP) and the binding domain E157-E316 coupled to a yellow fluorescent protein (YFP) and the cyan fluorescent protein (CFP) as described in the paper of Nikolaev et al. (JBC. 2004, 279 (36), 37215-8).

These cells are transfected preferably with 10 µg Epac-1 sensor/10 cm dish (diameter) using preferably calcium phosphate precipitation. The medium is preferably changed 12 to 18 hours after transfection. Preferably, 24 to 48 hours after transfection the antibody-induced receptor-mediated signal transduction is determined by measuring the changes in the cellular cAMP titre using the fluorescence resonance energy transfer described in Nikoaev et al. (supra).

The assay is preferably performed using serum samples of patients suffering from dilated cardiomyopathy and healthy controls. The IgG antibodies are preferably isolated from the serum using caprylic acid method, as described in the paper of Jahns et al. (Eur. J. Pharmacol., 1996, 113, 1419-1429). Prior to use the samples are preferably diluted with PBS buffer 1:6. Upon addition of the antibodies an increase of the intracellular cAMP level can be detected after about 100 to about 150 seconds, as expressed by a decrease in the fluorescence signal generated by the binding of cAMP to the Epac-1 sensor (corresponding to activation of the receptor). The antibody-induced value is calculated as percentage of the value obtained upon addition of 5 µM of the $\beta$-adrenergic agonist isoproterenol.

Apart from that, using this particular assay two further antibody positive patient groups were identified: three patients had a receptor antibody having a similar effect on intracellular cAMP-increase (44±2%) and another 19 patients had Epac-1-FRET-positive antibodies which had a significantly lower effect on cAMP-increase (31±5%).

Blocking experiments using epitope-homologous peptides showed that the antibodies of the first group are directed against the second extracellular β1-receptor loop, whereas the antibodies of the second group are directed against the first extracellular β1-receptor loop.

This novel method of detecting anti-beta1-Abs proved to be much faster and more sensitive than previous methods and is additionally suitable to identify functionally active β-receptor antibodies against various receptor domains. It also revealed an insufficient ability of β-blockers to prevent the anti-beta1-Ab-induced receptor activation. It opens new venues for the research on anti-beta1-Abs in heart failure and eventual treatment options.

The features of the present invention disclosed in the specification, the claims and/or the drawings may both separately and in any combination thereof be material for realizing the invention in various forms thereof.

What is claimed is:

1. A method for diagnosing a heart disease in a subject comprising:

A) introducing to a blood or serum sample from the subject one or more peptides selected from the group consisting of:

a) a cyclic peptide of formula I:

(SEQ ID NO: 3)
cyclo(Ala-x-x-x-x-x-x-x-x-Cys-x-x-x-Pro-x-Cys-Cys-$x_k$-Gln), wherein k is any integer from 0 to 6; and
wherein x is any amino acid;

b) a cyclic peptide of formula II:

(SEQ ID NO: 4)
Cyclo(Ala-x-x-Trp-x-x-Gly-x-Phe-x-Cys-$x_h$-Gln), wherein h is any integer from 0 to 2; and
wherein x is any amino acid;

c) a cyclic peptide of formula III:

(SEQ ID NO: 5)
Cyclo(Ala-x-x-x-x-x-x-x-x-Cys-$x_j$-Cys-x-x-x-Pro-x-Cys-Cys-$x_i$-Gln), wherein j is any integer from 0 to 4;
wherein i is any integer from 0 to 6; and
wherein x is any amino acid; and d) a peptide of formula IV:

(SEQ ID NO: 6)
Ala-$x_l$-Cys-$x_m$-Cys-x-x-x-Pro-x-Cys-Cys-$x_n$-Gln, wherein l is 9;
wherein m is any integer from 0 to 4;
wherein n is any integer from 0 to 6; and
wherein x is any amino acid;

B) performing an assay to detect levels of anti-β-adrenergic receptor antibodies that interact with the one or more peptides in the sample; and C) assessing a risk of or presence of the heart disease in the subject based on the level of anti-β-adrenergic receptor antibodies detected in the sample.

2. The method according to claim 1, wherein x is any naturally occurring L amino acid.

3. The method according to claim 1, wherein one of the one or more peptides is a cyclic peptide of formula Ia:

(SEQ ID NO: 7)
cyclo(Ala-$x_2$-x-$x_1$-x-$x_1$-$x_1$-x-$x_2$-$x_2$-Cys-x-x-$x_1$-Pro-x-Cys-Cys-$x_k$-Gln), wherein:
$x_1$ is an acidic amino acid; and
$x_2$ is a basic amino acid.

4. The method according to claim 1, wherein the peptide is a peptide of formula Ic:

(SEQ ID NO: 9)
cyclo(Ala-Arg-Ala-Glu-Ser-Asp-Glu-Ala-Arg-Arg-Cys-Tyr-Asn-Asp-Pro-Lys-Cys-Cys-Asp-Phe-Val-Thr-Asn-Arg-Gln).

5. The method according to claim 1, wherein one of the one or more peptides is a cyclic peptide of formula IIa:

(SEQ ID NO: 10)
Cyclo(Ala-$x_4$-$x_2$-Trp-$x_1$-$x_3$-Gly-$x_4$-Phe-$x_3$-Cys-$x_n$-Gln), wherein n is any integer from 0 to 2; and
wherein:
$x_1$ is any acidic amino acid;
$x_2$ is any basic amino acid;
$x_3$ is selected from the group consisting of Leu, Ile, Val, Met, Trp, Tyr and Phe; and
$x_4$ is selected from the group consisting of Ser, Thr, Ala and Gly.

6. The method according to claim 5, wherein one of the one or more peptides is a peptide of formula IIb:

(SEQ ID NO: 11)
cyclo(Ala-Gly-Arg-Trp-Glu-Tyr-Gly-Ser-Phe-Phe-Cys-Glu-Leu-Gln)

or a peptide of formula IIc:

(SEQ ID NO: 12)
cyclo(Ala-Gly-Arg-Trp-Glu-Tyr-Gly-Ser-Phe-Phe-Cys-Gln).

7. The method according to claim 1, wherein one of the one or more peptides is a cyclic peptide of formula IIIa:

(SEQ ID NO: 13)
Cyclo(Ala-$x_4$-$x_2$-$x_3$-$x_1$-$x_3$-$x_3$-$x_4$-$x_3$-$x_3$-Cys-$x_j$-Cys-x-x-x-Pro-x-Cys-Cys-$x_i$-Gln), wherein i is any integer from 0 to 6;
wherein j is any integer from 0 to 4; and wherein:
$x_1$ is any acidic amino acid;
$x_2$ is any basic amino acid;
$x_3$ is selected from the group consisting of Leu, Ile, Val, Met, Trp, Tyr and Phe; and
$x_4$ is selected from the group consisting of Ser, Thr, Ala and Gly.

8. The method according to claim 1, wherein one of the one or more peptides is a peptide of formula IIIb:

(SEQ ID NO: 14)
Cyclo(Ala-Gly-Arg-Trp-Glu-Tyr-Gly-Ser-Phe-Phe-Cys-Glu-Ala-Arg-Arg-Cys-Tyr-Asn-Asp-Pro-Lys-Cys-Cys-Asp-Phe-Val-Thr-Asn-Arg-Gln).

9. The method according to claim 1, wherein one of the one or more peptides is a linear peptide of formula IVa:

(SEQ ID NO: 15)
Ala-$x_4$-$x_2$-$x_3$-$x_1$-$x_3$-$x_3$-$x_4$-$x_3$-$x_3$-Cys-$x_m$-Cys-x-x-x-Pro-x-Cys-Cys-$x_n$-Gln), wherein n is any integer from 0 to 6;
wherein m is any integer from 0 to 4; and
wherein
$x_1$ is an acidic amino acid;
$x_2$ is a basic amino acid;
$x_3$ is selected from the group consisting of Leu, Ile, Val, Met, Trp, Tyr and Phe; and
$x_4$ is selected from the group consisting of Ser, Thr, Ala and Gly.

10. The method according to claim 1, wherein one of the one or more peptides is a peptide of formula IVb:

(SEQ ID NO: 16)
Ala-Gly-Arg-Trp-Glu-Tyr-Gly-Ser-Phe-Phe-Cys-Glu-Ala-Arg-Arg-Cys-Tyr-Asn-Asp-Pro-Lys-Cys-Cys-Asp-Phe-Val-Thr-Asn-Arg-Gln.

11. The method according to claim 7, wherein an S—S linkage is formed by two Cys residues of the peptide.

12. The method according to claim 1, wherein additional bonds are formed by $NH_2$ and COOH groups present in side chains of constituent amino acids of the one or more peptides.

13. The method according to claim 1, wherein the heart disease is selected from the group consisting of infectious and non-infectious heart disease, ischemic and non-ischemic heart disease, inflammatory heart disease and myocarditis, cardiac dilatation, idiopathic cardio-myopathy, idiopathic dilated cardiomyopathy, immune-cardiomyopathy, heart failure, and any cardiac arrhythmia including ventricular and supraventricular premature capture beats.

14. The method according to claim 13, wherein the heart disease is idiopathic dilated cardiomyopathy.

15. The method according to claim 13, wherein the one or more peptides bind to anti-β-adrenergic receptor (anti-β-AR) antibodies and the heart disease is anti-β-AR antibody-induced dilated immune-cardiomyopathy.

16. The method according to claim 1, wherein the method is a FRET-based method.

17. A method for diagnosing a heart disease in a subject comprising:
1) introducing to a blood or serum sample from the subject one or more peptides selected from the peptides consisting of a cyclic peptide of formula Ib:

(SEQ ID NO: 8)
Cyclo($x_4$-$x_2$-$x_4$-$x_1$-$x_4$-$x_1$-$x_1$-$x_4$-$x_2$-$x_2$-Cys-$x_3$-$x_5$-$x_1$-Pro-$x_2$-Cys-Cys-$x_1$-$x_3$-$x_3$-$x_4$-$x_5$-$x_2$-$x_5$), wherein:
$x_1$ is any acidic amino acid;
$x_2$ is any basic amino acid;
$x_3$ is selected from the group consisting of Leu, Ile, Val, Met, Trp, Tyr and Phe;
$x_4$ is selected from the group consisting of Ser, Thr, Ala and Gly; and
$x_5$ is selected from the group consisting of Gln and Asn;
2) performing an assay to detect levels of anti-β-adrenergic receptor antibodies that interact with the one or more peptides in the sample; and
3) assessing risk of or presence of heart disease in the subject based on the level of anti-β-adrenergic receptor antibodies detected in the sample.

18. The method according to claim 17, wherein the heart disease is idiopathic dilated cardiomyopathy.

19. The method according to claim 18, wherein the one or more peptides bind to anti-β-adrenergic receptor (anti-β-AR) antibodies and the heart disease is anti-β-AR antibody-induced dilated immune-cardiomyopathy.

20. The method according to claim 17, wherein the method is a FRET-based method.

\* \* \* \* \*

UNITED STATES PATENT AND TRADEMARK OFFICE
CERTIFICATE OF CORRECTION

PATENT NO.       : 8,716,030 B2
APPLICATION NO.  : 13/449966
DATED            : May 6, 2014
INVENTOR(S)      : Roland Jahns et al.

It is certified that error appears in the above-identified patent and that said Letters Patent is hereby corrected as shown below:

On the Title Page:

Item (73) correct the Assignee to "Julius-Maximilians-Universität Würzburg, A German University, Wurzburg (DE)"

Signed and Sealed this
First Day of July, 2014

Michelle K. Lee
*Deputy Director of the United States Patent and Trademark Office*